US006413511B1

(12) United States Patent
Glorioso et al.

(10) Patent No.: US 6,413,511 B1
(45) Date of Patent: *Jul. 2, 2002

(54) CARTILAGE ALTERATIONS BY ADMINISTERING TO JOINTS CHONDROCYTES COMPRISING A HETEROLOGOUS POLYNUCLEOTIDE

(75) Inventors: Joseph C. Glorioso, Cheswick; Christopher H. Evans, Pittsburgh; Paul D. Robbins, Pittsburgh; Richard Kane, Pittsburgh, all of PA (US)

(73) Assignee: University of Pittsburgh of the Commonwealth System of Higher Education, Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/466,932

(22) Filed: Jun. 6, 1995

Related U.S. Application Data

(63) Continuation-in-part of application No. 08/381,603, filed on Jan. 27, 1995, now Pat. No. 5,858,355, which is a continuation-in-part of application No. 08/027,750, filed on Mar. 8, 1993, now abandoned, and a continuation-in-part of application No. 08/183,563, filed on Jan. 18, 1994, now abandoned, said application No. 08/027,750, is a continuation-in-part of application No. 07/630,981, filed on Dec. 20, 1990, now abandoned, said application No. 08/183,563, is a continuation of application No. 07/963,928, filed on Oct. 20, 1992, now abandoned, which is a continuation of application No. 07/630,981.

(51) Int. Cl.⁷ .................. A61K 48/00; A01K 67/00; A01N 63/00; C12N 15/00

(52) U.S. Cl. .................. 424/93.21; 424/93.2; 435/325; 800/9

(58) Field of Search .................. 514/44; 435/320.1, 435/375, 69.1, 172.3, 325; 536/23.1; 424/93.21, 93.2; 800/9

(56) References Cited

U.S. PATENT DOCUMENTS

| | | | |
|---|---|---|---|
| 4,396,601 A | 8/1983 | Salser et al. | 424/94 |
| 4,766,069 A | 8/1988 | Auron et al. | 435/70 |
| 4,778,806 A | 10/1988 | Bender et al. | 514/336 |
| 4,780,470 A | 10/1988 | Bender et al. | 514/341 |
| 4,794,114 A | 12/1988 | Bender et al. | 514/333 |
| 4,816,436 A | 3/1989 | Jacobs | 514/2 |
| 4,870,101 A | 9/1989 | Ku et al. | 514/476 |
| 4,935,343 A | 6/1990 | Allison et al. | 435/7 |
| 4,968,607 A | 11/1990 | Dower et al. | 435/69.1 |
| 5,081,228 A | 1/1992 | Dower et al. | 530/35.1 |
| 5,180,812 A | 1/1993 | Dower et al. | 530/351 |

FOREIGN PATENT DOCUMENTS

| | | | |
|---|---|---|---|
| DE | 4219626 | 12/1993 | C12N/15/79 |
| WO | 9211359 | * 7/1992 | |
| WO | WO 94/09118 | 4/1994 | C12N/5/06 |
| WO | WO 96/34955 | 11/1996 | C12N/15/12 |

OTHER PUBLICATIONS

Grande et al (1989) J. Orthopedic Research 7:208–218.*
Mueller et al (1992) Keystone Symposia Apr. 3–9, 1992 Gene Transfer, Replacement and Augmentation, Abstract #v207.*
Watkitani et al. (1989) J. Bone Joint Surg [Br] 71B:74–80.*
A Rizzino (1988) Developmental Biology 130:411–422.*
Chin et al (1990) The Fiaseb Journal 4:1481–1487.*
Lynch et al. (1991) J. Periodontol 62:458–467.*
Crystal (1995) Science 270, 404–410.*
Kang et al (1997) Osteoarthritis and Carlilage 5, 139–143.*
Mallein–Gerin et al (1993) Proced. Natl. Acad. Sci. 90, 3289–3293.*
Science News Report, 1995, Science 269, 1050–1055.*
Blau et al (1995) New Eng. J. Med., 1204–1207.*
Fanslow et al., "Regulation of Alloreactivity in Vivo by a Soluble Form of the Interleukin–1 Receptor", *Science*, vol. 248, pp. 739–742 (May 1990).
Gao et al., "A Novel Cationic Liposome Reagent for Efficient TRansfection of Mammalian Cells", *Biochemical and Biophysical Research Communications*, vol. 179, No. 1, 280–285 (Aug. 1991).
Bandara et al., "Intraarticular Expression of IRAP by Gene Transfer", *Arthritis Rhenum.*, vol. 39 (supp), S193, C161 (1992).
Evans, "Transferring Therapeutic Genes to Joints: A Pittsburgh Idea", *The Pittsburgh Orthopaedic Journal*, vol. 3, pp. 130–131 (1992).
Evans et al., "Gene Transfer to Joints for Arthritis Therapy", *J. Cell Biochem.*, 16F:V207 (1992).
Bandara et al., "Gene Transfer to Synoviocytes: Prospects for Gene Treatment of Arthritis", *DNA and Cell Biology*, vol. 11, No. 3, pp. 227–231 (1992).
Evans et al., "Synovial Cell Transplants for Gene Transfer to Joints", Transplantation Proceedings, vol. 24, No. 6, p. 2966 (Dec. 1992).

(List continued on next page.)

*Primary Examiner*—Deborah Crouch
(74) *Attorney, Agent, or Firm*—Townsend and Townsend and Crew LLP

(57) ABSTRACT

The subject invention concerns a method of introducing at least one DNA sequence expressing a protein or protein fragment which substantially alleviates articular cartilage defects. This method involves in vitro culture of chondrocytes, transfection of the chondrocytes with a recombinant vector housing the DNA sequence to be expressed, and delivery of the transfected chondrocytes to the damaged cartilage region. This method can also be used in tandem with synovial cell delivery techniques of the present invention. This method is also useful as a model in animal studies regarding joint pathologies.

22 Claims, 19 Drawing Sheets

OTHER PUBLICATIONS

Bandara et al., "Gene Transfer to Synovium", Trans. Orthop. Res. Soc., 18, p. 242 (1993).

Grande et al., "The Repair of Experimentally Produced Defects in Rabbit Articular Cartilage by Autologous Chondrocyte Transplantation", *Journal of Orthopaedic Research*, vo. 7, No. 2, pp. 208–218 (1989).

Wakitani et al., "Repair of Rabbit Articular Surfaces with Allograft Chrondrocytes Embedded in Collagen Gel", *The Journal of Bone and Joint Surgery*, vol. 71–B, No. 1, pp. 74–80 (Jan. 1989).

Chin et al., "Interleukin 1 Receptors on Rabbit Articular Chondrocytes: Relationship Between Biological Activity and Receptor Binding Kinetics", *The FASEB Journal*, vol. 4, pp. 1481–1487 (Mar. 1990).

Banerjee et al., "Immunosuppression of Collagen–Induced Arthritis in Mice with an Anti–IL–2 Receptor Antibody", *The Journal of Immunology*, vol. 141, No. 4, pp. 1150–1154 (Aug. 1988).

Danos et al., "Safe and Efficient Generation of Recombinant Retroviruses with Amphotropic and Ecotropic Host Ranges", *Proc. Natl. Acad. Sci. USA*, vol. 85, pp. 6460–6464 (Sep. 1988).

Rosenberg et al., "Grafting Genetically Modified Cells to the Damaged Brain: Restorative Effects of NGF Expression", *Science*, vol. 242, pp. 1575–1578 (Dec. 1988).

Aston and Bentley, "Repair of Articular Surfaces by Allografts of Articular and Growth–Plate Cartilage", *The Journal of Bone and Joint Surgery*, vol. 68 B, No. 1, pp. 29–35 (Jan. 1986).

Pettipher et al., "Interleukin 1 Induces Leukocyte Infiltration and Cartilage Proteoglycan Degradation in the Synovial Joint", *Proc. Natl. Acad. Sci. USA*, vol. 83, pp. 8749–8753 (Nov. 1986).

Korman et al., "Expression of Human Class II Major Histopcompatibilty Complex Antigens Using Retrovirus Vectors", *Proc. Natl. Acad. Sci. USA*, vol. 84, pp. 2150–2154 (Apr. 1987).

* cited by examiner

CARTILAGE ALTERATIONS BY ADMINISTERING TO JOINTS CHONDROCYTES COMPRISING A HETEROLOGOUS POLYNUCLEOTIDE

CROSS-REFERENCE TO RELATED APPLICATION

This is a continuation-in-part application of U.S. application Ser. No. 08/381,603, filed Jan. 27, 1995, now U.S. Pat. No. 5,858,355, which is a continuation-in-part of both U.S. application Ser. No. 08/027,750, filed Mar. 8, 1993, and U.S. application Ser. No. 08/183,563, filed Jan. 18, 1994, now abandoned,; U.S. application Ser. No. 08/027,750, now abandoned, is a continuation-in-part of U.S. application Ser. No. 07/630,981, filed Dec. 20, 1990, now abandoned; U.S. application Ser. No. 08/183,563, now abandoned, is a file wrapper continuation of U.S. Ser. No. 07/963,928, filed on Oct. 20, 1992 now abandoned, which was a file wrapper continuation of U.S. Ser. No. 07/630,981, filed on Dec. 20, 1990, now abandoned.

BACKGROUND OF THE INVENTION

1. Field of the Invention

The present invention relates to a method of introducing at least one gene encoding a product into at least one cell of a connective tissue of a mammalian host for use in treating the mammalian host. This method discloses employing DNA vector molecules containing a gene encoding the product and infecting the connective tissue cells of the mammalian host using the DNA vector molecule. This invention provides a method of introducing at least one gene encoding a product into at least one cell of a connective tissue of a mammalian host for use in treating the mammalian host including employing non-viral means for effecting such introduction.

The present invention discloses ex vivo and in vivo techniques for delivery of a DNA sequence of interest to the connective tissue cells of the mammalian host. The ex vivo technique involves prior removal and culture of target autologous connective tissue cells, in vitro infection of the DNA sequence, DNA vector or other delivery vehicle of interest into the connective tissue cells, followed by transplantation to the modified connective tissue cells to the target joint of the mammalian host, so as to effect in vivo expression of the gene product of interest. The in vivo technique bypasses the requirement for in vitro culture of target connective tissues cells; instead relying on direct transplantation of the DNA sequence, DNA vector or other delivery vehicle to the target in vivo connective tissue cells, thus effecting expression of the gene product of interest.

The present invention also relates to a method to produce an animal model for the study of connective tissue pathologies and systemic indices of inflammation.

The present invention further relates to a method of using a gene encoding a truncated interleukin-1 receptor to resist the deleterious pathological changes associated with arthritis. More specifically, this invention provides a method wherein a gene coding for an extracellular interleukin-1 binding domain of an interleukin-1 receptor is introduced into synovial cells of a mammalian host in vivo for neutralizing the destructive activity of interleukin-1 upon cartilage and other soft tissues. As an alternative, the patients own synovial cells are transduced in vitro and introduced back into the affected joint, using transplantation procedures such as for example, intra-articular injection.

As an alternative to the in vitro manipulation of synovia, the gene encoding the product of interest is introduced into liposomes and injected directly into the area of the joint, where the liposomes fuse with synovial cells, resulting in an in vivo gene transfer to synovial tissue. As an additional alternative to the in vitro manipulation of synovia, the gene encoding the product of interest is introduced into the area of the joint as naked DNA. The naked DNA enters the synovial cell, resulting in an in vivo gene transfer to synovial tissue.

As an another alternative, hematopoietic progenitor cells or the mature lymphoid or myeloid cells may be transfected in vitro, recovered and injected into the bone marrow or peripheral bloodstream of the patient using techniques known to the skilled artisan.

The present invention also relates to methods of using various DNA sequences disclosed throughout this specification to provide therapeutic treatment for damaged cartilage, particularly full thickness human articular cartilage defects, such as damaged articular cartilage surrounding any joint. More specifically, this invention further provides a method wherein a gene or DNA sequence encoding a biologically active fragment thereof is transferred into in vitro cultured chondrocytes, with the resulting transfected chondrocytes surgically introduced into the area of cartilage damage of the mammalian host as a composition comprising the transduced chondrocyte polulation along with a suitable scaffold, such as a collagen gel, so as to effect in vivo expression of the DNA sequence of interest. Such genes or DNA fragments include but will not be limited to sequences encoding a biologically active protein or fragment of an interleukin-1 receptor antagonist protein, extracellular interleukin-1 binding domain of an interleukin-1 receptor, TGF-$\beta_1$, TGF-$\beta_2$, TGF-$\beta_3$, and IGF-1.

2. Brief Description of the Related Art

Arthritis involves inflammation of a joint that is usually accompanied by pain and frequently changes in structure. Arthritis may result from or be associated with a number of conditions including infection, immunological disturbances, trauma and degenerative joint diseases such as, for example, osteoarthritis. The biochemistry of cartilage degradation in joints and cellular changes have received considerable investigation.

In a healthy joint, cells in cartilage (chondrocytes) and the surrounding synovium (synoviocytes) are in a resting state. In this resting state, these cells secrete basal levels of prostaglandin $E_2$ and various neutral proteinases, such as, for example, collagenase, gelatinase and stromelysin, with the ability to degrade cartilage. During the development of an arthritic condition, these cells become activated. In the activated state, synoviocytes and chondrocytes synthesize and secrete large amounts of prostaglandin $E_2$ and neutral proteinases.

In efforts to identify pathophysiologically relevant cell activators, it has been known that the cytokine interleukin-1 activates chondrocytes and synoviocytes and induces cartilage breakdown in vitro and in vivo. Additionally, interleukin-1 is a growth factor for synoviocytes and promotes their synthesis of matrix, two properties suggesting the involvement of interleukin-1 in the synovial hypertrophy that accompanies arthritis. In contrast, interleukin-1 inhibits cartilaginous matrix synthesis by chondrocytes, thereby suppressing repair of cartilage. Interleukin-1 also induces bone resorption and thus may account for the loss of bone density seen in rheumatoid arthritis. Interleukin-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness.

The major source of interleukin-1 in the joint is the synovium. Interleukin-1 is secreted by the resident synoviocytes, which are joined under inflammatory conditions by macrophages and other white blood cells.

Much attention has been devoted to the development of a class of agents identified as the "Non-Steroidal Anti-Inflammatory Drugs" (hereinafter "NSAIDs"). The NSAIDs inhibit cartilage synthesis and repair and control inflammation. The mechanism of action of the NSAIDs appears to be associated principally with the inhibition of prostaglandin synthesis in body tissues. Most of this development has involved the synthesis of better inhibitors of cyclo-oxygenase, a key enzyme that catalyzes the formation of prostaglandin precursors (endoperoxides) from arachidonic acid. The anti-inflammatory effect of the NSAIDs is thought to be due in part to inhibition of prostaglandin synthesis and release during inflammation. Prostaglandins are also believed to play a role in modulating the rate and extent of leukocyte infiltration during inflammation. The NSAIDs include, such as, for example, acetylsalicylic acid (aspirin), fenoprofen calcium (Nalfon® Pulvules®, Dista Products Company), ibuprofen (Motrin®, The Upjohn Company), and indomethacin (Indocin®, Merck, Sharp & Dohme).

In contrast, the studies upon which the present invention is based show that production of the various neutral proteinases with the ability to degrade cartilage occurs even if prostaglandin synthesis is completely blocked.

Therapeutic intervention in arthritis is hindered by the inability to target drugs, such as the NSAIDs, to specific areas within a mammalian host, such as, for example a joint. Traditional routes of drug delivery, such as for example, oral, intravenous or intramuscular administration, depend upon vascular perfusion of the synovium to carry the drug to the joint. This is inefficient because transynovial transfer of small molecules from the synovial capillaries to the joint space occurs generally by passive diffusion. This diffusion is less efficient with increased size of the target molecule. Thus, the access of large drug molecules, for example, proteins, to the joint space is substantially restricted. Intra-articular injection of drugs circumvents those limitations; however, the half-life of drugs administered intra-articularly is generally short. Another disadvantage of intra-articular injection of drugs is that frequent repeated injections are necessary to obtain acceptable drug levels at the joint spaces for treating a chronic condition such as, for example, arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as for example, gastrointestinal upset and changes in the hematological, cardiovascular, hepatic and renal systems of the mammalian host.

It has been shown that genetic material can be introduced into mammalian cells by chemical or biologic means. Moreover, the introduced genetic material can be expressed so that high levels of a specific protein can be synthesized by the host cell. Cells retaining the introduced genetic material may include an antibiotic resistance gene thus providing a selectable marker for preferential growth of the transduced cell in the presence of the corresponding antibiotic. Chemical compounds for inhibiting the production of interleukin-1 are also known.

U.S. Pat. No. 4,778,806 discloses a method of inhibiting the production of interleukin-1 by monocytes and/or macrophages in a human by administering through the parenteral route a 2-2'-[1,3-propan-2-onediyl-bis(thio)] bis-1 H-imidazole or a pharmaceutically acceptable salt thereof. This patent discloses a chemical compound for inhibiting the production of interleukin-1. By contrast, in one embodiment of the present invention, gene therapy is employed that is capable of binding to and neutralizing interleukin-1.

U.S. Pat. No. 4,780,470 discloses a method of inhibiting the production of interleukin-1 by monocytes in a human by administering a 4,5-diaryl-2 (substituted) imidazole. This patent also discloses a chemical compound for inhibiting the production of interleukin-1.

U.S. Pat. No. 4,794,114 discloses a method of inhibiting the S-lipoxygenase pathway in a human by administering a diaryl-substituted imidazole fused to a thiazole, pyrrolidine or piperidine ring or a pharmaceutically acceptable salt thereof. This patent also discloses a chemical compound for inhibiting the production of interleukin-1.

U.S. Pat. No. 4,870,101 discloses a method for inhibiting the release of interleukin-1 and for alleviating interleukin-1 mediated conditions by administering an effective amount of a pharmaceutically acceptable anti-oxidant compound such as disulfiram, tetrakis [3-(2,6-di-tert-butyl-4-hydroxyphenyl) propionyloxy methyl] methane or 2,4-di-isobutyl-6-(N,N-dimethylamino methyl)-phenol. This patent discloses a chemical compound for inhibiting the release of interleukin-1.

U.S. Pat. No. 4,816,436 discloses a process for the use of interleukin-1 as an anti-arthritic agent. This patent states that interleukin-1, in association with a pharmaceutical carrier, may be administered by intra-articular injection for the treatment of arthritis or inflammation. In contrast, the present invention discloses a method of using and preparing a gene that is capable of binding to and neutralizing interleukin-1 as a method of resisting arthritis.

U.S. Pat. No. 4,935,343 discloses an immunoassay method for the detection of interleukin-1 beta that employs a monoclonal antibody that binds to interleukin-1 beta but does not bind to interleukin-1 alpha. This patent discloses that the monoclonal antibody binds to interleukin-1 beta and blocks the binding of interleukin-1 beta to interleukin-1 receptors, and thus blocking the biological activity of interleukin-1 beta. The monoclonal antibody disclosed in this patent may be obtained by production of an immunogen through genetic engineering using recombinant DNA technology. The immunogen is injected into a mouse and thereafter spleen cells of the mouse are immortalized by fusing the spleen cells with myeloma cells. The resulting cells include the hybrid continuous cell lines (hybridomas) that may be later screened for monoclonal antibodies. This patent states that the monoclonal antibodies of the invention may be used therapeutically, such as for example, in the immunization of a patient, or the monoclonal antibodies may be bound to a toxin to form an immunotoxin or to a radioactive material or drug to form a radio pharmaceutical or pharmaceutical.

U.S. Pat. No. 4,766,069 discloses a recombinant DNA cloning vehicle having a DNA sequence comprising the human interleukin-1 gene DNA sequence. This patent provides a process for preparing human interleukin-1 beta, and recovering the human interleukin-1 beta. This patent discloses use of interleukin-1 as an immunological reagent in humans because of its ability to stimulate T-cells and B-cells and increase immunoglobulin synthesis.

U.S. Pat. No. 4,396,601 discloses a method for providing mammalian hosts with additional genetic capability. This patent provides that host cells capable of regeneration are removed from the host and treated with genetic material including at least one marker which allows for selective advantage for the host cells in which the genetic material is capable of expression and replication. This patent states that the modified host cells are then returned to the host under regenerative conditions. In the present invention, genetic material may be directly introduced (a) into host cells in vivo or (b) into synoviocytes in vitro for subsequent transplantation back into the patient's joints.

U.S. Pat. No. 4,968,607 discloses a DNA sequence encoding a mammalian interleukin-1 receptor protein which exhibits interleukin-1 binding activity.

U.S. Pat. No. 5,081,228 discloses a DNA sequence encoding both the murine and human interleukin-1 receptor. This patent also provides a process for the in vitro expression of said DNA sequences.

U.S. Pat. No. 5,180,812 discloses a substantially pure preparation of the human interleukin-1 receptor protein.

In spite of these prior art disclosures, there remains a very real and substantial need for a method of introducing at least one gene encoding a product into at least one cell of a connective tissue of a mammalian host in vitro, or alternatively in vivo, for use in treating the mammalian host. Further, there is a need for a process wherein a gene encoding a truncated interleukin-1 receptor is used to resist the deleterious pathological changes associated with arthritis. More specifically there is a need for such a process where a gene coding for the extracellular interleukin-1 binding domain of the interleukin-1 receptor, capable of binding to and neutralizing interleukin-1 is expressed in host synovial cells in vivo. There is also a need to utilize one or more additional DNA sequences for delivery to and expression of a protein or protein fragment within a target host connective tissue cell, such as a synovial cell, so as to effect a treatment of various joint pathologies and concomitant systemic indices of inflammation.

There is also a very real and substantial need to treat various mammalian cartilage defects, in particular human articular and meniscal cartilage defects.

Brittberg et al. (1994, New England Journal of Medicine 331(14):879–895) disclose transplantation of non-modified human autologous chondrocytes cultured in vitro to correct articular cartilage defects. A biopsy of healthy cartilage was removed by arthroscopy from the damaged knee, cultured in vitro and transplantated by injection into the damaged area. The injected chondrocytes were secured within the damaged portion of articular cartilage by suture of periosteal flap taken from the medial tibia. No genetic modification of the cultured chondrocytes was reported or suggested by the authors.

Grande et al. (1989, J. Orthopaedic Research Society 7:208–219) utilized a similar surgical technique to transplant in vitro cultured rabbit chondrocytes in an attempt to repair a full-thickness cartilage defect.

The various techniques disclosed to date to treat full-thickness cartilage defects have had variable and limited success. None of these studies adequately demonstrate repair of the damaged cartilage with tissue which was histologically, biochemically, and biomechanically identical to normal cartilage. Moreever, the long term result has been poor as the repair tissue is fibrocartilage. None of these numerous attempts to overcome this long standing problem address adequate and/or appropriate cytokine mediation during the repair process. Multiple cytokines, such as transforming growth factor-$\beta$1 (TGF-$\beta$1) and insulin-like growth factor-1 (IGF-1), play significant roles in promoting chondrocyte anabolism and inhibiting chondrocyte catabolism. The presence of one or more of these cytokines during repair may be the key to regenerating normal cartilage. However, sustained delivery of sufficient quantities of a cytokine(s) to transplanted cells bound within a three-dimensional cartilage matrix would be difficult and impractical using the methods described above.

SUMMARY OF THE INVENTION

The present invention has met the hereinbefore described need. A method of introducing at least one gene encoding a product into at least one cell of a connective tissue of a mammalian host for use in treating the mammalian host is provided for in the present invention. This method includes employing recombinant techniques to produce a DNA vector molecule containing the gene encoding for the product and infecting the connective tissue cell of the mammalian host using the DNA vector molecule containing the gene coding for the product. The DNA vector molecule can be any DNA molecule capable of being delivered and maintained within the target cell or tissue such that the gene encoding the product of interest can be stably expressed. The DNA vector molecule preferably utilized in the present invention is either a viral DNA vector molecule or a plasmid DNA viral molecule. This method preferably includes introducing the gene encoding the product into the cell of the mammalian connective tissue for a therapeutic use.

One ex vivo method of treating a connective tissue disorder disclosed throughout this specification comprises initially generating a recombinant viral vector which contains a DNA sequence encoding a protein or biologically active fragment thereof. This recombinant viral vector is then used to infect a population of in vitro cultured connective tissue cells, resulting in a population of transfected connective cells. These transfected connective tissue cells are then transplanted to a target joint space of a mammalian host, effecting subsequent expression of the protein or protein fragment within the joint space. Expression of this DNA sequence of interest is useful in substantially reducing at least one deleterious joint pathology or indicia of inflammation normally associated with a connective tissue disorder.

The connective tissue cells are selected from the group of connective tissue consisting of a synovium, a cartilage, a tendon and a ligament, preferably synovial cells.

It is also preferred that a retroviral vector, such as MFG, be utilized as the viral vector.

Another preferred step in this ex vivo method is transplantation of transduced synovial cells by intraarticular injection.

It will be understood by the artisan of ordinary skill that the preferred source of cells for treating a human patient are the patients own cells, such as autologous synovial cells.

More specifically, this method includes employing as the gene a gene capable of encoding at least one of the materials which is selected from the group which includes (a) a human interleukin-1 receptor antagonist protein, preferably MFG-IRAP, or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a soluble TNF-$\alpha$ receptor protein or a biologically active derivative or fragment thereof; (e) a proteinase inhibitor, and (f) a cytokine, and employing as the viral vector at least one vector which is selected from the group which includes (a) a retroviral vector including at least one of the materials selected from the group which includes MFG and BAG, (b) an adeno-associated virus, (c) an adenovirus, and (d) a herpes virus, including but not limited to herpes simplex 1 or herpes simplex 2.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a soluble TNF-α receptor protein or a biologically active derivative or fragment thereof; (e) a proteinase inhibitor, and (f) a cytokine, and employing as the DNA plasmid vector any DNA plasmid vector known to one of ordinary skill in the art capable of stable maintenance within the targeted cell or tissue upon delivery, regardless of the method of delivery utilized. One such method is the direct delivery of the DNA vector molecule, whether it be a viral or plasmid DNA vector molecule, to the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof; (e) a proteinase inhibitor, and (f) a cytokine. In a specific method disclosed as an example, and not as a limitation to the present invention, a DNA plasmid vector containing the interleukin-1 beta (IL-1β) coding sequence was ligated downstream of the cytomegalovirus (CMV) promoter. This DNA plasmid construction was encapsulated within liposomes and injected intraarticularly into the knee joints of recipient rabbits. IL-1β was expressed and significant amounts of interleukin-1 beta was recovered from the synovial tissue. An alternative is injection of the naked plasmid DNA into the knee joint, allowing direct transfection of the DNA into the synovial tissue. Injection of IL-1β into the joint of a mammalian host allows for prolonged study of various joint pathologies and systemic indices of inflammation, as described within this specification.

Another embodiment of this invention provides a method for introducing at least one gene encoding a product into at least one cell of a connective tissue of a mammalian host for use in treating the mammalian host. This method includes employing non-viral means for introducing the gene encoding for the product into the connective tissue cell. More specifically, this method includes employing non-viral means which is selected from at least one of the group which includes (a) at least one liposome, (b) $Ca_3(PO_4)_2$, (c) electroporation, and (d) DEAE-dextran, and includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof; (e) a proteinase inhibitor, and (f) a cytokine.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a psuedovirus, the genome having been altered such that the psuedovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof, (e) a proteinase inhibitor, and (f) a cytokine.

A further embodiment of this invention provides for an animal model to study connective tissue pathologies and indices of systemic inflammation. This model utilizes either ex vivo or in vivo delivery of at least one gene or DNA sequence of interest encoding a product into a least one cell of a connective tissue of a mammalian host. Examples of joint pathologies which can be studied in the present invention include, but are by no means limited to, joint pathologies such as leukocytosis, synovitis, cartilage breakdown and suppression of cartilage matrix synthesis. Examples of indices of systemic inflammation which include, but are by no means limited to, erythrocyte sedimentation rate, fever and weight loss.

An embodiment of the present invention is a method to produce an animal model for the study of joint pathologies. This embodiment comprises generating a recombinant viral vector which contains a DNA sequence encoding a protein or biologically active fragment thereof, infecting a population of in vitro cultured connective tissue cells with said recombinant viral vector, resulting in a population of transfected connective cells, and transplanting said transfected connective cells to a joint space of a mammalian host. This method will allow for collection of data regarding the effect of various expressed proteins or protein fragment on various deleterious joint pathologies or indicia of inflammation normally associated with a connective tissue disorder.

The connective tissue cells from this embodiment are also selected from the group of connective tissue consisting of a synovium, a cartilage, a tendon and a ligament, preferably synovial cells, including but not limited to autologous cells removed directly from the mammalian host of which the target joint resides.

A preferable mode of introducing transduced synovial cells to the joint space is by intraarticular injection.

A preferable mode of introducing transduced chrondrocyte cells to the area of the targeted cartilage defect is by surgical implantation.

A DNA sequence exemplified for animal model studies is a DNA sequence encoding encoding human IL-1α, human IL-β, or a biologically active fragment thereof.

Another DNA sequence exemplified for animal model studies is a DNA sequence encoding human tumor necrosis factor-a or a biologically active fragment thereof.

Another embodiment of a method to produce an animal model for the study of joint pathologies utilizes a recombinant DNA plasmid vector, which contains the DNA sequence of interest encoding a protein or biologically active fragment thereof. This recombinant DNA plasmid vector is used to transform a population of in vitro cultured connective tissue cells. The transformed connective cells, preferably synovial cells, are transplanted to a joint space of a mammalian host, so as to provide data regarding various joint pathologies and systemic indices of inflammation associated with connective tissue disorders.

This particular embodiment is exemplified by the ex vivo based delivery of MFG-IL-1β to a target rabbit knee joint, causing various joint pathologies and systemic indices of inflammations.

Another exemplification of this particular embodiment of the present invention is delivery of the CMV-IL-1β plasmid construction to the rabbit knee joint via liposome-mediated delivery.

An animal model as described and exemplified in this specification measures the ability of various gene therapy applications disclosed throughout this specification to withstand challenges from known causative agents (such as IL-1β) of joint pathologies and inflammatory side effects.

An additional embodiment of the present invention relates to a method of using a DNA sequence encoding a biologically active interleukin-1 receptor antagonist (IRAP) or portion thereof for treatment of connective tissue joint pathologies. The DNA sequence encoding IRAP or a biologically active fragment thereof may be delivered to the connective tissue of a mammalian host by any combination of various vector strategies and transduction techniques disclosed throughout this specification.

A preferred method of the embodiment of delivering IRAP to a target joint space involves delivery of the IPAP gene to the synovial lining of a mammalian host through use of a retroviral vector with the ex vivo technique disclosed within this specification. In other words, a DNA sequence of interest encoding a functional IRAP protein or protein fragment is subcloned into a retroviral vector of choice, the recombinant viral vector is then grown to adequate titers and used to infect in vitro cultured synovial cells, and the transduced synovial cells, preferably autografted cells, are transplanted into the joint of interest, preferably by intra-articular injection.

Another preferred method of the present invention involves direct in vivo delivery of the IRAP gene to the synovial lining of a mammalian host through use of either an adenovirus vector, adeno-associated virus (AAV) vector or herpes-simples virus (HSV) vector. In other words, a DNA sequence of interest encoding a functional IRAP protein or protein fragment is subcloned into the respective viral vector, the IRAP containing viral vector is then grown to adequate titers and directed into the joint space, preferably by intra-articular injection. A retroviral-IRAP construct, such as MFG-IRAP may also be utilized to directly target previously inflamed connective tissue cells within the joint space.

Direct intra-articular injection of a DNA molecule containing the gene of interest into the joint results in transfection of the recipient synovial cells and hence bypasses the requirement of removal, in vitro culturing, transfection, selection, as well as transplanting the DNA vector containing—synoviocytes (as disclosed in the Example section) to promote stable expression of the heterologous gene of interest. Methods of presenting the DNA molecule to the target connective tissue of the joint includes, but is not limited to, forming a complex of the DNA molecule with cationic liposomes, subcloning the DNA sequence of interest in a retroviral vector as described throughout this specification, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. In vivo delivery of various viral and non-viral vectors to the rabbit knee joint are described in Example XIV.

Another embodiment of the present invention is delivery of a DNA sequence of interest to the connective tissue of a mammalian host by any of the methods disclosed within this specification so as to effect in vivo expression of the human TNF-α soluble receptor or a biologically active fragment thereof.

Another embodiment of the present invention is delivery of a DNA sequence of interest to the connective tissue of a mammalian host by any of the methods disclosed within this specification so as to effect in vivo expression of various cytokines which possess anti-inflammatory and immunomodulatory characteristics, including but by no means limited to interleukin-4, interleukin-10, interleukin-13 and viral interleukin-10 (vIL-10).

Another embodiment of the present invention is delivery of a DNA sequence of interest to the connective tissue of a mammalian host by any of the methods disclosed within this specification so as to effect in vivo expression of various antiadhesion molecules so as to inhibit cell-cell and cell-matrix interactions. Examples of such proteins or protein fragments include but are not limited to soluble ICAM-1 and soluble CD44.

Another embodiment of the present invention is delivery of a DNA sequence of interest to the connective tissue of a mammalian host by any of the methods disclosed within this specification so as to effect in vivo expression of various cartilage growth factors, including but not limited to IGF-1, TGF-$β_1$, TGF-$β_2$, and TGF-$β_3$.

Another embodiment of the present invention is delivery of a DNA sequence of interest to the connective tissue of a mammalian host by any of the methods disclosed within this specification so as to effect in vivo expression of various free radical antagonists, thus preventing the deleterious effects of free radical formation within the afflicted joint. Examples include but are not limited to the superoxide dismutase and proteins or protein fragments which inhibit NO.

Another embodiment of the present invention regarding delivery of the IRAP gene to the synovial lining of a mammalian host involves use subcloning this DNA sequence of interest into a viral vector such as adenovirus, adeno-associated virus and herpes-simplex virus. The respective recombinant IRAP based viral vector is then delivered to the joint by direct in vivo injection so as to effect in vivo expression of the IRAP protein or biologically active fragment thereof.

Another embodiment of this invention provides a method of using the gene encoding an extracellular interleukin-1 binding domain of the interleukin-1 receptor. This gene is capable of binding to and neutralizing interleukin-1 in vivo to substantially resist the degradation of cartilage in a mammalian host. Unlike previous pharmacological efforts, the method of this invention employs gene therapy in vivo to address the chronic debilitating effects of arthritis.

A preferred method of using the gene coding for the truncated interleukin-1 receptor of this invention involves employing recombinant techniques to generate a cell line which produces infectious retroviral particles containing the gene coding for the truncated interleukin-1 receptor. The producer cell line is generated by inserting the gene coding into a retroviral vector under the regulation of a suitable eukaryotic promoter, transfecting the retroviral vector containing the gene coding into the retroviral packaging cell line for the production of a viral particle that is capable of expressing the gene coding for the truncated interleukin-1 receptor, and infecting the synovial cells of a mammalian host using the viral particle.

More specifically, the method of using the hereinbefore described gene coding for the truncated interleukin-1 receptor involves introducing the viral particles obtained from the retroviral packaging cell line directly by intra-articular injection into a joint space of a mammalian host that is lined with synovial cells. In a preferred embodiment, synoviocytes recovered from the knee joint are cultured in vitro for subsequent utilization as a delivery system for gene therapy. It will be apparent that Applicants are not limited to the use of the specific synovial tissue disclosed. It would be possible to utilize other tissue sources, such as skin cells, for in vitro culture techniques. The method of using the gene of this invention may be employed both prophylactically and in the therapeutic treatment of arthritis. It will also be apparent that Applicants are not limited to prophylactic or therapeutic applications in treating only the knee joint. It would be possible to utilize the present invention either prophylactically or therapeutically to treat arthritis in any susceptible joint.

In another embodiment of this invention, a method of using the hereinbefore described gene coding for the truncated interleukin-1 receptor involves infecting synovial cells in culture with the viral particles and subsequently transplanting the infected synovial cells back into the joint. This method of using the gene of this invention may also be employed prophylactically and in the therapeutic treatment of arthritis in any area susceptible to the disorder.

In another embodiment of this invention, a method of using the gene coding for an extracellular interleukin-1 binding domain of the interleukin-1 receptor that is capable of binding to and neutralizing interleukin-1 includes employing recombinant techniques to produce a retrovirus vector carrying two genes. The first gene encodes the extracellular interleukin-1 binding domain of the interleukin receptor, and the second gene encodes for selectable antibiotic resistance. This method of use involves transfecting the retrovirus vector into a retrovirus packaging cell line to obtain a cell line producing infectious retroviral particles carrying the gene.

Another embodiment of this invention provides a method of preparing a gene encoding an extracellular interleukin-1 binding domain of the interleukin-1 receptor including synthesizing the gene by a polymerase chain reaction, introducing the amplified interleukin-1 receptor coding sequence into a retroviral vector, transfecting the retroviral vector into a retrovirus packaging cell line and collecting viral particles from the retrovirus packaging cell line.

In another embodiment of this invention, a compound for parenteral administration to a patient in a therapeutically effective amount is provided for that contains a gene encoding an extracellular interleukin-1 binding domain of the interleukin-1 receptor and a suitable pharmaceutical carrier.

Another embodiment of this invention provides for a compound for parenteral administration to a patient in a prophylactically effective amount that includes a gene encoding an extracellular interleukin-1 binding domain of the interleukin-1 receptor and a suitable pharmaceutical carrier.

An additional embodiment of the invention involves transfection of hematopoietic progenitor cells or mature lymphoid or myeloid cells with a DNA vector molecule containing any of the gene or genes disclosed throughout the specification. The transfected cells are recovered and injected into the bone marrow marrow or peripheral bloodstream of the patient using techniques known to the skilled artisan. It will be possible, within the scope of this method, to use cells derived from donor bone marrow instead of cells derived from recipient bone marrow so as to modify rejection.

The present invention also relates to methods of using various DNA sequences disclosed throughout this specification to provide therapeutic treatment for damaged cartilage, particularly damaged articular cartilage, such as articular cartilage within the human knee joint. For example, the present invention provides for methods of treating damaged or defective articular cartilage by introducing a DNA sequence into chondrocytes whereby expression of the DNA sequence of interest in vivo provides therapeutic relief from cartilage defects.

The present invention provides gene therapy methods for delivery of DNA sequences of interest to chondrocyte cells cultured in vitro and transplantation of these transfected cells to the damaged articular cartilage within a mammalian host. Such DNA sequences which are utilized express proteins or biologically active fragments thereof which improve or maintain chondrogenesis. Viral promoters active in eukaryotic cells, as well as the mixing and matching of these promoter and additional enhancer sequences may be utilized in practicing the claimed invention. Also, promoters useful in plasmid constructions, including but not limited to a cytomegalovirus (CMV) promoter, a Rous Sarcoma virus (RSV) promoter, a Murine Leukemia Virus (MLV) promoter, a β-actin promoter, as well as any cell-specific eukaryotic promoter sequence that would be known to be active in the cell targeted for transduction. As an alternative, the present invention provides for use of alternative promoters, e.g., strong chondrocyte promoters such as the type II collagen gene promoter. Additionally, the present invention allows for use of inducible promoters, including but not limited to inducible promoters regulating expression of IL-1, IL-6 and IL-8. Any eukaryotic promoter and/or enhancer sequence available to the skilled artisan which is known to control expression of the nucleic acid of interest may be used in either a viral or plasmid vector construction. As mentioned above, other promoters and vector constructs may be utilized to either shorten or lengthen the duration of in vivo expression within the transplanted chondrocyte/scaffold matrix.

In a specific embodiment of the present invention, a method of treating a mammalian cartilage defect is disclosed which comprises generating a recombinant viral vector containing a DNA sequence expressing a protein or biologically active fragment thereof, infecting a population of in vitro cultured chondrocyte cells with the recombinant viral vector so as to generate a population of transfected chondrocyte cells. These transfected chondrocyte cells are then transplanted to the joint area containing the damaged articular cartilage where expression of the recombinant DNA sequence provides therapeutic relief.

In a preferred embodiment of the present invention, the chondrocyte cells retrieved for in vitro culture prior to transfection and transplantation are autologous cells.

In a particular embodiment of the present invention, cultures of articular chondrocytes to be used for allotransplantation are either transduced with the recombinant viral or plasmid DNA vector and selected with G418. Confluent monolayers of chondrocytes are harvested washed, and counted. These chondrocytes are added to a collagen solution, which is allowed to gel prior to transplantation. The chondrocytelcollagen mixture is adhered to the damaged region of articular cartilage with fibrin glue, a mixture of fibrinogen and thrombin.

Any of the vector and/or genes disclosed throughout this specification possess the potential for therapeutic use in chondrocyte-based applications. Additionally, any such vectors and/or gene disclosed within the specification may be used in a model animal system to monitor, for example, localized effects of continuous cytokine expression in cartilage formation and rehabilitation. Such preferred vectors include, but are not limited to, a retroviral vector, such as MFG or BAG, and any plasmid DNA construct as disclosed throughout this specification. Preferred genes of biologically active gene fragments include but are not limited to human transforming growth factor-$\beta_1$ (TGF-$\beta_1$), human transforming growth factor-$\beta_2$ (TGF-$\beta_2$), human transforming growth factor-$\beta_3$ (TGF-$\beta_3$), insulin-like growth factor-1 (IGF-1), bone morphogenetic proteins (BMPs), IRAP and the extracellular domain of the interleulin-1 receptor protein.

Another preferred method of the present invention involves non-viral based delivery of the DNA sequence of interest to the in vitro cultured, preferably utilizing a plasmid DNA vector, as discussed within this specification. Therefore, the invention also provides for treatment of a mammalian cartilage defect which comprises generating a recombinant plasmid DNA vector which contains a DNA sequence encoding a protein or biologically active fragment thereof, infecting a population of in vitro cultured chondrocyte cells with the recombinant viral vector so as to generate a population of transfected chondrocyte cells. These transfected chondrocyte cells are then transplanted to the joint area containing the damaged articular cartilage where expression of the recombinant DNA sequence provides therapeutic.

To this end, as discussed throughout this specification, the present invention also provides for the use of non-viral mediated delivery systems to chondrocytes cultured in vitro, including, but not limited to (a) direct injection of naked DNA; (b) liposome mediated transduction; (c) calcium phosphate [$Ca_3(PO_4)_2$] mediated cell transfection, the genetically transformed cells then returned extraarticularly to the mammalian host; (d) mammalian host cell transfection by electroporation, the genetically transformed cells then returned extraarticularly to the mammalian host; (e) DEAE-dextran mediated cell transfection, the genetically transformed cells then returned extraarticularly to the mammalian host; (f) polybrene mediated delivery; (g) protoplast fusion; (h) microinjection; and (i) polylysine mediated transformation.

The specification enables gene delivery and expression to both synovial cells and chondrocyte cells, each a respective connective tissue. The advantages of both direct in vivo and ex vivo methods of delivery are described in this specification. To this end, the present invention also teaches a combinatorial use of synovial and chondrocyte cell delivery methods which provide prophylactic or therapeutic relief from various joint pathologies enumerated throughout the specification.

One or more distinct DNA sequences can be delivered to the effected joint or joints by using a strategy whereby multiple DNA sequences, each housed within an appropriate recombinant vector, is transferred to chondrocyte cells and/or synovial cells by the methods disclosed throughout the specification. It is then possible to deliver gene or gene fragment combinations which will promote either a prophylactic or therapeutic response in vivo.

It is preferred that the ex vivo method described above for gene transfer to chondrocytes be utilized in conjunction with ex vivo method of gene transfer to synovial cells.

It is also preferred that the ex vivo method described above for gene transfer to chondrocytes be utilized in conjunction with direct ex vivo method of gene transfer to synovial cells.

Therefore, a method of treating a human full-thickness mammalian cartilage defect is disclosed which involves infecting a population of in vitro cultured autologous chondrocyte cells with at least a first recombinant viral vector containing a DNA sequence encoding a protein or biologically active fragment which results in a population of transfected chondrocyte cells, infecting a population of in vitro cultured autologous synovial cells with at least a second recombinant viral vector containing a DNA sequence encoding a protein or biologically active fragment which results in a population of transfected synovial cells, and transplanting the transfected chondrocyte cells and synovial cells to the appropriate joint space as described throughout this specification such that subsequent expression the recombinant proteins within the targeted joint space substantially alleviates the cartilage defect.

In a preferred embodiment of dual gene transfer delivery methods, the transfected synovial cells are introduced into the joint space by intra-articular injection.

In a preferred embodiment of dual gene transfer, one DNA sequence is subcloned into a recombinant vector and targeted to the joint space by synovial cell transfection and intra-articular injection, wherein a second DNA sequence is subcloned into a recombinant vector in a second procedure and targeted to the area of damaged articular cartilage.

The methods of the present invention are tailored primarily for treatment of genetic based connective tissue diseases or disorders. However, it will be known upon review of this specification that the methods of the present invention may also be utilized for treating injuries of the type encountered by sports medicine orthopaedists.

It is an object of the present invention to provide a method of introducing at least one gene encoding a product into at least one cell of a connective tissue of a mammalian host for use in treating the mammalian host.

It is an object of the invention to provide a method of introducing a gene encoding a product into at least one cell of a connective tissue of a mammalian host for a therapeutic use.

It is an object of the present invention to provide a method of introducing into the synovial lining cells of a mammalian arthritic joint at least one gene which codes for proteins having therapeutic properties.

It is an object of the present invention to provide an animal model for the study of connective tissue pathology.

It is an object of the present invention to provide a method of using in vivo a gene coding for the extracellular interleukin-1 binding domain of the interleukin-1 receptor that is capable of binding to and neutralizing substantially all isoforms of interleukin-1, including interleukin-1 alpha and interleukin-1 beta.

It is an object of the present invention to provide a method of using in vivo a gene coding for IRAP or a biologically active derivative thereof which is a competitive inhibitor of and therefore substantially neutralizes all isoforms of interleukin-1, including interleukin-1 alpha and interleukin-1 beta.

It is an object of the present invention to provide a method of using a gene in vivo in a mammalian host that is capable of binding to and neutralizing substantially all isoforms of interleukin-1 and thus, substantially resist the degradation of cartilage and protect surrounding soft tissues of the joint space.

It is an object of the present invention to provide a method of using in vivo a gene coding for the extracellular interleukin-1 binding domain of the interleukin-1 receptor that is capable of binding to and neutralizing substantially all isoforms of interleukin-1 for the prevention of arthritis in patients that demonstrate a high susceptibility for developing the disease.

It is an object of the present invention to provide a method of using in vivo a gene coding for IRAP that is capable of acting as a competitive inhibitor of and therefore substantially neutralizes all isoforms of interleukin-1 for the prevention of arthritis in patients that demonstrate a high susceptibility for developing the disease.

It is an object of the present invention to provide a method of using in vivo a gene coding for an extracellular interleukin-1 binding domain of an interleukin-1 receptor that is capable of binding to and neutralizing substantially all isoforms of interleukin-1 for the treatment of patients with arthritis.

It is an object of the present invention to provide a method of using in vivo a gene coding for IRAP or a biologically active derivative thereof which is a competitive inhibitor of and therefore substantially neutralizes all isoforms of interleukin-1 for the treatment of patients with arthritis.

It is an object of the present invention to provide a method of using in vivo a gene or genes that address the chronic debilitating pathophysiology of arthritis.

It is a further object of the present invention to provide a compound for parenteral administration to a patient which comprises a gene encoding an extracellular interleukin-1 binding domain of the interleukin-1 receptor and a suitable pharmaceutical carrier.

It is a further object of the present invention to provide a compound for parenteral administration to a patient which comprises a gene encoding IRAP and a suitable pharmaceutical carrier.

It is an object of the present invention to provide a gene therapy based method of treating articular cartilage defects which involves transfecting cultured chondrocytes with a recombinant vector expressing a protein or protein fragment and transplanting these genetically modified chondrocytes to the location of the articular cartilage defect.

It is also an object of the present invention to utilize gene transfer to both synovial cells and chondrocyte cells and the subsequent methods of joint space delivery to treat the identical malady.

It is also an object of the present invention to utilize the chondrocyte-based methods of gene transfer methods described in this specification for use in animal models.

These and other objects of the invention will be more fully understood from the following description of the invention, the referenced drawings attached hereto and the claims appended hereto.

BRIEF DESCRIPTION OF THE DRAWINGS

FIGS. 8A–8C show the amino acid and nucleotide sequence of the human (SEQ ID NOS 1 and 2) and mouse (SEQ ID NOS 3 and 4) interleukin-1 receptors.

DETAILED DESCRIPTION OF THE INVENTION

Figure 1:
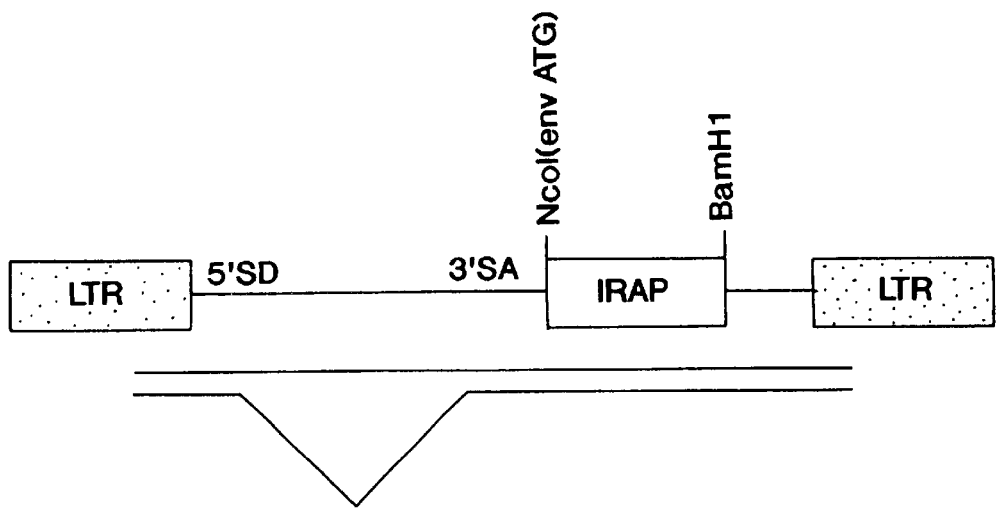
FIG. 1 shows the structure of the cDNA encoding the human interleukin-1 receptor antagonist protein (IRAP) gene inserted into the NcoI and BamHI cloning sites of the retroviral vector MFG.

As used herein, the term "patient" includes members of the animal kingdom including but not limited to human beings.

As used herein, the term "mammalian host" includes members of the animal kingdom including but not limited to human beings.

As used herein, the term "connective tissue" includes but is not limited to a ligament, a cartilage, a tendon, and a synovium of a mammalian host.

As used herein, the term "DC-chol" means a cationic liposome containing cationic cholesterol derivatives. The "DC-chol" molecule includes a tertiary amino group, a medium length spacer arm (two atoms) and a carbamyol linker bond as described in *Biochem. Biophys. Res. Commun.*, 179:280–285 (1991), X. Gao and L. Huang.

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of joints provides direct access to a joint. However, most of the injected drugs have a short intra-articular half-life. The present invention solves these problems by introducing into the connective tissue of a mammalian host genes encoding for proteins that may be used to treat the mammalian host. More specifically, this invention provides a method for introducing into the connective tissue of a mammalian host genes encoding for proteins with anti-arthritic properties.

The present invention provides a method of introducing at least one gene encoding a product into at least one cell of a connective tissue of a mammalian host for use in treating the mammalian host which comprises employing recombinant techniques to produce a viral vector which contains the gene encoding for the product, and infecting the connective tissue cell of the mammalian host using the viral vector containing the gene coding for the product. This method preferably includes introducing the gene encoding the product into at least one cell of the connective tissue of the mammalian host for a therapeutic use.

One ex vivo method of treating a connective tissue disorder disclosed throughout this specification comprises initially generating a recombinant viral vector which contains a DNA sequence encoding a protein or biologically active fragment thereof. This recombinant viral vector is then used to infect a population of in vitro cultured connective tissue cells, resulting in a population of transfected connective cells. These transfected connective tissue cell are then transplanted to connective tissue within a target joint space of a mammalian host, effecting subsequent expression of the protein or protein fragment within the joint space. Expression of this DNA sequence of interest is useful in substantially reducing at least one deleterious joint pathology or indicia of inflammation normally associated with a connective tissue disorder.

The connective tissue cells are selected from the group of connective tissue consisting of a synovium, a cartilage, a tendon and a ligament, preferably synovial cells.

It is also preferred that a retroviral vector, such as MFG, be utilized as the viral vector.

A preferable mode of introducing transduced synovial cells to the joint space is by intraarticular injection.

A preferable mode of introducing transduced chrondrocyte cells to the area of the targeted cartilage defect is by surgical implantation.

It will be understood by the artisan of ordinary skill that the preferred source of cells for treating a human patient are the patients own cells, such as autologous synovial cells.

In a preferred embodiment of this invention, the method as hereinbefore described includes employing as the gene a DNA sequence encoding a human interleukin-1 receptor antagonist protein (IRAP) or biologically active fragment thereof.

Therefore, a preferred embodiment of the present invention relates to a method of using a DNA sequence encoding a biologically active interleukin-1 receptor antagonist (IRAP) or portion thereof for treatment of connective tissue joint pathologies. The DNA sequence encoding IRAP or a biologically active fragment thereof may be delivered to the connective tissue of a mammalian host by any combination of various vector strategies and transduction techniques disclosed throughout this specification.

A preferred method of the embodiment of delivering IRAP to a target joint space involves delivery of the IRAP gene to the synovial lining of a mammalian host through use of a retroviral vector with the ex vivo technique disclosed within this specification. In other words, a DNA sequence of interest encoding a functional IRAP protein or protein fragment is subcloned into a retroviral vector of choice, the recombinant viral vector is then grown to adequate titers and used to infect in vitro cultured synovial cells, and the transduced synovial cells, preferably autografted cells, are transplanted into the joint of interest, preferably by intraarticular injection.

In another embodiment of this invention, the method as hereinbefore described includes employing as the gene a gene capable of encoding a soluble interleukin-1 receptor.

In another embodiment of this invention, the method as hereinbefore described includes employing as the gene a gene capable of encoding a soluble TNF-α receptor.

Another embodiment of this invention includes the method as hereinbefore described including employing as the gene a gene capable of encoding at least one proteinase inhibitor. More specifically, this method preferably includes employing a tissue inhibitor of a metalloproteinases as the proteinase inhibitor.

Another embodiment of this invention includes the method as hereinbefore described including employing as the gene a gene capable of encoding at least one cytokine. More specifically, this method includes employing as the cytokine at least one material selected from the group consisting of interleukin-1 alpha (IL-1α), interleukin-1 beta (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), viral interleukin-10 (vIL-10), interleukin-11 (IL-1), interleukin-12 (IL-12), interleukin-13 (IL-13), interleukin-14 (IL-14), interleukin-15 (IL-15), especially interleukin-13 (IL-13), tumor necrosis factor-α (TNF-α), and tumor necrosis factor-β (TNF-β).

A further embodiment of this invention includes a method as hereinbefore described including employing as the cytokine at least one transforming growth factor. More specifically, this method includes employing as the transforming growth factor a growth factor selected from the group consisting of TGF-beta$_1$, TGF-beta$_2$, TGF-beta$_3$, and TGF-alpha. Each transforming growth factor is commercially available from R & D Systems, 614 McKinley Place, N.E., Minneapolis, Minn. 55413.

In another embodiment of this invention, the method as hereinbefore described includes employing as the cytokine at least one fibroblast growth factor. The fibroblast growth factors are also commercially available from R & D Systems, 614 McKinley Place, N.E., Minneapolis, Minn. 55413.

Another embodiment of this invention includes the method as hereinbefore described including employing as the viral vector a retroviral vector. More specifically, this method includes employing as the retroviral vector at least one material selected from the group consisting of MFG and BAG. A preferred embodiment of this invention includes providing the method as hereinbefore described including employing as the gene a gene capable of encoding a human interleukin-1 receptor antagonist protein and employing MFG as the retroviral vector.

Another preferred embodiment of this invention includes the method as hereinbefore described including employing a Lac Z marker gene as the gene capable of encoding a beta-galactosidase and employing MFG as the retroviral vector.

Another preferred embodiment of this invention provides the method as hereinbefore described including employing a Lac Z neo marker gene as the gene capable of encoding a beta-galactosidase and employing BAG as the retroviral vector.

In a most preferred embodiment of this invention, the method as hereinbefore described includes employing a retroviral vector selected from the group consisting of MFG and BAG and includes employing as the gene a gene capable of encoding a soluble interleukin-1 receptor.

In another embodiment of this invention, a method as hereinbefore described is provided including employing as the gene a gene capable of encoding at least one proteinase inhibitor and including employing as the retroviral vector at least one material selected from the group consisting of MFG and BAG.

In another embodiment of this invention, a method as hereinbefore described is provided which includes employing as the retroviral vector at least one material selected from the group consisting of MFG and BAG and including employing as the gene a gene capable of encoding at least one cytokine as hereinbefore described.

In another embodiment of this invention, a method is provided for introducing at least one gene encoding a product into at least one cell of a connective tissue of a mammalian host for use in treating the mammalian host which comprises employing recombinant techniques to produce a viral vector which contains the gene encoding for the product and infecting the connective tissue cell of the mammalian host using the viral vector containing the gene coding for the product, wherein the viral vector is at least one vector selected from the group consisting of an adeno-associated virus, an adenovirus, and a herpes virus, such as herpes simplex type-1 or herpes simplex type-2. This method includes employing as the gene a gene capable of encoding at least one material selected from the group which includes (a) a human interleukin-1 receptor antagonist protein, (b) a soluble interleukin-1 receptor, (c) a Lac Z marker gene capable of encoding a beta-galactosidase, (d) at least one proteinase inhibitor and (e) at least one cytokine. More specifically, this method includes employing a tissue inhibitor of metalloproteinases as the proteinase inhibitor and includes employing as the cytokine at least one of the materials selected from the group which includes (a) at least one transforming growth factor selected from the group consisting of TGF-beta$_1$, TGF-beta$_2$, TGF-beta$_3$, and TGF-alpha, (b) at least one fibroblast growth factor, (c) IL-1α, (d) IL-1β, (e) IL-2 (f) IL-3, (g) IL-4, (h) IL-5, (i) IL-6(j) IL-7, (k) IL-8, (l) IL-9, (m) IL-10, (n) IL-11, (o) IL-12, (p) IL-13, (q) IL-14, (r) IL-15, (s) vIL-10, (t) TNF-α, and (u) TNF-β.

Another embodiment of this invention includes the method as hereinbefore described including introducing the gene into a connective tissue which tissue is selected from the group consisting of a ligament, a cartilage, a tendon, and a synovium. It is preferable that this method includes employing a cruciate ligament as the ligament. Most preferable this method includes employing as the cruciate ligament a ligament selected from the group consisting of an anterior cruciate ligament and a posterior cruciate ligament.

Another embodiment of this invention includes the method as hereinbefore described including employing as the gene a gene having DNA that is capable of maintenance and expression.

A further embodiment of this invention includes the method as hereinbefore described including introducing the gene into the cell in vitro. This method includes subsequently transplanting the infected cell into the mammalian host. This method also includes after effecting the infecting of the connective tissue cell but before the transplanting of the infected cell into the mammalian host, storing the infected connective tissue cell. It will be appreciated by those skilled in the art that the infected connective tissue cell may be stored frozen in 10 percent DMSO in liquid nitrogen. This method includes employing a method to substantially prevent the development of arthritis in a mammalian host having a high susceptibility of developing arthritis.

The method of this invention includes employing the method on an arthritic mammalian host for a therapeutic use. This method includes employing a method to repair and regenerate the connective tissue which tissue is selected from the group consisting of a ligament, a cartilage, a tendon, and a synovium. This method includes employing the method on a mammalian host that is a human being.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. This method includes employing the method to substantially prevent a development of arthritis in a mammalian host having a high susceptibility of developing arthritis. This method also includes employing the method on an arthritic mammalian host for therapeutic use. Further this method as includes employing the method to repair and regenerate the connective tissue as hereinbefore defined.

In yet another embodiment of this invention, a method of introducing at least one gene encoding a product into at least one cell of a connective tissue of a mammalian host for use in treating the mammalian host includes employing non-viral means for introducing the gene encoding for the product into the connective tissue cell. This method includes employing non-viral means selected from the group consisting of at least one liposome, $Ca_3(PO_4)_2$, electroporation, and DEAE-dextran. This method includes employing as the liposome a material selected from the group consisting of DC-chol and SF-chol.

It will be understood that the method of this invention of introducing at least one gene encoding a product into at least one cell of a connective tissue of a mammalian host for use in treating the mammalian host that includes employing non-viral means for introducing the gene encoding for the product into the connective tissue cell is a non-infectious delivery system. An advantage of the use of a non-infectious delivery system is the elimination of insertional mutagenesis (potentially a problem for retroviral applications) and virally induced disease.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding at least one of the following materials selected from the group which includes (a) a human interleukin-1 receptor antagonist protein, (b) a Lac Z marker gene capable of encoding a beta-galactosidase, (c) a soluble interleukin-1 receptor, (d) at least one proteinase inhibitor, (e) at least one transforming growth factor, and (f) at least one cytokine. More specifically, this method includes employing as the cytokine a cytokine selected from the group which includes IL-1α, IL-1β, IL-2, IL-3, IL-4, IL-5, IL-6, IL-7, IL-8, IL-9, IL-10, IL-11, IL-12, TNF-α, and TNF-β, and at least one fibroblast growth factor. Preferably, IL-4, IL-10, and IL-13 are the selected cytokines. Preferably, this method includes employing as the transforming growth factor a growth factor selected from the group consisting of TGF-beta$_1$, TGF-beta$_2$, TGF-beta$_3$, and TGF-alpha.

High levels of collagenase and other tissue metalloproteinases, such as stromelysin and gelatinase can be expressed in the presence of IL-1 within connective tissue. Collagenase, stromelysin, and gelatinase are inhibited by the protein TIMP ("Tissue Inhibitor of MetalloProteinases"; TIMP-1, TIMP-2 or TIMP-3). Therefore, another preferred embodiment of this invention includes providing the method employing non-viral means as hereinbefore described which includes employing a tissue inhibitor of metalloproteinases (TIMP) as the proteinase inhibitor. This method employing non-viral means for introducing the gene encoding for the product into the connective tissue cell as hereinbefore described includes introducing the gene into the connective tissue which tissue is selected from the group consisting of a ligament, a cartilage, a tendon, and a synovium. Preferably, this method includes employing a cruciate ligament as the ligament. The cruciate ligament is selected from the group consisting of an anterior cruciate ligament and an posterior cruciate ligament. Of course, a gene encoding a TIMP protein or biologically active fragment thereof could be delivered to the target connective tissue by any combination of means disclosed in this specification.

Another embodiment of the present invention is delivery of a DNA sequence of interest to the connective tissue of a mammalian host by any of the methods disclosed within this specification so as to effect in vivo expression of various antiadhesion molecules so as to inhibit cell-cell and cell-matrix interactions. Examples of such proteins or protein fragments include but are not limited to soluble ICAM-1 and soluble CD44.

Another embodiment of the present invention is delivery of a DNA sequence of interest to the connective tissue of a mammalian host by any of the methods disclosed within this specification so as to effect in vivo expression of various cartilage growth factors, including but not limited to IGF-1 and TGF-$\beta$.

Another embodiment of the present invention is delivery of a DNA sequence of interest to the connective tissue of a mammalian host by any of the methods disclosed within this specification so as to effect in vivo expression of various free radical antagonists, thus preventing the deleterious effects of free radical formation within the afflicted joint. Examples include but are not limited to the superoxide dismutase and proteins or protein fragments which inhibit NO.

A further embodiment of this invention provides for an animal model to study connective tissue pathologies and indices of systemic inflammation. This model utilizes either ex vivo or in vivo delivery of at least one gene or DNA sequence of interest encoding a product into a least one cell of a connective tissue of a mammalian host. Examples of joint pathologies which can be studied in the present invention include, but are by no means limited to, joint pathologies such as leukocytosis, synovitis, cartilage breakdown and suppression of cartilage matrix synthesis. Examples of indices of systemic inflammation which include, but are by no means limited to, erythrocyte sedimentation rate, fever and weight loss.

A particular embodiment of the present invention which relates to such an animal model is utilization of the ex vivo based delivery of a DNA sequence encoding human IL-1$\beta$ gene to the synovial lining of the rabbit knee. In this embodiment, the human IL-1$\beta$ gene was subcloned into the MFG retroviral vector by known methods, resulting in MFG-IL-1$\beta$. This recombinant retroviral construct was used to transduce autologous synovial cells cultured in vitro. These transduced cells were then delivered to the rabbit knees as described throughout this specification. Delivery of the human IL-1$\beta$ gene to the synovial lining of the rabbit knee in this fashion caused a sever, chronic, monarticular arthritis. Pathologies included leukocytosis, synovitis, cartilage breakdown and suppression of cartilage matrix synthesis. Various systemic indices of inflammation were also effected, including an increased erythrocyte sedimentation rate, fever and weight loss.

In another example of this particular embodiment of the present invention, the human IL-1$\beta$ gene was subcloned into a DNA plasmid vector, downstream of a CMV promoter. This CMV-IL-1$\beta$ plasmid construct was encapsulated in liposomes and delivered to a target joint space as described in Example X. Forty eight hours subsequent to injection 1 ng of IL-1$\beta$ was recovered from the knee joint area.

An animal model as described and exemplified in this specification measures the ability of various gene therapy applications disclosed throughout this specification to withstand challenges from known causative agents (such as IL-1$\beta$) of joint pathologies and inflammatory side effects.

Another preferred method of the present invention involves direct in vivo delivery of the IRAP gene to the synovial lining of a mammalian host through use of either an adenovirus vector, adeno-associated virus (AAV) vector or herpes-simples virus (HSV) vector. In other words, a DNA sequence of interest encoding a functional IPAP protein or protein fragment is subcloned into the respective viral vector, the IRAP containing viral vector is then grown to adequate titers and directed into the joint space, preferably by intra-articular injection. A retroviral-IRAP construct, such as MFG-IRAP may also be utilized to directly target previously inflamed connective tissue cells within the joint space.

Direct intra-articular injection of a DNA molecule containing the gene of interest into the joint results in transfection of the recipient synovial cells and hence bypasses the requirement of removal, in vitro culturing, transfection, selection, as well as transplanting the DNA vector containing—synoviocytes (as disclosed in the Example section) to promote stable expression of the heterologous gene of interest. Methods of presenting the DNA molecule to the target connective tissue of the joint includes, but is not limited to, formation of a complex of the DNA molecule with cationic liposomes, subcloning the DNA sequence of interest in a retroviral vector as described throughout this specification, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. In vivo delivery of various viral and non-viral vectors to the rabbit knee joint are described in Example XV.

Another embodiment of this invention provides the method of introducing at least one gene encoding a product into at least one cell of a connective tissue of a mammalian host for use in treating the mammalian host which includes employing non-viral means as hereinbefore described and includes employing as the gene a gene having DNA that is capable of maintenance and expression.

In yet a further embodiment of this invention, the method of introducing at least one gene encoding a product into at least one cell of a connective tissue of a mammalian host for use in treating the mammalian host is provided that includes employing non-viral means for introducing the gene encoding for the product into the connective tissue cell in vitro and includes subsequently transplanting the cell having the gene into the mammalian host. Another embodiment of this invention provides a method including after introducing the gene encoding for the product in the connective tissue cell and before the transplanting of the connective tissue cell having the gene into the mammalian host, storing the connective tissue cell having the gene. This method includes storing connective tissue cell frozen in 10 percent DMSO in liquid nitrogen. This method includes employing a method to substantially prevent the development of arthritis in a mammalian host having a high susceptibility of developing arthritis. Further, this method includes employing the method on an arthritic mammalian host for a therapeutic use. This method includes employing the method to repair and regenerate the connective tissue which tissue is selected from the group consisting of a ligament, a cartilage, a tendon, and a synovium.

A further embodiment of this invention provides a method of introducing at least one gene encoding a product into at least one cell of a connective tissue of a mammalian host for use in treating the mammalian host which includes employing non-viral means in vivo for directly introducing the gene encoding for the product into the connective tissue cell of the mammalian host. The non-viral means is selected from the group consisting of at least one liposome, $Ca_3(PO_4)_2$ and DEAE-dextran. Preferably, this method includes effecting the in vivo introduction into the mammalian host by intra-articular injection. This method includes employing the method to substantially prevent the development of arthritis in a mammalian host having a high susceptibility of developing arthritis. Further, this method includes employing the method on an arthritic mammalian host for a therapeutic use. This method also includes employing the method to repair and regenerate the connective tissue which tissue is selected from the group consisting of a ligament, a cartilage, a tendon, and a synovium.

Another embodiment of the present invention is a method to produce an animal model for the study of connective tissue pathology. As will be understood by those skilled in the art, over-expression of interleukin-1 in the joint of a mammalian host is generally responsible for the induction of an arthritic condition. This invention provides a method for producing an animal model using the hereinbefore described gene transfer technology of this invention. Preferably, the method of this invention provides a method for producing an animal model using the hereinbefore described gene transfer technology of this invention to effect an animal model for arthritis. For example, constitutive expression of interleukin-1 in the joint of a rabbit following the method of gene transfer provided for by this invention leads to the onset of an arthritic condition. It will be appreciated by those skilled in the art that this rabbit model is suitable for use for the testing of therapeutic agents. This method includes introducing at least one gene encoding a product into at least one cell of a connective tissue of a mammalian host comprising (a) employing recombinant techniques to produce a viral vector which contains the gene encoding for the product and (b) infecting the connective tissue cell of the mammalian host using the viral vector containing the gene coding for the product for effecting the animal model. This method includes employing as the gene a material selected from the group consisting of a cytokine and a proteinase. This method includes employing as the cytokine a material selected from the group consisting of IL-1α, IL-1β and TNF-α. This method includes employing as the proteinase a matrix metalloproteinase. The matrix metalloproteinase is an enzyme selected from the group consisting of a collagenase, a gelatinase and a stromelysin. It will be apparent that use of the term "a collagenase, a gelatinase and a stromelysin" is meant to include the plural, and not be limited to the singular. It is well known in the art that numerous collagenases, gelatinases and stromolysins could be employed as a matrix metalloproteinase in the present invention. A further embodiment of this invention provides a method to produce an animal model for the study of connective tissue pathology which includes employing non-viral means for introducing at least one gene encoding a product into at least one cell of a connective tissue of a mammalian host for effecting the animal model. The non-viral means is selected from the group consisting of at least one liposome, $Ca_3(PO_4)_2$, electroporation, and DEAE-dextran. This method includes employing as the gene a material selected from the group consisting of a cytokine and a proteinase. This method includes employing as the cytokine a material selected from the group consisting of IL-1α, IL-1β and TNF-α. This method also includes employing as the proteinase a matrix metalloproteinase. The matrix metalloproteinase includes an enzyme selected from at least one of the group consisting of a collagenase, a gelatinase, and a stromelysin.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a proteinase inhibitor, (e) a soluble tumor necrosis factor receptor protein or a biologically active derivative or fragment thereof and (f) a cytokine, and employing as the DNA vector any DNA vector, preferably a plasmid or viral vector, known to one of ordinary skill in the art capable of stable maintenance within the targeted cell or tissue upon delivery, regardless of the method of delivery utilized. In one embodiment of the invention, synoviocytes are transfected in vivo subsequent to direct intra-articular injection of a DNA molecule containing the gene of interest into the joint. Transfection of the recipient synovial cells bypasses the requirement of removal, culturing, in vitro transfection, selection and transplanting the DNA vector containing—synoviocytes (as disclosed in the Example section) to promote stable expression of the heterologous gene of interest. Methods of injecting the DNA molecule into the joint includes, but is not limited to, encapsulation of the DNA molecule into cationic liposomes or the direct injection of the DNA molecule itself into the joint. Expression of the heterologous gene of interest subsequent to in vivo transfection of the synovial tissue is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. As an example, and not a limitation, of the present invention, a DNA plasmid vector containing the IL-1β coding sequence ligated downstream of the CMV promoter was encapsulated within liposomes and injected into the knee joints of recipient rabbits. Interleukin-1 beta was expressed in synovial tissue, as significant amounts of interleukin-1 beta was recovered from the synovial tissue within the region of intra-articular injection.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a pseudovirus, the genome having been altered such that the pseudovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor and (e) a soluble tumor necrosis factor receptor protein or a biologically active derivative or fragment thereof and (f) a cytokine.

As noted throughout this specification, the present invention provides methods for introducing at least one DNA sequence of interest encoding a biologically active protein or protein fragment into a connective tissue of a mammalian host so as to treat one or more joint pathologies, especially human joint pathologies.

To this end, methods are herein disclosed for treating various cartilage defects. In a particular embodiment of the invention, methods are disclosed for treating various articular cartilage defects, preferably human full-thickness articular cartilage defects involving knee joints. Articular cartilage covers the articulating surfaces of the long bones within diarthrodial joints. Its molecular structure enables it to withstand compressive and tensile forces, and to rebound following deformation; the co-efficient of friction of cartilage moving against cartilage, is one-fifth of that of ice moving against ice.

Loss of articular cartilage is the major pathological lesion common to all forms of arthritis, and often occurs as a result of trauma. Cartilage destruction compromises the function of the joint and, in advanced cases, can lead to joint failure. In this event, the surgical insertion of a prosthetic joint replacement remains the only recourse.

Articular cartilage is aneural, alymphatic and avascular, and contains a high ratio of matrix to cells. Partly because of this metabolic isolation, it has a very limited capacity for repair. Chondrocyte cells recovered from articular cartilage are able to grow outside the body in cell culture, and to synthesize large amounts of new matrix.

The present invention provides gene therapy methods for delivery of DNA sequences of interest to chondrocyte cells cultured in vitro and transplantation of these transfected cells to the damaged articular cartilage within a mammalian host. Such DNA sequences which are utilized express proteins or biologically active fragments thereof which improve or maintain chondrogenesis.

In a specific embodiment of the present invention, a method of treating a mammalian cartilage defect is disclosed which comprises generating a recombinant viral vector containing a DNA sequence expressing a protein or biologically active fragment thereof, infecting a population of in vitro cultured chondrocyte cells with the recombinant viral vector so as to generate a population of transfected chondrocyte cells. These transfected chondrocyte cells are then transplanted to the joint area containing the damaged articular cartilage where expression of the recombinant DNA sequence provides therapeutic relief.

It is a goal of this portion of the invention to promote expression of transgenes with the potential to promote matrix synthesis, inhibit matrix breakdown, or both, and to maintain the differentiated phenotype of the articular chondrocytes. Therefore, although data disclosed in Example XVI shows that transgene expression in chondrocytes may be transient (see Table III), prolonged high expression of a therapeutic transgene in this model of chondrocyte/collagen gel transplantation to repair full-thickness articular cartilage defects may not be necessary or desirable.

There are two scenarios by which the present invention may impart therapeutic value to the patient. First, the transplanted chondrocytes are the cells which repopulate and repair the defect. Expression of the therapeutic transgene(s) by the transduced transplanted cells would function in an autocrine and paracrine fashion to facilitate expression of the appropriate functional chondrocytic phenotype which would then regenerate new native articular cartilage through the production of type II collagen, matrix proteoglycans, and other matrix components. Second, the transplanted chondrocytes may instead act as a delivery system which locally generates cytokines that promote the production of new matrix by resident articular chondrocytes or by chondrocytic progenitor cells within the subchondral bone marrow. Regardless of whether the transplanted transduced cells serve as the source of regenerated cartilage or as a cytokine delivery system, chronic expression of their transgenes might be inappropriate. Continued stimulation of cartilage matrix formation could, for instance, lead to focal hyperplasia of the cartilage with loss of joint congruity and subsequent degeneration. There is also the additional concern that excessive production of chondrogenic factors promotes the formation of osteophytes. Conversely, too short a term of expression might lead to an inadequate response.

It is known that gene expression is largely, although not entirely, regulated by promoter regions of DNA adjacent to the genes they regulate. The present invention provides for use of viral promoters active in eukaryotic cells, as well as the mixing and matching of these promoter and additional enhancer sequences to suit the artisan's need. This invention also provides for promoters useful in plasmid constructions, including but not limited to a cytomegalovirus (CMV) promoter, a Rous Sarcoma virus (RSV) promoter, a Murine Leukemia Virus (MLV) promoter, a B-actin promoter, as well as any cell-specific eukaryotic promoter sequence that would be known to be active in the cell targeted for transduction. These are very strong promoters but in many types of eukaryotic cells, the genes they drive are expressed transiently. As an alternative, the present invention provides for use of alternative promoters, e.g., strong chondrocyte promoters such as the type II collagen gene promoter. Additionally, the present invention allows for use of inducible promoters, including but not limited to inducible promoters regulating expression of IL-1, IL-6 and IL-8. Any eukaryotic promoter and/or enhancer sequence available to the skilled artisan which is known to control expression of the nucleic acid of interest may be used in either a viral or plasmid vector construction. As mentioned above, other promoters and vector constructs may be utilized to either shorten or lengthen the duration of in vivo expression within the transplanted chondrocyte/scaffold (e.g., chondrocyte/collagen) matrix.

In another preferred embodiment of the present invention, the chondrocyte cells retrieved for in vitro culture prior to transfection and transplantation are autologous cells.

In a particular embodiment of the present invention, cultures of articular chondrocytes to be used for allotransplantation are either transduced with the recombinant viral or plasmid DNA vector and selected with G418. Confluent monolayers of chondrocytes are harvested washed, and counted. These chondrocytes are added to a collagen solution, which is allowed to gel prior to transplantation. The chondrocyte/collagen mixture is adhered to the damaged region of articular cartilage with fibrin glue, a mixture of fibrinogen and thrombin.

Any known technique for surgical manipulation of articular cartilage may be utilized to practice the claimed invention (e.g., see Brittberg et al., 1994, New England Journal of Medicine 331(14):879–895 and Grande et al., 1989, J. Orthopaedic Research Society 7: 208–219).

Any of the vector and/or genes disclosed throughout this specification possess the potential for therapeutic use. Additionally, any such vectors and/or gene disclosed within the specification may be used in a model animal system to monitor, for example, localized effects of continuous cytokine expression in cartilage formation and rehabilitation. Such preferred vectors include, but are not limited to, a retroviral vector, such as MFG or BAG, and any plasmid DNA construct as disclosed throughout this specification. Preferred genes of biologically active gene fragments include but are not limited to human transforming growth factor-β (TGF-1β), insulin-like growth factor-1 (IGF-1), bone morphogenetic proteins (BMPs), IRAP and the extracellular domain of the interleukin-1 receptor protein. Human transforming growth factor-B maintains the differentiation of articular chondrocytes, increasing cartilage matrix synthesis and inhibiting cartilage matrix degradation. As noted throughout the specification, the human interleukin-1 receptor antagonist protein (IRAP) and the extracellular domain of the interleukin-1 receptor protein suppress the biological actions of IL-1, which promotes cartilage matrix breakdown and inhibits cartilage matrix synthesis.

MFG-IRAP is disclosed in this specification as useful in direct in vivo as well as ex vivo delivery and expression of IRAP in synovial cells.

MFG-TGF-β may be constructed by known recombinant DNA methods as disclosed in this specification in regard to construction of MFG-IRAP.

Another preferred method of the present invention involves non-viral based delivery of the DNA sequence of interest to the in vitro cultured, preferably utilizing a plasmid DNA vector, as discussed within this specification. Therefore, the invention also provides for treatment of a mammalian cartilage defect which comprises generating a recombinant plasmid DNA vector which contains a DNA sequence encoding a protein or biologically active fragment thereof, infecting a population of in vitro cultured chondrocyte cells with the recombinant viral vector so as to generate a population of transfected chondrocyte cells. These transfected chondrocyte cells are then transplanted to the joint area containing the damaged articular cartilage where expression of the recombinant DNA sequence provides therapeutic relief.

To this end, as discussed throughout this specification, the present invention also provides for the use of non-viral mediated delivery systems to chondrocytes cultured in vitro, including, but not limited to (a) direct injection of naked DNA; (b) liposome mediated transduction; (c) calcium phosphate [$Ca_3(PO_4)_2$] mediated cell transfection, the genetically transformed cells then returned extraarticularly to the mammalian host; (d) mammalian host cell transfection by electroporation, the genetically transformed cells then returned extraarticularly to the mammalian host; (e) DEAE-dextran mediated cell transfection, the genetically transformed cells then returned extraarticularly to the mammalian host; (f) polybrene mediated delivery; (g) protoplast fusion; (h) microinjection; and (i) polylysine mediated transformation.

A preferred embodiment of a method of treating a cartilage defect utilizing plasmid vectors is the treatment of full-thickness articular cartilage defects involving knee joints, especially a human full-thickness articular cartilage defect. It is also preferred that such a method utilize human autologous chondrocyte cells as the source of in vitro culture material.

It is also a preferred embodiment of plasmid-based cell delivery for treating articular cartilage defects to utilize the surgical transplantation protocol described in Example XVI and as described above, namely where allotransplantation comprises adhering a chondrocyte/collagen gel containing chondrocytes cells transfected with a plasmid based vector into a full-thickness articular cartilage defect using a fixative, especially where the fixative is fibrin glue (i.e., fibrinogen and thrombin).

The present invention also relates to transfer of genetically modified chondrocytes to regions of articular cartilage defects to study the effects of expression of one or more proteins in vivo on the various joint pathologies, similar to the discussion within this specification in regard to using transfer of transfected synovial cells to the joint space for use as a model in animal based studies of joint pathologies.

The specification enables gene delivery and expression to both synovial cells and chondrocyte cells, each a respective connective tissue. The advantages of both direct in vivo and ex vivo methods of delivery have been described for both cell types. To this end, the present invention also teaches a combinatorial use of synovial and chondrocyte cell delivery methods which provide prophylactic or therapeutic relief from various joint pathologies enumerated throughout the specification.

One or more distinct DNA sequences can be delivered to the effected joint or joints by using a strategy whereby multiple DNA sequences, each housed within an appropriate recombinant vector, is transferred to chondrocyte cells and/or synovial cells by the methods disclosed throughout the specification. It is then possible to deliver gene or gene fragment combinations which will promote either a prophylactic or therapeutic response in vivo.

It is preferred that the ex vivo method described above for gene transfer to chondrocytes be utilized in conjunction with ex vivo method of gene transfer to synovial cells.

It is also preferred that the ex vivo method described above for gene transfer to chondrocytes be utilized in conjunction with direct ex vivo method of gene transfer to synovial cells.

Therefore, a method of treating a human full-thickness mammalian cartilage defect is disclosed which involves infecting a population of in vitro cultured autologous chondrocyte cells with at least a first recombinant viral vector containing a DNA sequence encoding a protein or biologically active fragment which results in a population of transfected chondrocyte cells, infecting a population of in vitro cultured autologous synovial cells with at least a second recombinant viral vector containing a DNA sequence encoding a protein or biologically active fragment which results in a population of transfected synovial cells, and transplanting the transfected chondrocyte cells and synovial cells to the appropriate joint space as described throughout this specification such that subsequent expression the recombinant proteins within the targeted joint space substantially alleviates the cartilage defect.

In a preferred embodiment of dual gene transfer delivery methods, the transfected synovial cells are introduced into the joint space by intra-articular injection.

In a preferred embodiment of dual gene transfer, one DNA sequence is subcloned into a recombinant vector and targeted to the joint space by synovial cell transfection and intra-articular injection, wherein a second DNA sequence is subcloned into a recombinant vector in a second procedure and targeted to the area of damaged articular cartilage.

It is another preferred embodiment that the recombinant vector be a recombinant viral vector, especially an MFG based vector.

It will be evident that any combination of gene or gene fragments disclosed for either synovial or cartilage based delivery will be useful in any dual gene transfer procedure. More specifically, it is preferred that the gene or gene fragment be selected from the group consisting of TGF-1β, IGF-1, bone morphogenetic proteins (BMPs), IRAP and the extracellular domain of the interleukin-1 receptor protein.

The following examples are offered by way of illustration of the present invention, and not by way of limitation.

EXAMPLE I
Packaging of AAV

The only cis-acting sequences required for replication and packaging of recombinant adeno-associated virus (AAV) vector are the AAV terminal repeats. Up to 4 kb of DNA can be inserted between the terminal repeats without effecting viral replication or packaging. The virus rep proteins and viral capsid proteins are required in trans for virus replication as is an adenovirus helper. To package a recombinant AAV vector, the plasmid containing the terminal repeats and the therapeutic gene is co-transfected into cells with a plasmid that expresses the rep and capsid proteins. The transfected cells are then infected with adeno-associated virus and virus isolated from the cells about 48–72 hours post-transfection. The supernatants are heated to about 56° Centigrade to inactivate the adenovirus, leaving a pure virus stock of recombinant AAV.

EXAMPLE II
Electroporation

The connective tissue cells to be electroporated are placed into HEPES buffered saline (HBS) at a concentration of about $10^7$ cells per ml. The DNA to be electroporated is added at a concentration of about 5–20 ug/ml of HBS. The mixture is placed into a cuvette and inserted into the cuvette holder that accompanies the Bio-RAD electroporation device (1414 Harbour Way South, Richmond, Calif. 94804). A range between about 250 and 300 volts at a capacitance of about 960 ufarads is required for introduction of DNA into most eukaryotic cell types. Once the DNA and the cells are inserted into the Bio-RAD holder, a button is pushed and the set voltage is delivered to the cell-DNA solution. The cells are removed from the cuvette and replated on plastic dishes.

EXAMPLE III

Figure 2:
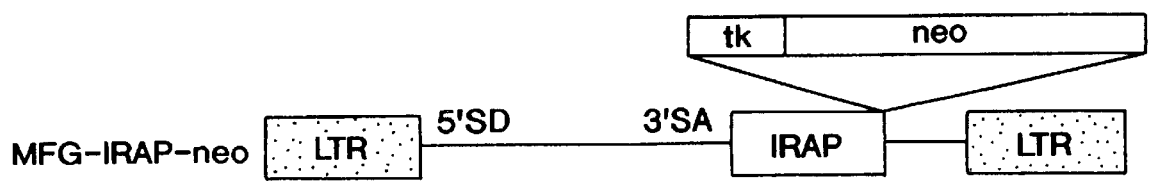
FIG. 2 shows the structure of the cDNA encoding the human interleukin-1 receptor antagonist protein (IRAP) gene with a selectable neo marker inserted into the retroviral vector MFG.
Figure 3:
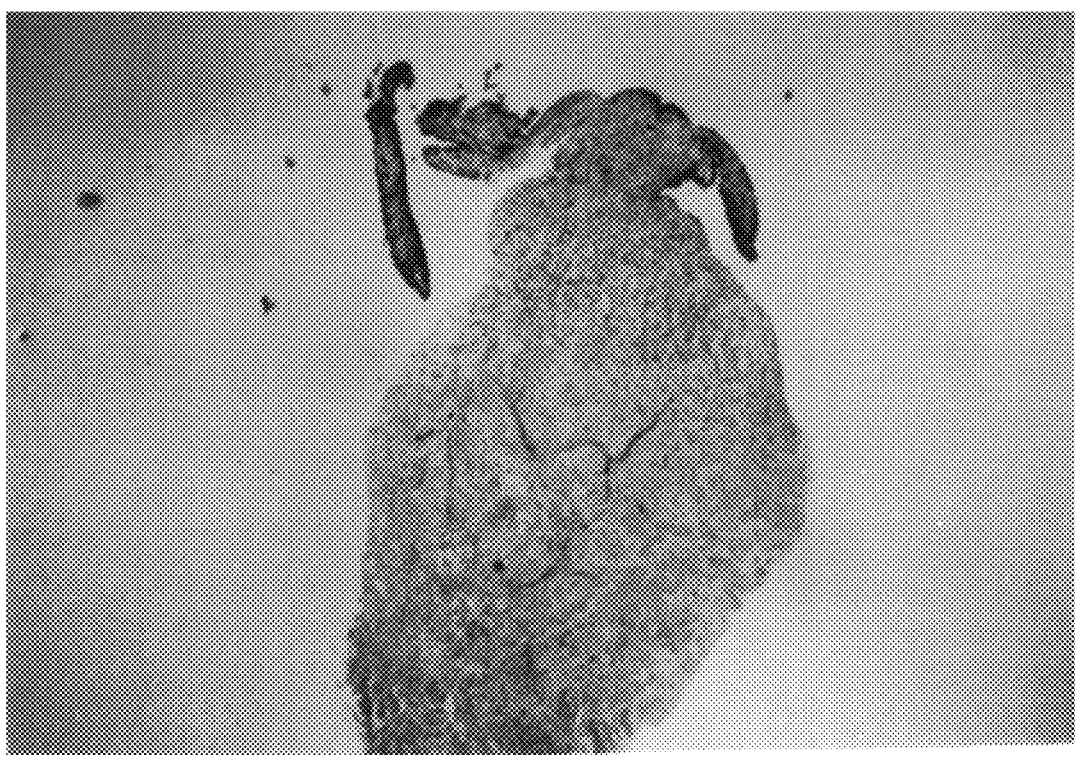
FIG. 3 shows a micrograph of synovium recovered from the knee of a rabbit approximately one month after intra-articular injection of Lac $Z^+$, neo synoviocytes employing the methods of this invention.

The cDNA encoding the human interleukin-1 receptor antagonist (IRAP) was inserted into the NcoI and BamHI cloning sites of the retroviral vector MFG as shown in FIG. 1. Specifically, a Pst1 to BamHI fragment from the IRAP cDNA was linked to a synthetic oligonucleotide adapter from the NcoI site (representing the start site of translation for IRAP) to the Pst1 site (approximately 12 base pairs downstream from the NcoI site) to the MFG backbone digested at NcoI and BamHI in a three part ligation reaction. This three part ligation involving a synthetic oligo and two DNA fragments is well known by those skilled in the art of cloning. LTR means long terminal repeats, 5'SD means 5' splice donor, 3'SA means 3' splice acceptor. The straight arrow and the crooked arrow in FIG. 1 represent unspliced and spliced messenger RNAs respectively. IRAP is encoded by the spliced message. FIG. 2 shows the cDNA encoding the human interleukin-1 receptor antagonist protein (IRAP) with a selectable neo gene marker. FIG. 3 shows a low power micrograph of synovium recovered from the knee of a rabbit one month after intra-articular injection of Lac $Z^+$, neo$^+$ synoviocytes. Tissue was stained histochemically for the presence of beta-galactosidase. This micrograph counterstained with eosin revealed an area of intensely stained, transplanted cells demonstrating that these cells have colonized the synovial lining of the recipient joint.

EXAMPLE IV
Animal Models

The methods of this invention of transferring genes to the synovia of mammalian joints permit the production and analysis of joint pathologies that were not previously possible. This is because the only other way of delivering potentially arthriotogenic compounds to the joint is by intra-articular injection. Not only are such compounds quickly cleared from joints, but the effects of bolus injections of these compounds do not accurately mimic physiological conditions where they are constantly produced over a long period of time. In contrast, the gene transfer technologies of this invention permit selected proteins of known or suspected involvement in the arthritic process to be expressed intra-articularly over an extended period of time, such as for example, at least a three month period. The animal models of this invention therefore permits the importance of each gene product to the arthritic process to be evaluated individually. Candidate genes include, but are not restricted to, those coding for cytokines such as interleukin-1 (IL-1) alpha, IL-1 beta, and TNF-alpha, and matrix metalloproteinases such as collagenases, gelatinases and stromelysins. Additionally, the gene transfer techniques of this invention are suitable for use in the screening of potentially therapeutic proteins. In this use, the animal models of the invention are initiated in joints whose synovia express gene coding for potential anti-arthritic proteins. Candidate proteins include, but are not restricted to, inhibitors of proteinases such as, for example, the tissue inhibitor of metalloproteinases, and cytokines such as, for example, transforming growth factor-beta.

Similar animal studies are also feasible for transfer of genetically modified chondrocytes to defective articular cartilage, as exemplified in Example XVI.

EXAMPLE V
Method for Using Synoviocytes as a Delivery System for Gene Therapy Rabbits are killed by intravenous injection of 4 ml nembutol, and their knees quickly shaved. Synovia are surgically removed from each knee under aseptic conditions, and the cells removed from their surrounding matrix by sequential digestion with trypsin and collagenase (0.2% w/v in Gey's Balanced Salt Solution) for about 30 minutes and about 2 hours, respectively. As noted in Example XIII, autologous synovial cells may be harvested as well. Rabbits are anesthesized by intravenous injection of 1 ml numbutal, and their knees quickly shaved. Synovia are surgically removed from each knee under aseptic conditions, and the knee surgically closed. The autologous synovial cells are again removed from their surrounding matrix by sequential digestion with trypsin and collagenase (0.2% w/v in Gey's Balanced Salt Solution) for about 30 minutes and about 2 hours. The cells recovered in this way are seeded into 25 cm$^2$ culture flasks with about 4 ml of Ham's $F_{12}$ nutrient medium supplemented with 10% fetal bovine serum, about 100 U/ml penicillin and about 100 μg/ml streptomycin, and incubated at about 37° in an atmosphere of 95% air, 5% $CO_2$. Following about 3–4 days incubation, the cells attain confluence. At this stage, the culture medium is removed and the cell sheet washed twice with approximately 5 mls of Gey's Balanced Salt Solution to remove non-adherent cells such as lymphocytes. The adherent cells are then treated with trypsin (0.25% w/v in balanced salt solution). This treatment detaches the fibroblastic, Type B synoviocytes, but leaves macrophages, polymorphonuclear leukocytes and the Type A synoviocytes attached to the culture vessel. The detached cells are recovered, re-seeded into 25 cm$^2$ culture vessels at a 1:2 split ratio, medium is added and the culture returned to the incubator. At confluence this procedure is repeated.

After the third such passage, the cells are uniformly fibroblastic and comprise a homogeneous population of Type B synoviocytes. At this stage, cells are infected with the retroviral vector.

Following infection, cells are transferred to fresh nutrient medium supplemented with about 1 mg/ml G418 (GIBCO/BRL, P.O. Box 68, Grand Island, N.Y. 14072–0068) and returned to the incubator. Medium is changed every three days as neo$^-$ cells die and the neo$^+$ cells proliferate and attain confluency. When confluent, the cells are trypsinized and subcultured as described above. One flask is set aside for staining with X-gal to confirm that the neo$^+$ cells are also Lac Z$^+$. When the subcultures are confluent, the medium is recovered and tested for the presence of IRAP, soluble IL-1R or other appropriate gene products as hereinbefore described. Producing synoviocyte cultures are then ready for transplantation.

The day before transplantation, the cells are recovered by trypsinizing, as hereinbefore described. These cells are then suspended in nutrient medium, and incubated overnight in an untreated plastic centrifuge tube. Under these conditions, the cells do not adhere, but they regenerate their cell surface proteins that were removed by trypsinizing.

The following morning, the cells are recovered by centrifuging, washed several times by resuspension in Gey's Balanced Salt Solution and finally resuspended at a concentration of about 10$^6$–10$^7$ cells/ml in Gey's solution. Approximately 1 ml of this suspension is then introduced into the knee joint of a recipient rabbit by intra-articular injection. For this purpose a 1 ml syringe with a 25-gauge hypodermic needle is used. Injection is carried out through the patellar tendon. Experiments in which radiopaque dye was injected have confirmed that this method successfully introduces material into all parts of the joint.

Variations on the disclosed harvesting, culture and transplantation conditions in regard to the numerous examples presented within this specification will be evident upon inspection of this specification. Several tangential points may be useful to one practicing the ex vivo based gene therapy portion of the disclosed invention:

(1) If the yield of synoviocytes from the harvested synovial tissue is poor, the surgical technique may be at fault. The synovium has a strong tendency to retract when cut. Therefore, the inner capsule is grasped firmly, and with it the synovium, while excising this tissue. A small (about 2 mm) transverse incision can be made inferiorly, followed by sliding one point of the forceps into the joint space so that the synovium and inner capsule are sandwiched between the points of the forceps. The tissue is then excised without releasing the tissue thus preventing retraction of the synovium.

(2) A two compartment digestion chamber may be used to initially separate the cells from extracellular debris. In lieu of this choice, synovial tissue may be digested in a single chamber vessel and filtered through a nylon monofilament mesh of 45 μm pore size.

(3) When resuspending cells, the smallest amount of medium possible can be used to prevent formation of clumps of cells, which are difficult to separate once formed.

(4) During trypsinization, synoviocytes can lose the fibroblastic morphology that they possess in adherence, and assume a rounded shape. The cells initially will detach in clumps of rounded cells; one may allow the majority of cells to separate from each other before stopping trypsinization.

(5) Synoviocytes may be transduced with multiple transgenes by use of retroviral vectors containing multiple transgenes or by sequential transduction by multiple retroviral vectors. In sequential transduction, the second transduction should be made following selection, when applicable, and passage after the first transduction.

(6) As the synovium is a well-innervated structure, intraarticular injection can be painful, especially if done rapidly. Intra-articular injection of a 1 ml volume should take 10 to 15 seconds.

(7) In the animal model, the depth of the needle stick should not exceed 1 cm during intraarticular injection, and depression of the syringe plunger should meet with little to no resistance. Resistance to advancement of the syringe plunger indicates that the tip of the needle is not in the joint space.

(8) In the animal model, to retrieve a useful volume of the injected Gey's solution during joint lavage, the needle should not be inserted too deeply, otherwise it may penetrate the posterior capsule and may lacerate the popliteal artery. Firm massage of the suprapatellar, infrapatellar, and lateral aspects of the knee during aspiration helps to increase the amount of fluid recovered; in general, it should be possible to recover $\geq$0.5 ml of fluid. When knees are badly inflamed, lavage is often difficult because of the presence of large numbers of leukocytes, fibrin, and other debris in the joint. Under such conditions the only recourse is to either anesthesize or sacrifice the animal and recover the Gey's solution surgically.

EXAMPLE VI

The method of Example V for producing generally uniformly fibroblastic cells of a homogeneous population of Type B synoviocytes was followed to effect growing cultures of lapine synovial fibroblasts. These growing cultures of lapine synovial fibroblasts were subsequently infected with an amphotropic retroviral vector carrying marker genes coding for beta-galactosidase (Lac Z) and resistance to the neomycin analogue G418 (neo$^+$). Following infection and growth in selective medium containing about 1 mg/ml G418, all cells stained positively in a histochemical stain for beta-galactosidase.

Neo selected cells carrying the Lac Z marker gene were transplanted back into the knees of recipient rabbits to examine the persistence and expression of these genes in vivo. Two weeks following transplantation, islands of Lac Z+ cells within the synovium of recipient knees were observed. This confirmed the ability of the method of this invention to introduce marker genes into rabbit synovia and to express them in situ.

EXAMPLE VII

Neo-selected, Lac Z+ synoviocytes were recovered from cell culture, suspended in Gey's Balanced Salt Solution and injected intra-articularly into the knee joints of recipient rabbits (about $10^5$–$10^7$ cells per knee). Contralateral control knees received only a carrier solution. At intervals up to 3 months following transplant, the rabbits were killed and their synovia and surrounding capsule recovered. Each sample may be analyzed in three ways. A third of the synovium was stained histochemically en masse for the presence of beta-galactosidase. A second portion may be used for immunocytochemistry using antibodies specific for bacterial beta-galactosidase. The final portion may be digested with trypsin and collagenase, and the cells thus recovered cultured in the presence of G418.

Staining of the bulk synovial tissue revealed extensive areas of Lac Z+ cells, visible to the naked eye. Control synovia remained colorless. Histochemical examination of synovia revealed the presence of islands of cells staining intensely positive for beta-galactosidase. These cells were present on the superficial layer of the synovial lining, and were absent from control synovia. From such tissue it was possible to grow Lac Z+, neo+ cells. Cells recovered from control tissue were Lac Z− and died when G418 was added to the culture. This indicates that the transplanted, transduced synovial fibroblasts have successfully recolonized the synovia of recipient joints, and continue to express the two marker genes, Lac Z and neo. Maintaining intra-articular Lac Z and neo expression in transplanted synoviocytes has been effected for 3 months using primary cells and one month using the HIG-82 cell line.

EXAMPLE VIII

Based upon the methods of the hereinbefore presented examples, and employing standard recombinant techniques well known by those skilled in the art, the human IRAP gene was incorporated into an MFG vector as shown in FIG. 1. Following the infection of synoviocyte cultures of rabbit origin with this viral vector, IRAP was secreted into the culture medium.

Figure 4:
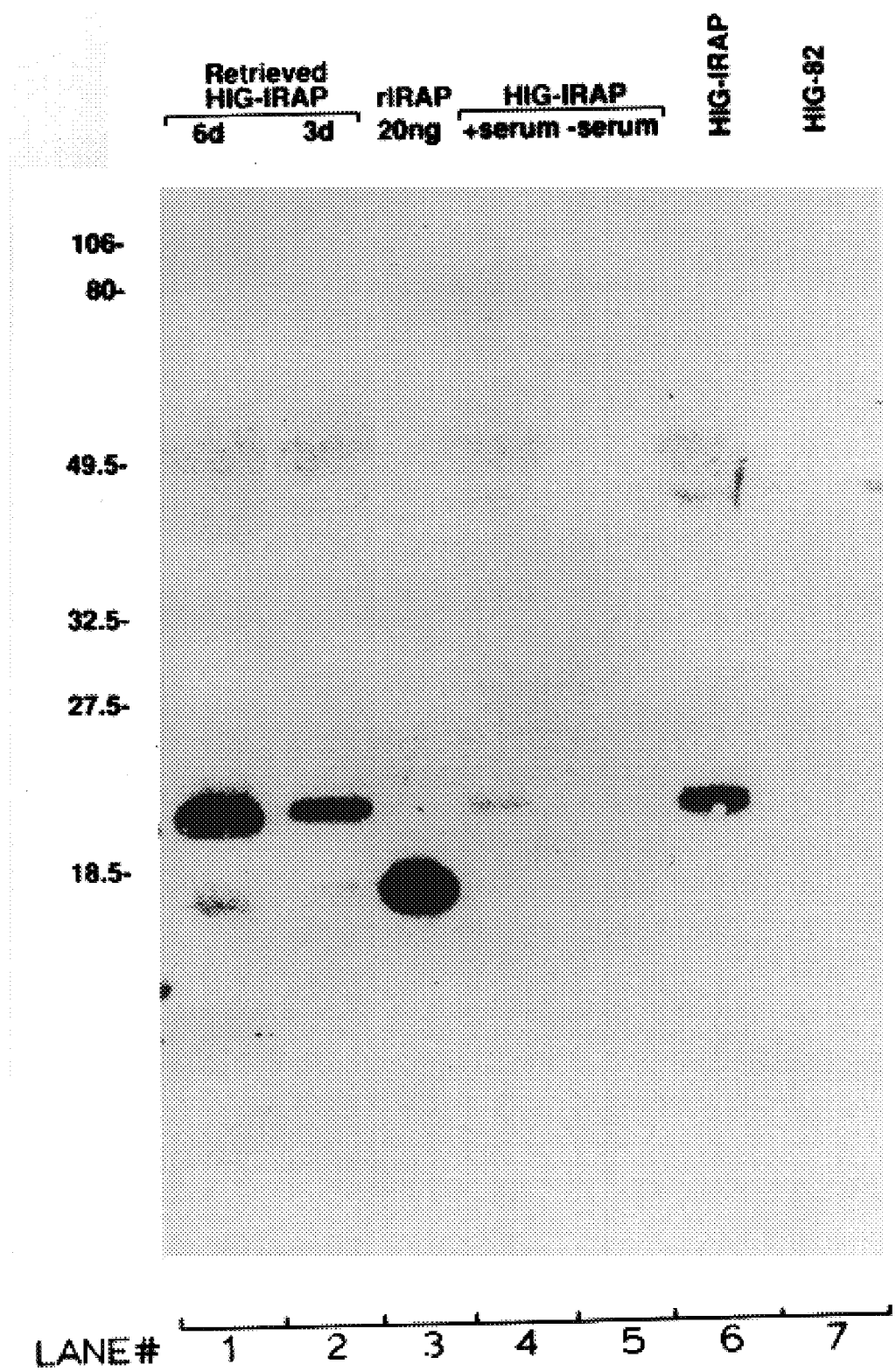
FIG. 4 shows a Western blot demonstrating the production of interleukin-1 receptor antagonist protein by four cultures of HIG-82 cells (Georgescu, et al., 1988, In Vitro 24: 1015–1022) infected using the method of this invention employing the MFG-IRAP viral vector.

Western blotting, well known by those skilled in the art, was carried out using an IRAP-specific rabbit polyclonal antibody that does not recognize human or rabbit IL-1 alpha or IL-1 beta, or rabbit IRAP. FIG. 4 shows a Western blot which sets forth the production of IRAP by four cultures of HIG-82 cells infected with MFG-IRAP. Three forms of the IRAP are present: a non-glycosylated form which runs with recombinant standards, and two larger glycosylated forms. The results of the Western blotting shown in FIG. 4 demonstrated that IRAP was produced by HIG-82 synoviocyte cell line (Georgescu, 1988, In Vitro 24: 1015–1022) following infection with the MFG-IRAP vector of this invention. The Western blotting of FIG. 4 shows the IRAP concentration of the conditioned medium is as high as 50 ng/ml. This is approximately equal to 500 ng IRAP/$10^6$ cells/day. Lane 1 and Lane 2 of FIG. 4 show that the recipient synovia tissue secrete substantial amounts of IRAP at 3 days (Lane 2) and 6 days (Lane 1). Lane 3 shows human recombinant IRAP. Lane 6 indicates that rabbit synovial cells produce a larger glycosylated version of this molecule after infection with MFG-IRAP. Lane 7 indicates that native rabbit synovial cells do not produce this glycosylated form.

Figure 5:
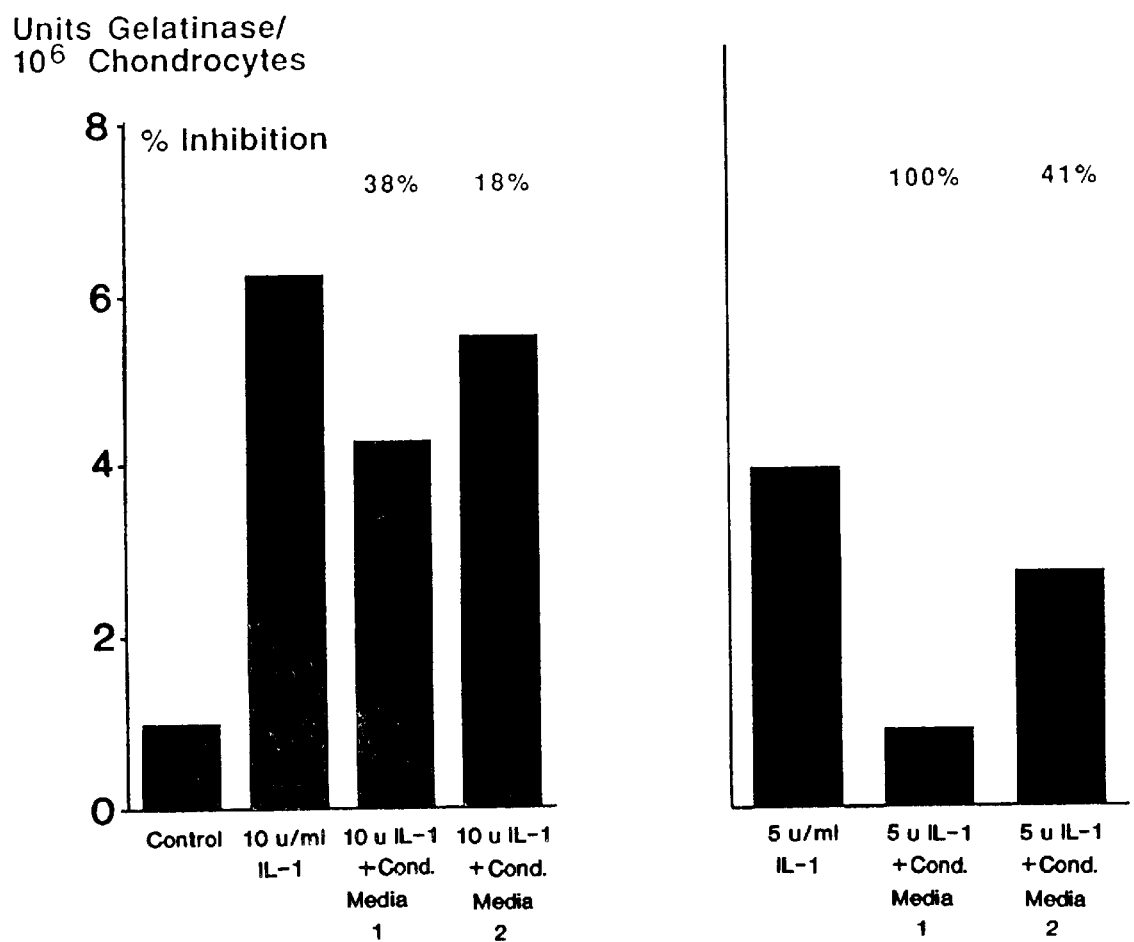
FIG. 5 shows data demonstrating that media conditioned by IRAP$^+$ synoviocytes block the induction of netral metalloproteinases in articular chondrocytes exposed to human rIL-$\beta$.

FIG. 5 shows that medium conditioned by IRAP+ synoviocytes blocks the induction of neutral metalloproteinases in articular chondrocytes exposed to recombinant human IL-1 beta. Chondrocytes normally secrete 1 U/$10^6$ cells, or less, gelatinase into their culture media. FIG. 5 shows that when to about 5 U/ml or 10 U/ml IL-1 are added, gelatinase production increases to over 4 U and 6U/$10^8$ cells, respectively. Addition of medium conditioned by MFG-IRAP-infected HIG-82 cells employed by the method of this invention suppressed gelatinase production by IL-1 treated chondrocytes. With 5 U/ml IL-1 (FIG. 5, right panel) inhibition was 100% for one culture and 41% for the other. With 10 U/ml IL-1, inhibition was reduced to 38% and 18% (FIG. 5, left panel) as is expected of a competitive inhibitor. These data demonstrate that the IRAP produced by HIG-82 cells infected with MFG-IRAP is biologically active.

EXAMPLE IX

This example demonstrates the uptake and expression of Lac Z gene by synoviocytes using infection by a liposome (lipofection). A six well plate containing synoviocyte cultures were transduced with the Lac Z gene by lipofection. The content of each well is as follows:

| Well 1 | Control cells, treated with liposomes alone |
| Well 2 | Control cells, treated with DNA alone |
| Well 3 | DNA + 150 nmole liposomes |
| Well 4 | DNA + 240 nmole liposomes |
| Well 5 | DNA + 300 nmole liposomes |
| Well 6 | DNA + 600 nmole liposomes |

Figure 6:
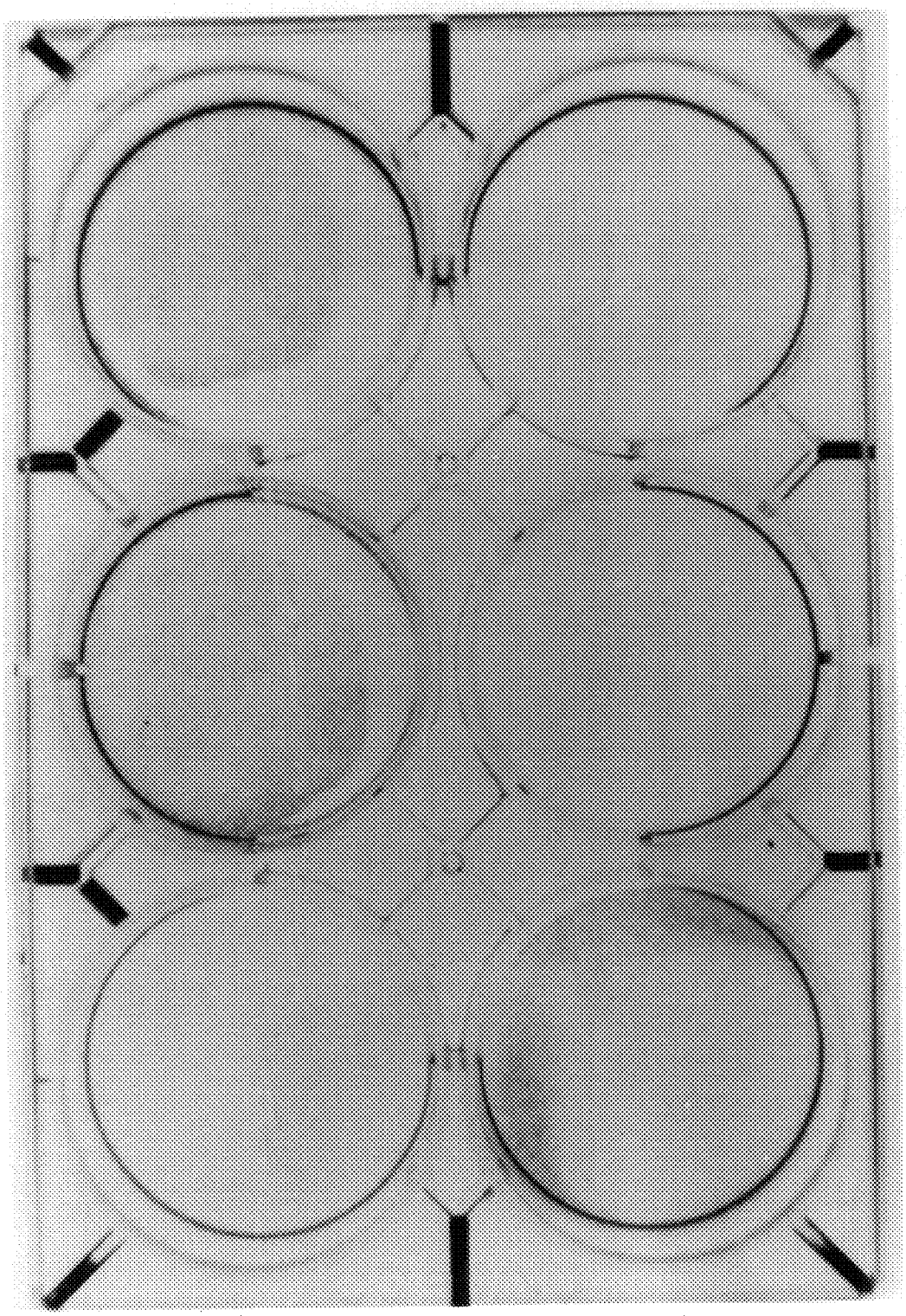
FIG. 6 shows the uptake and expression of the Lac Z gene by synoviocytes using lipofection. Well 1—Control cells, treated with liposomes alone; Well 2—Control cells, treated with DNA alone; Well 3—DNA+150 nmole liposomes; Well 4—DNA+240 nmole liposomes; Well 5—DNA+300 nmole liposomes; Well 6—DNA+600 nmole liposomes.

Wells 3–6 containing sub-confluent cultures of synovial fibroblasts were infected with 6 ug of DNA complexed with 150–600 nmoles/well of "DC-chol" liposome or in the alternative, with "SF-chol". Three days later, cells were stained histochemically for expression of beta-galactosidase (FIG. 6).

Table 1 shows the results of using the liposomes "DC-chol" and "SF-chol" in converting synoviocyte cultures to the Lac Z+ phenotype without selection. Table 1 sets forth that the "DC-chol" liposome in a concentration of about 300 nmole/well converted generally 30% of the synovial cells in synoviocyte cultures to the Lac Z+ phenotype without selection. Reduced expression was shown in Well 6 for "DC-chol" due to the toxic effect of the high liposome concentration.

TABLE 1

| | % Lac Z+ Cells | |
| --- | --- | --- |
| Liposome, nmole/well | DC-chol | SF-chol |
| 150 | 10 | 0.5 |
| 240 | 22 | 1.0 |
| 300 | 30 | 2.8 |
| 600 | NA | 3.5 |

In another embodiment of this invention, a gene and method of using this gene provides for the neutralization of interleukin-1. Interleukin-1 is a key mediator of cartilage destruction in arthritis. Interleukin-1 also causes inflammation and is a very powerful inducer of bone resorption. Many of these effects result from the ability of interleukin-1 to increase enormously the cellular synthesis of prostaglandin $E_2$, the neutral proteinases—collagenase, gelatinase, and stromelysin, and plasminogen activator. The catabolic effects of interleukin-1 upon cartilage are exacerbated by its ability to suppress the synthesis of the cartilaginous matrix by chondrocytes. Interleukin-1 is present at high concentrations in synovial fluids aspirated from arthritic joints and it has been demonstrated that intra-articular injection of recombinant interleukin-1 in animals causes cartilage breakdown and inflammation.

Figure 7:
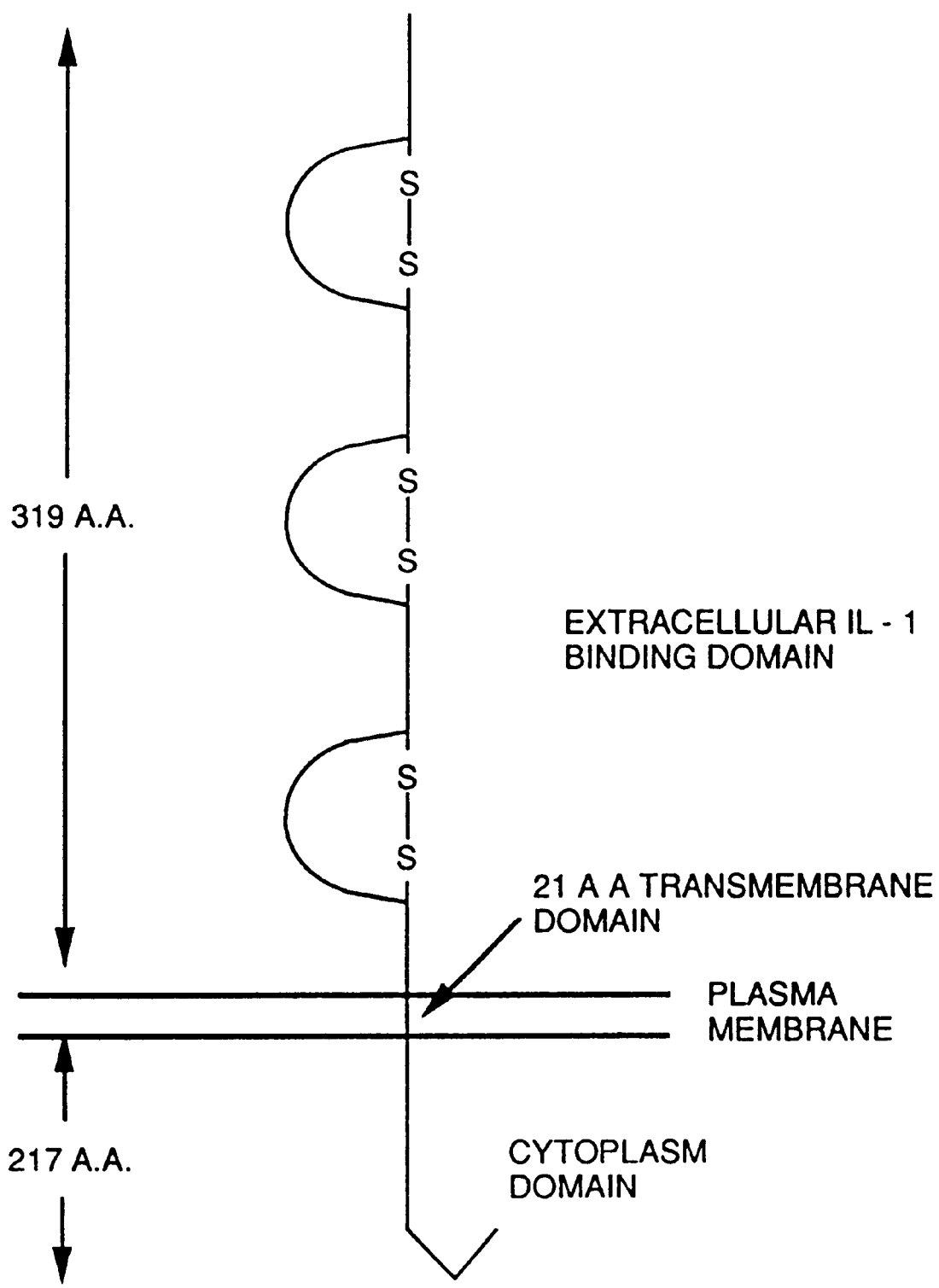
FIG. 7 shows the interleukin-1 binding domain amino acid arrangement.
Figure 8A:
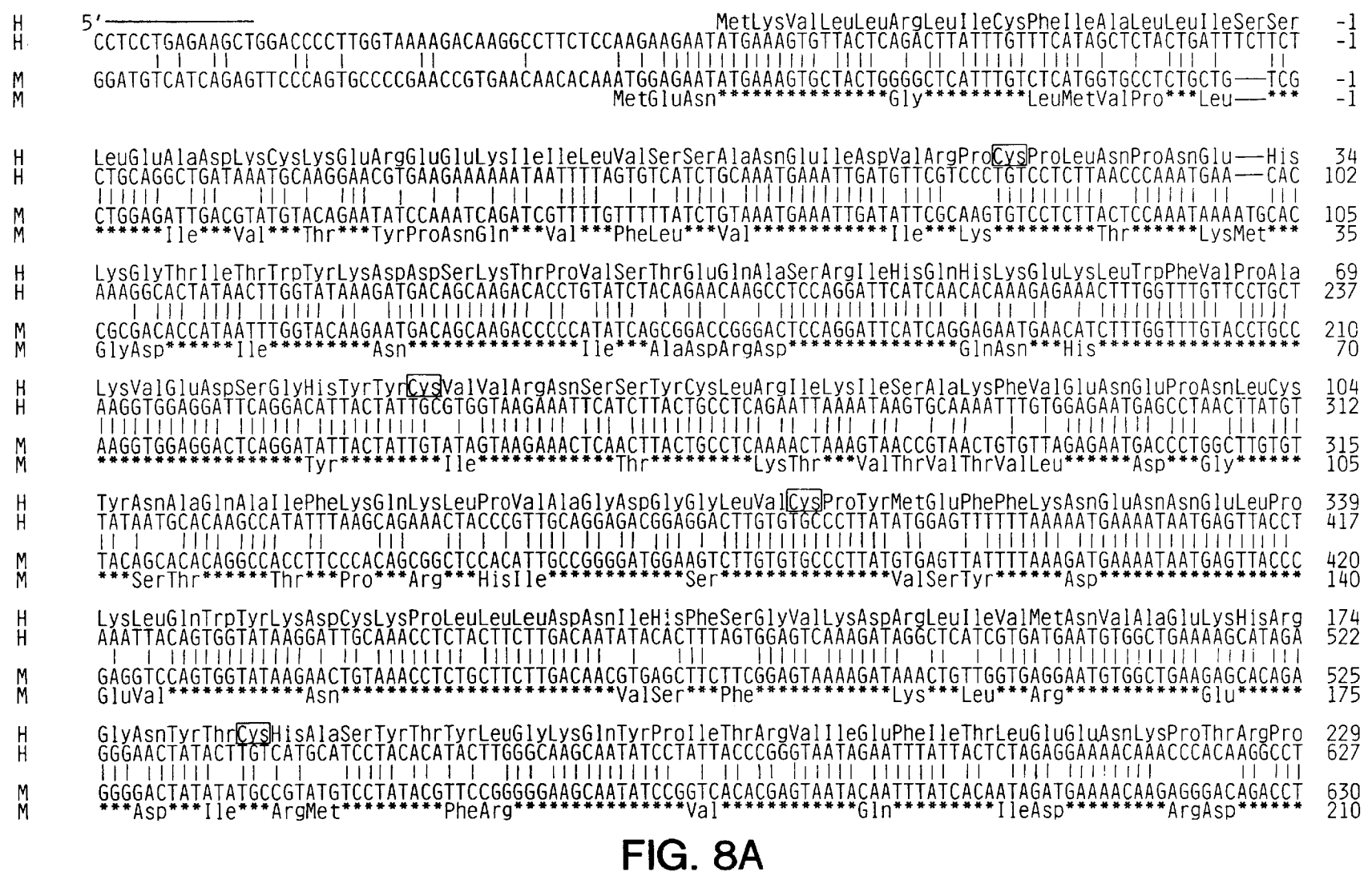
Figure 8B:
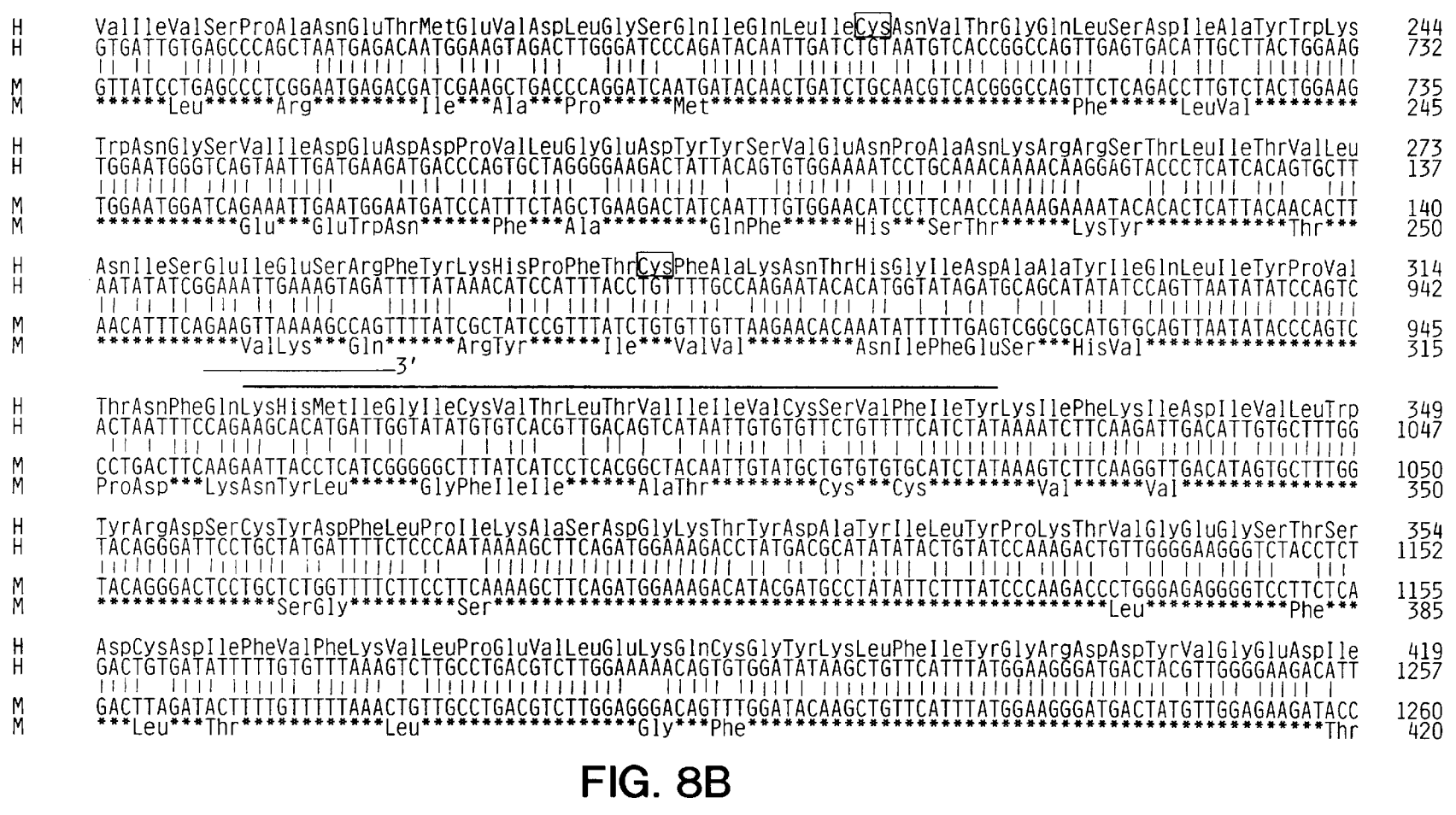
Figure 8C:
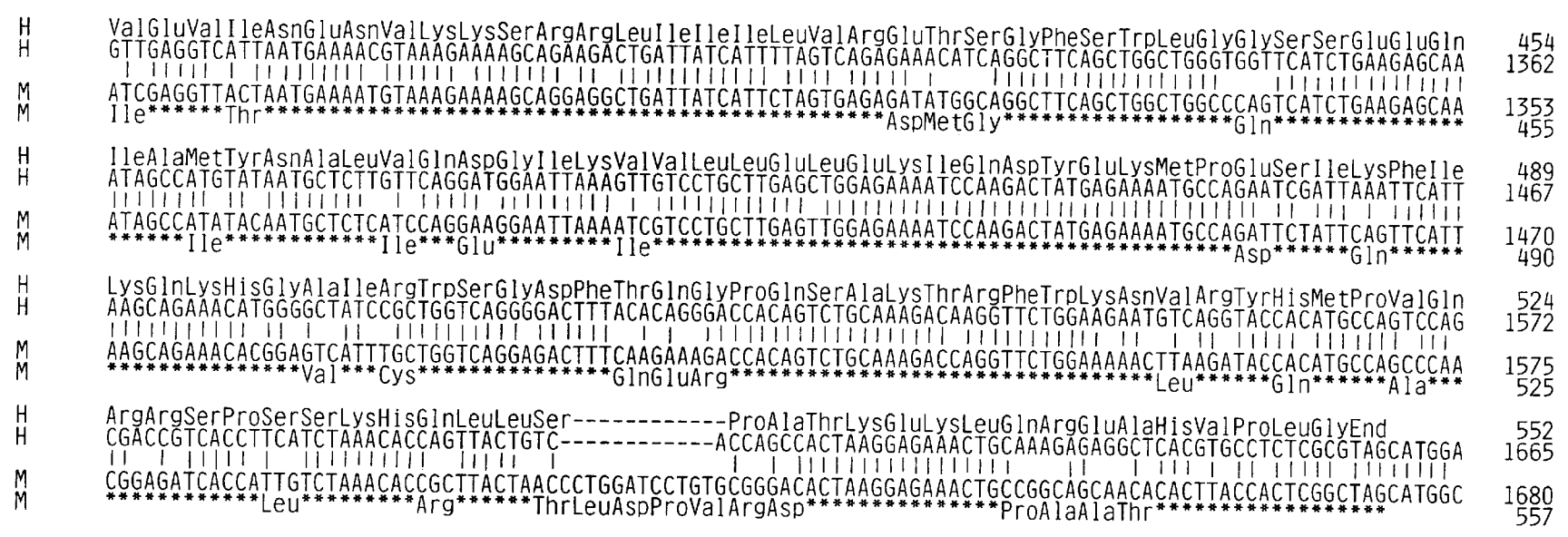
Figure 9:
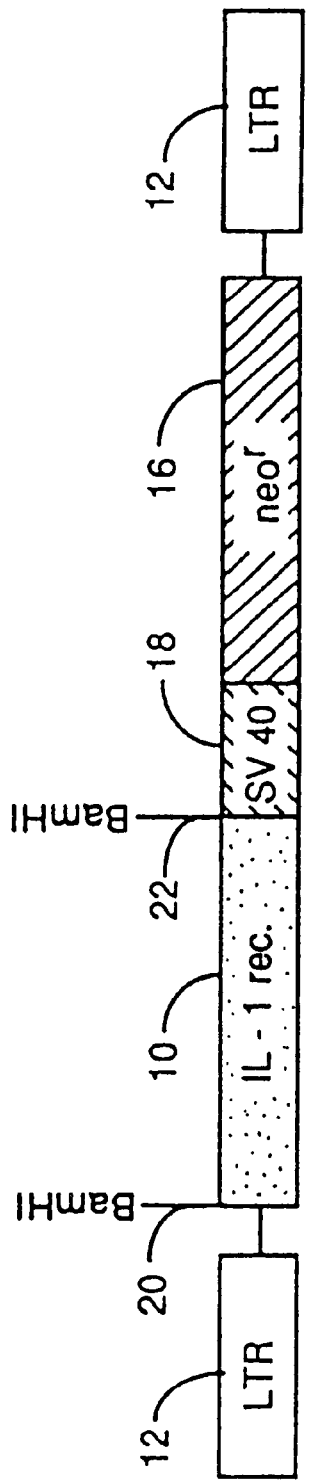
FIG. 9 shows gene encoding a truncated interleukin-1 receptor inserted into a retroviral vector.

Interleukin-1 exists as several species, such as unglycosylated polypeptide of 17,000 Daltons. Two species have previously been cloned, interleukin-1 alpha and interleukin-1 beta. The alpha form has a pI of approximately 5, and the beta form has a pI around 7. Despite the existence of these isoforms, interleukin-1 alpha and interleukin-1 beta have substantially identical biological properties and share common cell surface receptors. The type I interleukin-1 receptor is a 80 kDa (kilodalton) glycoprotein and contains an extracellular, interleukin-1 binding portion of 319 amino acids which are arranged in three immunoglobulin-like domains held together by disulfide bridges as shown in FIG. 7. A 21 amino acid trans-membrane domain joins the extracellular portion to the 217 amino acid cytoplasmic domain. FIGS. 8A–8C show the amino acid and nucleotide sequence of the human and mouse interleukin-1 receptors. In FIG. 8B, the 21 amino acid trans-membrane region of the interleukin-1 receptor is marked by the thicker solid line. In FIGS. 8A and 8B, the position of the 5' and 3' oligonucleotides for PCR are marked by thinner short lines, respectively. The lysine amino acid just 5' to the trans-membrane domain to be mutated to a stop codon is marked by a solid circle in FIG. 8B.

Synovium is by far the major, and perhaps the only, intra-articular source of interleukin-1 in the arthritic joint. Snyovia recovered from arthritic joints secrete high levels of interleukin-1. Both the resident synoviocytes and infiltrating blood mononuclear cells within the synovial lining produce interleukin-1.

The present invention provides a method of using in vivo a gene coding for a truncated form of the interleukin-1 receptor which retains its ability to bind interleukin-1 with high affinity but which is released extracellularly and therefore inactive in signal transduction. The binding of this truncated and modified receptor to interleukin-1 inhibits the intra-articular activity of interleukin-l. It is known that two forms of the interleukin-1 soluble receptor are available to practice the present invention, namely type I and type II. It will be understood to that both types are preferred.

This method of using a gene encoding the extracellular interleukin-1 binding domain of an interleukin-1 receptor that is capable of binding to and neutralizing interleukin-1 includes employing a retroviral vector carrying a truncated interleukin-1 receptor gene which encodes a truncated and soluble active form of the receptor. The expression of the novel interleukin-1 receptor gene is controlled by regulatory sequences contained within the vector that are active in eukaryotic cells. This recombinant viral vector is transfected into cell lines stably expressing the viral proteins in trans required for production of infectious virus particles carrying the recombinant vector. These viral particles are used to deliver the recombinant interleukin-1 receptor to the recipient synovial cells by direct virus infection in vivo.

The soluble human interleukin-1 receptor to be inserted into the retroviral vector may be generated by a polymerase chain reaction (PCR). An oligonucleotide complementary to the 5' leader sequence of the human interleukin-1 receptor (GCGGATCCCCTCCTGAGAAG; SEQ ID NO: 5) and an oligonucleotide complementary to a region just upstream from the transmembrane domain of the interleukin-1 receptor (GCGGATCCCATGTGCTACTGG; SEQ ID NO: 6) are used as primers for PCR. The primer for the region of the interleukin-1 receptor adjacent to the trans-membrane domain contains a single base change so that the lys codon at amino acid 336 (AAG) is changed to a stop codon (TAG). By inserting a translation stop codon just upstream from the transmembrane domain, a truncated form of interleukin-1 receptor that is secreted by the cell is generated. A BamHI recognition sequence (GGATCC) is added to the 5' end of the PCR primers, and following amplification, the resulting interleukin-1 receptor fragment is cloned into a BamHI site. A cDNA library from human T-cells is used as a source for the interleukin-1 receptor cDNA. To amplify the appropriate region of the interleukin-1 receptor from the cDNA library, the complementary primers are added to the DNA and 50 cycles of annealing, primer extension and denaturation are performed using a thermocycler and standard PCR reaction conditions well known by those persons skilled in the art. Following amplification of the interleukin-1 soluble receptor using the PCR process, the resulting fragment is digested with BamHI and inserted into the pLJ retroviral vector. The pLJ retroviral vector is available from A. J. Korman and R. C. Mulligan. See also *Proc. Natl. Acad. Sci.*, Vol. 84, pp. 2150–2154 (April 1987) co-authored by Alan J. Korman, J. Daniel Frantz, Jack L. Strominger and Richard C. Mulligan. Restriction analysis was performed to determine the correct orientation of the insert.

The retrovirus vector carrying the truncated interleukin-1 receptor is transferred into the CRIP (*Proc. Natl. Acad. Sci.*, Vol. 85, pp. 6460–6464 (1988), 0. Danos and R. C. Mulligan) packaging cell line using a standard $CaPO_4$ transfection procedure and cells wherein the viral vector is stably integrated and is selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into synovial cells thereby becoming an heritable trait of these cells. Virus stocks produced by this method are substantially free of contaminating helper-virus particles and are also non-pathogenic.

More specifically, the truncated interleukin-1 gene can be inserted into a retroviral vector under the regulation of a suitable eukaryotic promoter such as the retroviral promoter already contained within the gene transfer vector, such as for example, the pLJ vector shown in FIG. 9. FIG. 9 shows the structure of the pLJ interleukin receptor retroviral vector and partial restriction endonuclease map. Reference numeral 10 shows the interleukin-1 receptor inserted into a retroviral vector. Reference numeral 12 indicates long terminal repeats (LTR's) at each end of the structure of the pLJ interleukin receptor retroviral vector shown in FIG. 8. These LTR's regulate the viral transcription and expression of the interleukin-1 receptor. Bacterial gene encoding resistance to the antibiotic neomycin (neo-r) is shown at reference numeral 16. The Simian Virus 40 enhancer promoter (SV 40) is indicated at reference numeral 18, and regulates the expression of the neo-r gene. Reference numbers 20 and 22, respectively, show the sites wherein the resulting interleukin receptor fragment is cloned. It will be understood by those persons skilled in the art that other vectors containing different eukaryotic promoters may also be utilized to obtain a generally maximal level of interleukin-1 receptor expression. The vectors containing the truncated, and modified interleukin-1 receptor will be introduced into a retroviral packaging cell line (CRIP) by transfection and stable transformants isolated by selection for the expression of the neomycin resistance gene also carried by the pLJ vector. The CRIP cell line expresses all the proteins required for packaging of the exogenous retroviral RNA. Viral particles produced by the G418-selected CRIP cell lines will carry a recombinant retrovirus able to infect mammalian cells and stably express the interleukin-1 truncated receptor. The viral particles are used to infect synovial cells directly in vivo by injecting the virus into the joint space.

Another embodiment of this invention provides a method for using the hereinbefore described viral particles to infect in culture synovial cells obtained from the lining of the joint of a mammalian host. The advantage of the infection of synovial cells in culture is that infected cells harboring the interleukin-1 receptor retroviral construct can be selected using G418 for expression of the neomycin resistance gene. The infected synovial cells expressing the interleukin-1 receptor can then be transplanted back into the joint by intra-articular injection. The transplanted cells will express high levels of soluble interleukin-1 receptor in the joint space thereby binding to and neutralizing substantially all isoforms of interleukin-1, including interleukin-1 alpha and interleukin-1 beta.

The method used for transplantation of the synovial cells within the joint is a routine and relatively minor procedure used in the treatment of chronic inflammatory joint disease. Although synovium can be recovered from the joint during open surgery, it is now common to perform synovectomies, especially of the knee, through the arthroscope. The arthroscope is a small, hollow rod inserted into the knee via a small puncture wound. In addition to permitting the intra-articular insertion of a fibre-option system, the arthroscope allows access to surgical instruments, such that snyovial tissue can be removed arthroscopically. Such procedures can be carried out under "spinal" anesthetic and the patient allowed home the same day. In this manner sufficient synovium can be obtained from patients who will receive this gene therapy.

The synovial cells (synoviocytes) contained within the excised tissue may be aseptically recovered by enzymic digestion of the connective tissue matrix. Generally, the synovium is cut into pieces of approximately 1 millimeter diameter and digested sequentially with trypsin (0.2% w/v in Gey's Balanced Salt Solution) for 30 minutes at 37° Centigrade, and collagenase (0.2% w/v in Gey's Balanced Salt Solution) for 2 hours at 37° Centigrade. Cells recovered from this digestion are seeded into plastic culture dishes at a concentration of $10^4$–$10^5$ cells per square centimeter with Ham's $F_{12}$ medium supplemented with 10% fetal bovine serum and antibiotics. After 3–7 days, the culture medium is withdrawn. Non-adherent cells such as lymphocytes are removed by washing with Gey's Balanced Salt Solution and fresh medium added. The adherent cells can now be used as they are, allowed to grow to confluency or taken through one or more subcultures. Subcultivating expands the cell number and removes non-dividing cells such as macrophages.

Following genetic manipulation of the cells thus recovered, they can be removed from the culture dish by trypsinizing, scraping or other means, and made into a standard suspension. Gey's Balanced Salt Solution or other isotonic salt solutions of suitable composition, or saline solution are suitable carriers. A suspension of cells can then be injected into the recipient mammalian joint. Intra-articular injections of this type are routine and easily carried out in the doctor's office. No surgery is necessary. Very large numbers of cells can be introduced in this way and repeat injections carried out as needed.

Another embodiment of this invention is the gene produced by the hereinbefore described method of preparation. This gene carried by the retrovirus may be incorporated in a suitable pharmaceutical carrier, such as for example, buffered physiologic saline, for parenteral administration. This gene may be administered to a patient in a therapeutically effective dose. More specifically, this gene may be incorporated in a suitable pharmaceutical carrier at a therapeutically effective dose and administered by intra-articular injection. Therefore, the preferred mode regarding the ex vivo method of delivery is the removal of the patient's connective tissue (e.g., synovia), in vitro culture of this connective tissue, transduction of the DNA sequence of interest, followed by the above-mentioned manipulation prior to delivery to the afflicted joint of the patient.

In another embodiment of this invention, this gene may be administered to patients as a prophylactic measure to prevent the development of arthritis in those patients determined to be highly susceptible of developing this disease. More specifically, this gene carried by the retrovirus may be incorporated in a suitable pharmaceutical carrier at a prophylactically effective dose and administered by parenteral injection, including intra-articular injection.

EXAMPLE X

Fifty micrograms of a DNA plasmid vector molecule containing the interleukin-1 beta coding sequence ligated downstream of the CMV promoter was complexed with cationic liposomes, mixed with Geys biological buffer and injected intra-articularly into the knee joints of a rabbit. Forty eight hours subsequent to injection one nanogram of interleukin-1 beta was recovered from the knee joint area. Therefore, injection of the DNA containing liposome solution within the region of the synovial tissue prompted fusion of the liposomes to the synovial cells, transfer of the DNA plasmid vector into synovial cells and subsequent expression of the IL-1 beta gene. Additionally, it is possible to inject non-encapsulated (i.e., naked) DNA into the joint area and monitor transfection of the DNA vector into the synovial cells as determined by subsequent expression of the IL-1 beta gene in synovial cells. Therefore, either method may be utilized as a plausible alternative to the in vitro manipulation of synovia also exemplified in the present invention.

EXAMPLE XI

Figure 10:
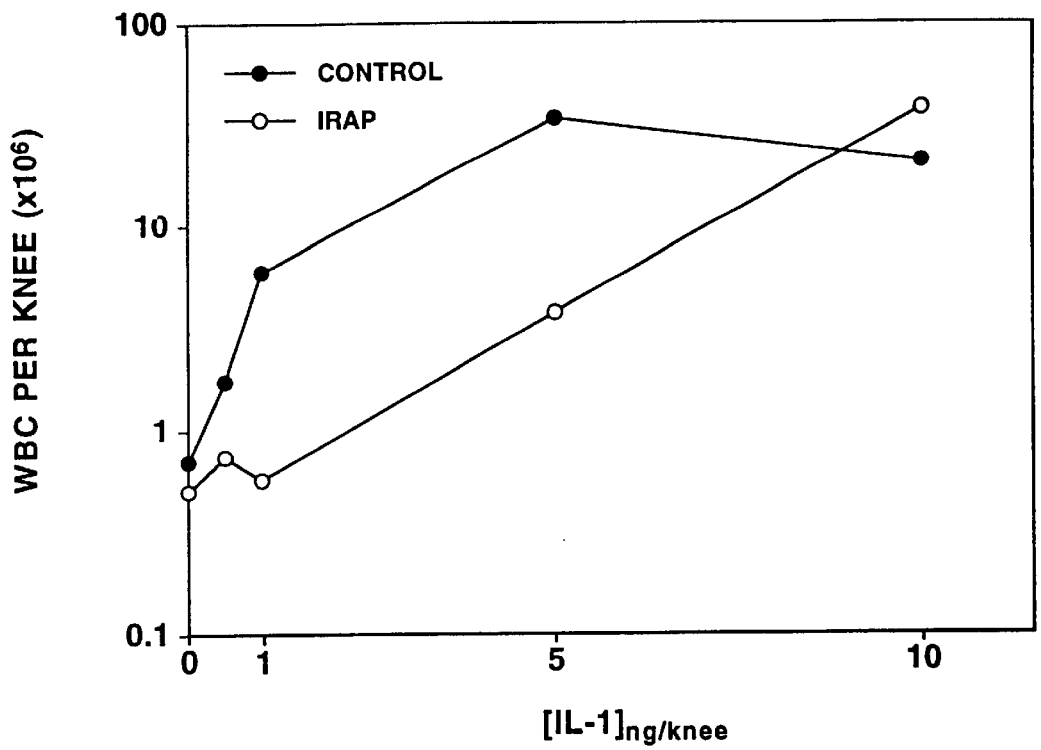
FIG. 10 shows antiinflammatory properties of the MFG-IRAP transgene. MFG-IRAP/HIG-82 cells ($10^7$) or untransduced HIG-82 cells ($10^7$) were transplanted to the knee joints of rabbits 3 days before intraarticular challenge with the indicated amounts of recombinant human interleukin-1 beta (rhIL-1$\beta$). Lavage of joints occurred 18 hours later, after which infiltrating leukocytes were counted.

The in vivo biological activity of the MFG-IRAP construct was tested as the ability to suppress the effects of IL-1β. Rabbit knees were injected with recombinant human IL-1β, known to cause an increased concentration of leukocytes within the afflicted joint space. Introduction of MFG-IRAP/HIG-82 cells into rabbit knees strongly suppresses IL-1β production of leukocytes to the afflicted joint space. In contrast, control HIG-82 cells do not suppress the leukocyte infiltration to the joint space challenged with IL-1β (see FIG. 10). Inhibition is greatest at the lowest doses of human recombinant IL-1β (hrIL-1β), as expected by the competitive mechanism through which IRAP antagonizes IL-1. Therefore, this rabbit model confirms that in vivo, intra-articular expression of IRAP is biologically active and can protect the joint from inflammation provoked by IL-1.

EXAMPLE XII

This example further evaluates ex vivo delivery into rabbit knee joints of the MFG-IRAP construct. As known, IRAP is an acidic glycoprotein of approximately 25 kDa that functions as a natural antagonist of the biological actions of interleukin-1 (IL-1) by binding to IL-1 receptors. Unlike IL-1, IRAP has no agonist activity, instead acting as a competitive inhibitor of the binding of IL-1.

This example shows that in vivo expression of IRAP by genetically modified synovial cells inhibits IL-1β-induced leukocyte infiltration into the joint space, synovial thickening and hypercellularity, and loss of proteoglycans from articular cartilage.

As mentioned within this specification, the preferred mode of treating a patient through the ex vivo route will be by transplanting genetically modified autologous synovial cells by intra-articular injection. However, HIG-82 cells, easily maintained in culture, were used for these experiments to show that intra-articularly expressed IRAP is effective in inhibiting the physiological sequelae of intra-articularly injected IL-1.

MFG-IRAP/HIG-82 cells or control (uninfected HIG-82) cells, were transplanted into rabbit knees by intra-articular injection by the methods disclosed within this specification. Briefly, cultures of these cells were infected with MFG-IRAP. Media conditioned for 3 days by infected MFG-IRAP/HIG 82 cells were assayed for human IRAP by ELISA assay using a commercial kit (R&D Systems, Minneapolis, Minn., USA) and found to contain approximately 500 ng IRAP/$10^6$ cells. Western blotting confirmed the presence of human IRAP of size 22–25 kDa. HIG-IRAP cells were trypsinized, suspended in Gey's balanced salt solution and 1 ml of suspension, containing $10^7$ cells, was injected intra-articularly into the left knee joints of New Zealand White rabbits (2.5 kg). The contralateral control knees received a similar injection of untransduced HIG-82 cells.

Three days following transplantation of the cells, knee joints were challenged by various doses of a single intra-articular injection of human recombinant IL-1β dissolved in 0.5 ml Gey's solution. Control knees were injected with 0.5 ml of Gey's solution.

Eighteen hours after injection of hrIL-1β, rabbits were killed and the knee joints evaluated histopathologically and for expression of IRAP. Each joint was first lavaged with 1 ml Gey's solution containing 10 mM EDTA. Cell counts in these washings were performed with a hemocytometer. An aliquot was removed for cytospinning and staining with 'DiffQuick' (Baxter Scientific Products) before examination under light microscopy. Washings were then centrifuged. Supernatants were removed for IRAP ELISA and for the determination of glycosaminoglycan (GAG) concentrations as an index of cartilage breakdown. GAG determinations were carried out with the dimethylmethylene blue assay (Farndale, et al., 1986, Biochim Biophys Acta 883: 173–177).

Synovia were dissected from the knee joints, fixed in 70% ethanol, dehydrated, embedded in paraffin, sectioned at 5 μm and stained with hematoxylin and eosin.

Figure 11:
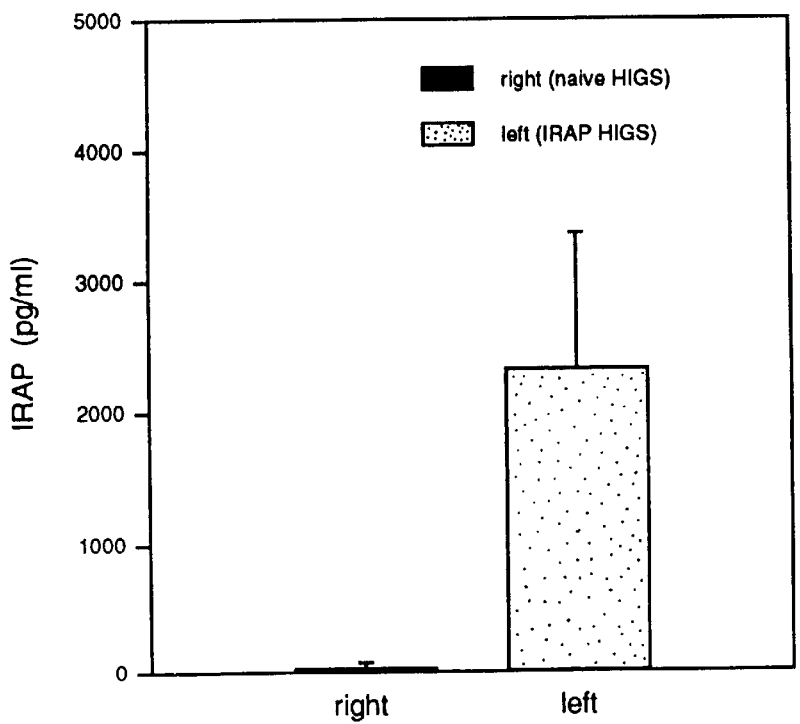
FIG. 11 shows levels or human IRAP in rabbit knees four days following transplant of synoviocytes. Either untransduced (naive) HIG-82 cells or cells carrying a human IRAP gene (MGF-IRAP/HIG-82) were injected intra-articularly in the knee joints or rabbits ($10^7$ cells/knee). Four days later, knees were lavaged and the concentration of human IRAP determined by ELISA. Values given are means+S.D. (n=15).
Figure 12A:
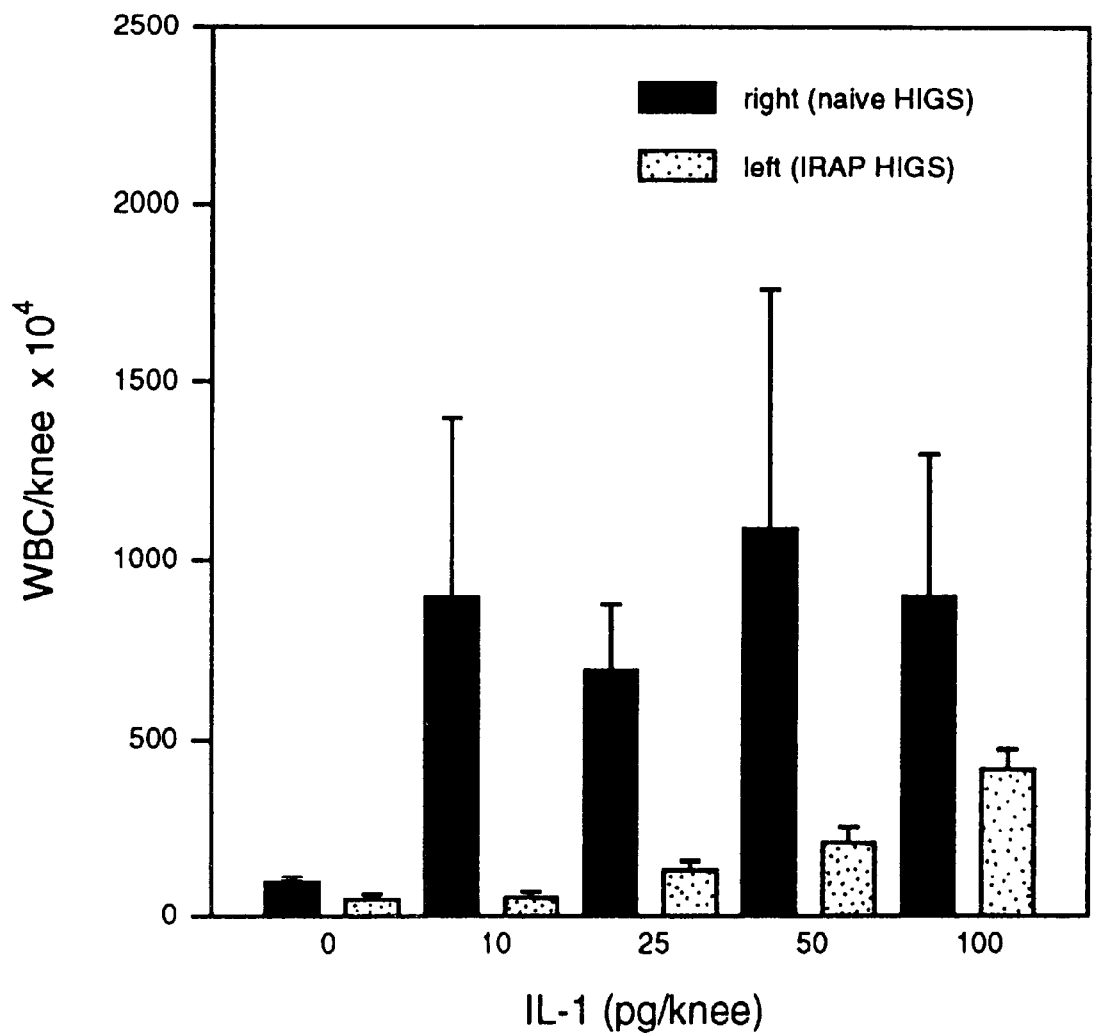
FIG. 12(A–C) shows inhibition of IL-1 induced leukocyte infiltration in knees expressing IRAP gene. Either naive or IRAP-transduced HIG-82 cells were transplanted into rabbit knee joints, as indicated Three days later 0–100 pg/knee hrIL-1B was intraarticularly injected at the indicated doses. The following day, knee joints were lavaged and the leukocytic infiltrate analyzed by counting with a hemocytometer and by cytospinning. Means+S.E. (n=3). (a) White blood cells (WBC) per knee. (b) Stained cytospin preparation of lavages from control knee injected with IL-1. Preparation was diluted 1:10 prior to cytospinning. (c) Stained cytospin preparation of lavages from IRAP-secreting knee injected with IL-1. The preparation was not diluted.

An average of 2.5ng human IRAP per knee was measured in joint lavages 4 days following transplant of MFG-IRAP/HIG 82 cells. Contralateral, control knees receiving naive HIG-82 cells had no detectable human IRAP (FIG. 11). To determine whether the observed level of IRAP expression was sufficient to inhibit the effects of IL-1 in vivo, increasing concentrations of IL-1β (0–100 pg) were injected into both the control and IRAP knees. As is shown in FIG. 12a, injection of hrIL-1β into control knees provoked a marked leukocytosis which was strongly suppressed in the genetically modified knees. There was also a statistically significant reduction in the white blood cell count in knees containing MFG-IRAP/HIG 82 cells which had not been injected with IL-1. This may reflect the influence of IRAP upon the slight inflammatory effect of injecting cells into joints. The degree of suppression by IRAP decreased as the amount of injected hrIL-1β increased, in keeping with the competitive mode of inhibition existing between IRAP and IL-1. No dose-response for hrIL-1β alone is evident in these particular experiments because this specific batch of IL-1 was especially effective in eliciting maximal response even at the lowest dose used.

Figure 12B:
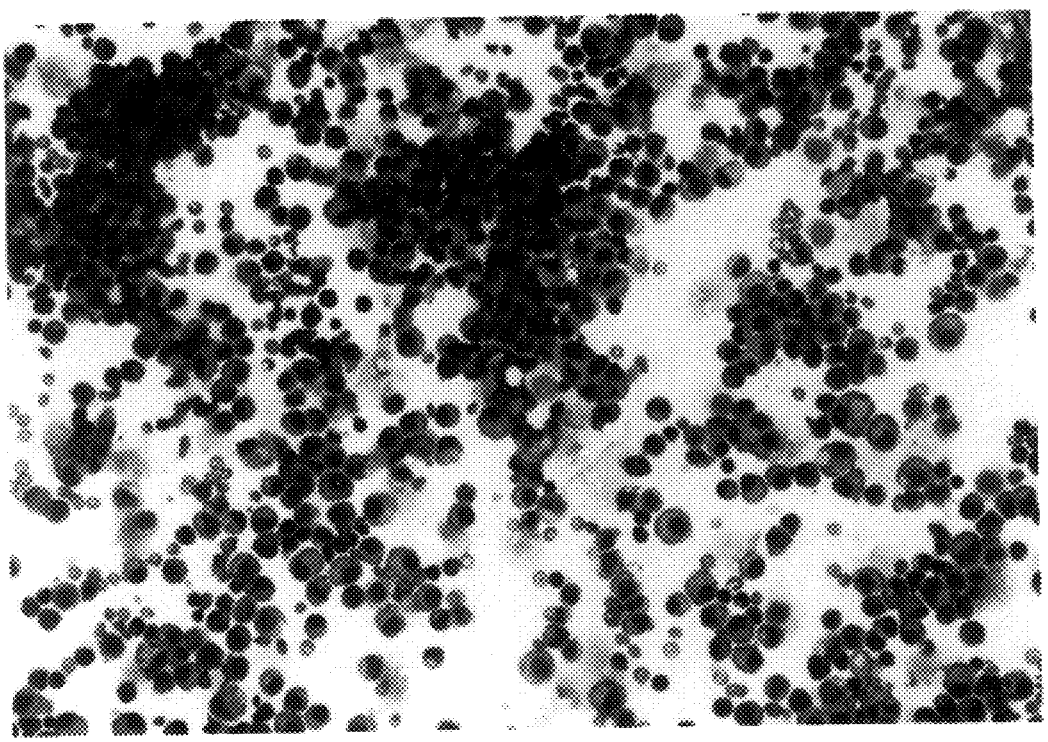
Figure 12C:
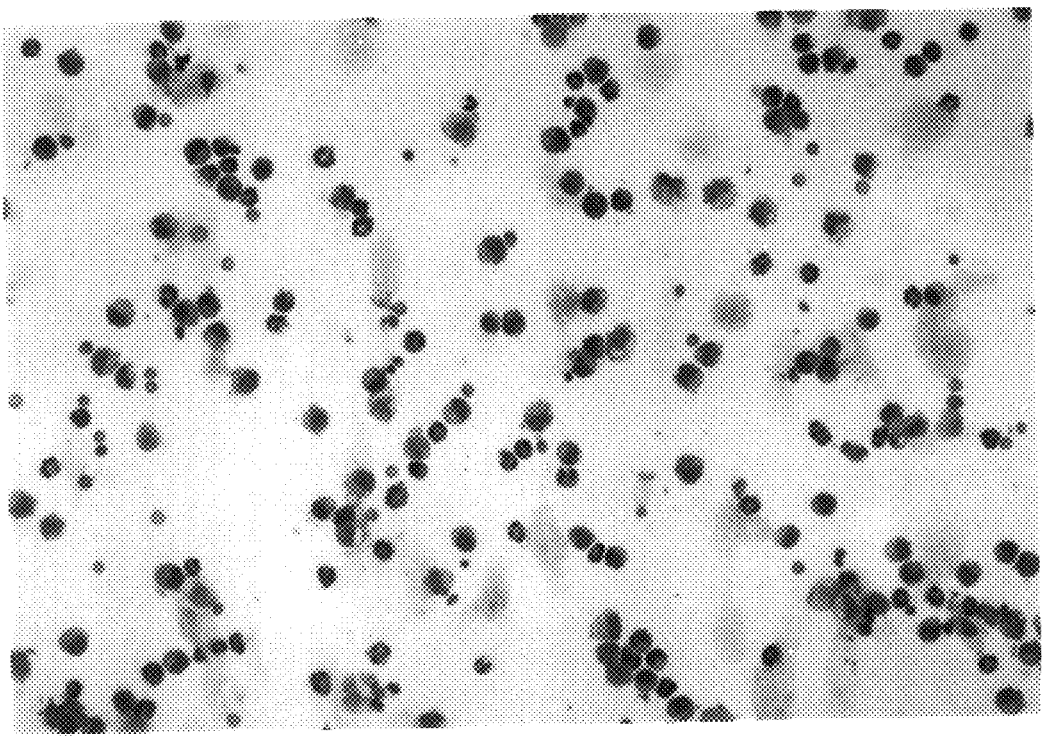

Examination of cytospins (FIG. 12b, 12c) revealed that most of the infiltrating leukocytes were neutrophils and monocytes. These preparations also serve to illustrate the efficiency with which leukocytosis was suppressed by the IRAP gene. Ten times the volume of lavage fluid is represented on the cytospin obtained from the IRAP-producing knees (FIG. 12c) compared to the non-IRAP knees (FIG. 12b).

Figure 13:
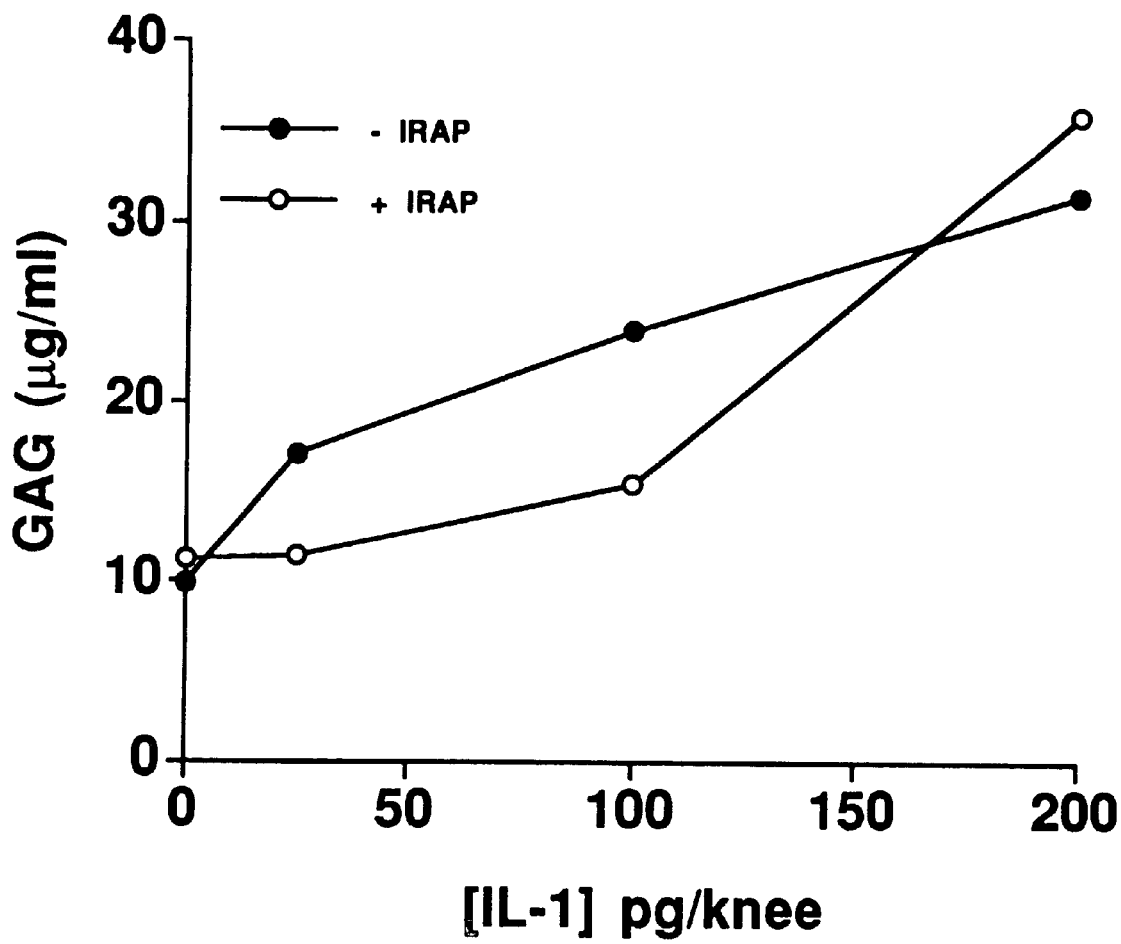
FIG. 13 shows suppression of IL-1 induced loss of proteoglycans from articular cartilage. Either naive or IRAP-transduced HIG-82 cells were transplanted into rabbits knee joints. Three days later, 0–200 pg/knee hrIL-1 was intra-articularly injected at the indicated doses. The following day, knee joints were lavaged and the level of glycosaminoglycans (GAG) as an index of cartilage breakdown was determined.

To determine if intra-articularly expressed IRAP was able to block cartilage breakdown, the concentration of glycosaminoglycans (GAG) in joint lavages was determined. GAG analyses of the washings from the control and IRAP expressing knees (FIG. 13) confirmed that transfer of the IRAP gene partially inhibited breakdown of the cartilaginous matrix in response to IL-1. Again, inhibition was strongest at the lowest concentrations of IL-1 and was abolished at the highest dose of IL-1 (FIG. 13).

Figure 14A:
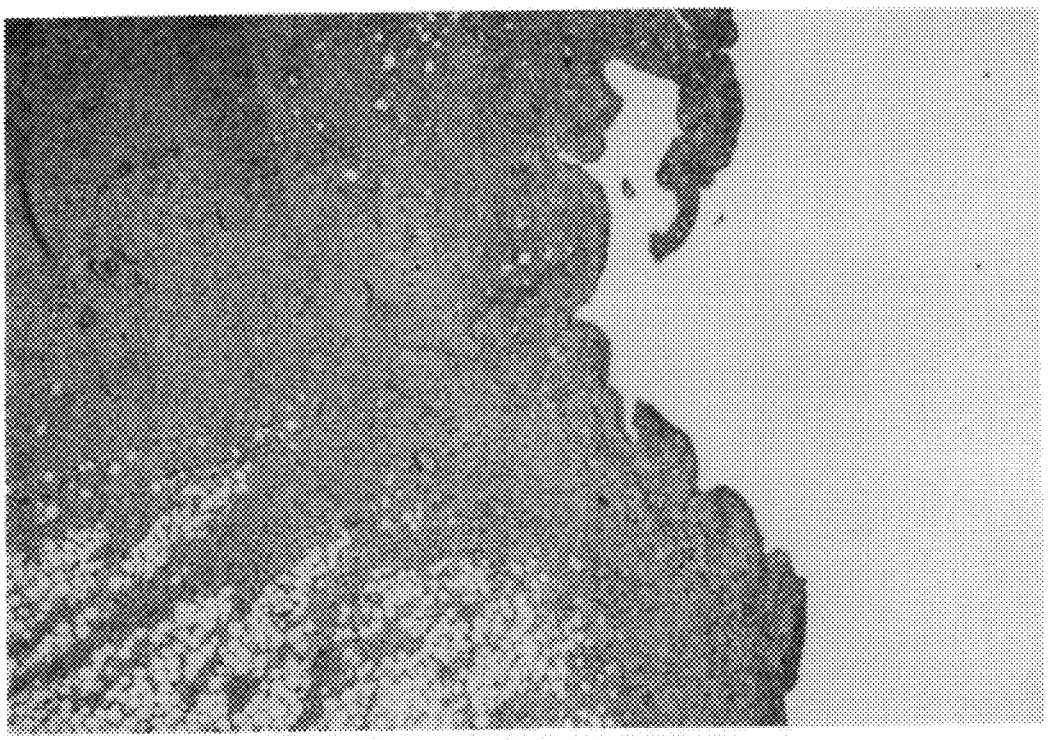
FIG. 14A–D shows suppression of IL-1 mediated synovial changes in knees expressing IRAP. Ten pg hrIL-1B was injected intra-articularly in each case. Synovia were harvested 18 hours after injection of IL-1β, i.e. 4 days after transplantation of naive or IRAP-secreting HIG-82 cells. (a) Control synovium following injection of IL-1, magnification×10. (b) IRAP-secreting synovium following injection of IL-1, magnification×10. (c) Control synovium following injection of IL-1, magnification×160. (d) IRAP-secreting synovium, magnification×160.
Figure 14B:
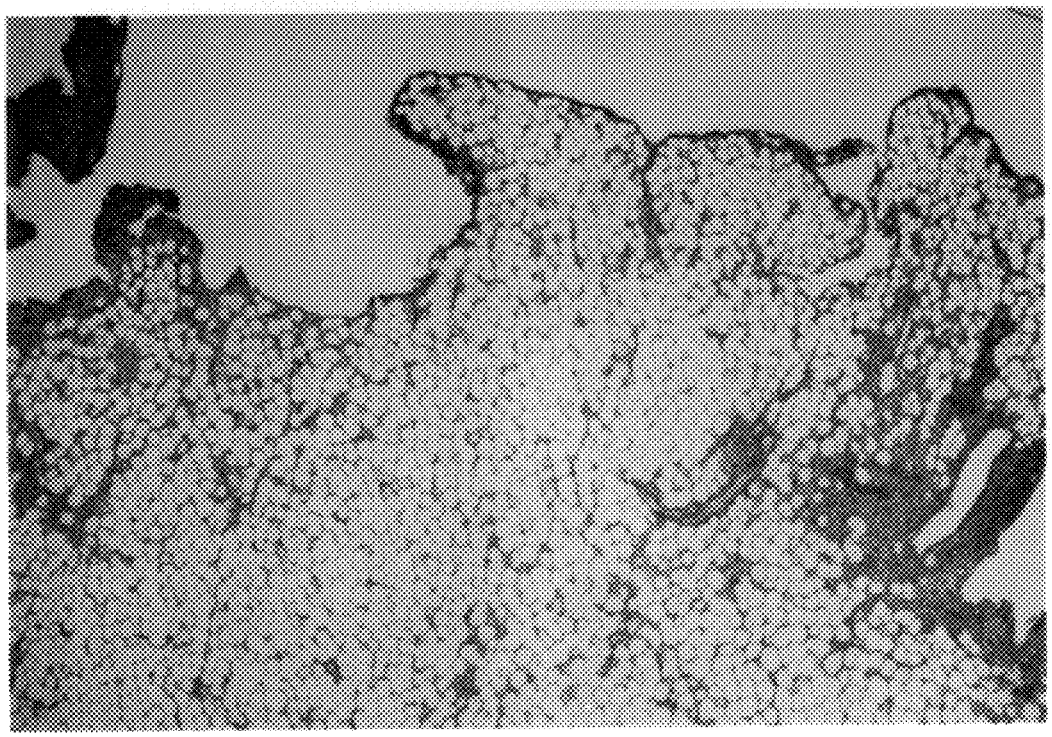
Figure 14C:
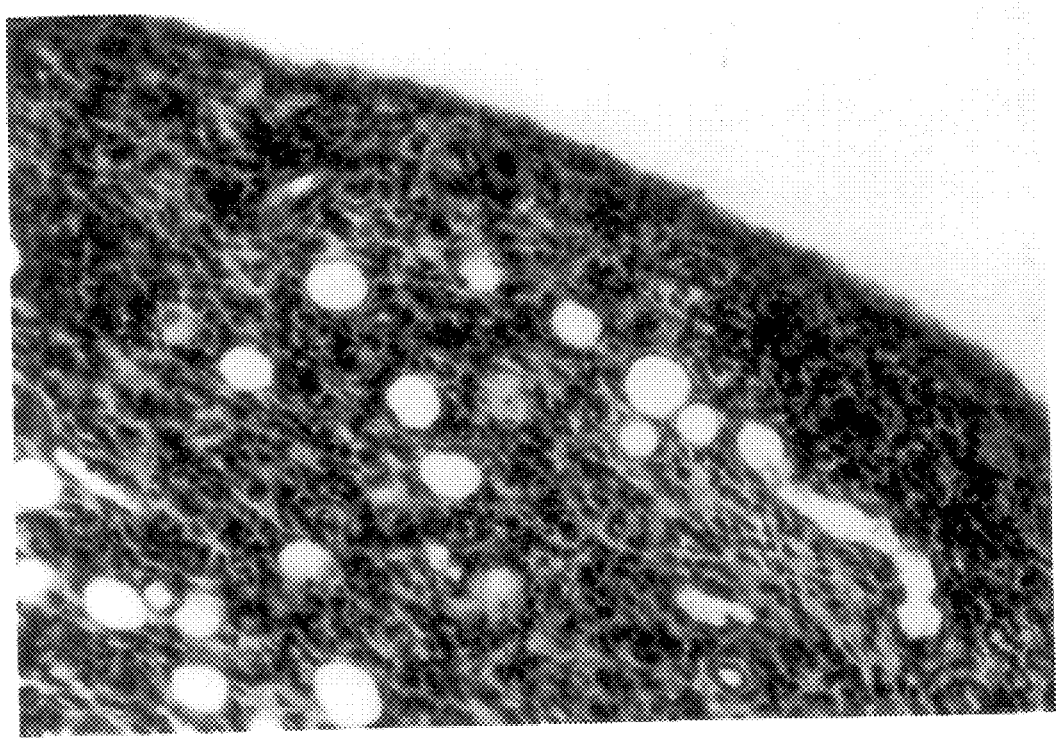
Figure 14D:
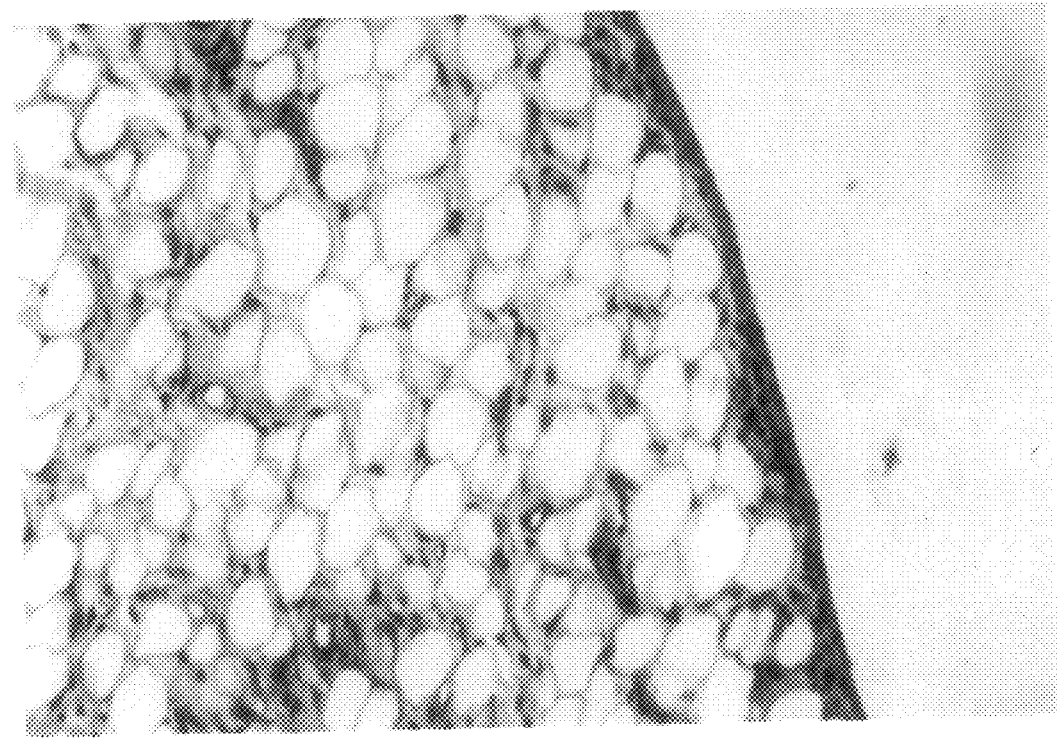

In response to 10 pg of injected hrIL-1β, control synovia became hypertrophic (FIG. 14a) and hypercellular (FIG. 14c). The increased cellularity of the synovia appeared to involve both increased numbers of synoviocytes and infiltration by leukocytes. In knees where MFG-IRAP/HIG 82 cells were present, these changes were completely suppressed and the synovia were nearly indistinguishable from control synovia (FIGS. 14b, 14d).

The ex vivo transfer of the human IRAP gene to the synovial lining of rabbit knees clearly protects these joints from the pathophysiological sequelae of subsequent intra-articular challenge by hrIL-1β.

Measurements of the amounts of IL-1 present in human, recombinant synovial fluids provide values in the range of 0–500 pg/ml (Westacott, et al., 1990, Ann Rheum Dis. 49: 676–681;Malvak, et al., 1993, Arthritis Rheum 36: 781–789). Thus the amounts of IRAP expressed intra-articularly during the present, short-term experiments should be sufficient to block the biological activities of IL-1 at the concentrations present in human arthritic joints.

EXAMPLE XIII

This example shows that the level of intraarticular IRAP expressed subsequent to ex vivo transplantation of synoviocytes transduced with MFG-IRAP is sufficient to inhibit several pathophysiological changes associated with antigen-induced arthritis of the rabbit knee. Intraarticularly expressed IRAP has both a chondroprotective and anti-inflammatory effect during the acute phase of this disease. Data disclosed in Example XII support the contention that the invention as disclosed and claimed is a marked improvement for treating connective tissue disorders such as arthritis in comparison to delivery of proteins to the afflicted joint. Example XII shows that ex vivo transfer of MFG-IRAP to the rabbit knee as disclosed throughout this specification results in the intraarticular accumulation of nanogram quantities of glycosylated, biologically active IRAP. This present example shows that this same gene therapy based product inhibits joint pathologies in a rabbit model of human rheumatoid arthritis.

Young adult rabbits were subjected to a surgical, partial synovectomy of the left knee joint to provide autologous cells. These autologous cells were used to produce cultures of rabbit synovial fibroblasts (type B synoviocytes) from these biopsies as described in Example V and Example IX. Subconfluent cultures were then transduced by infection with MFG-IRAP. Expression of the transgene was confirmed by measuring the concentrations of human IRAP in the conditioned media; values typically range from 100–500 ng IRAP/$10^6$cells/3 days. Sister cultures of synoviocytes from the same animal were infected with a BAG virus encoding the lac Z and $neo^r$ marker genes, and then selected for growth in the presence of G418 (1 mg/ml) to serve as controls. Untransduced synoviocytes were also used as additional controls.

During the period that the cells were being grown and transduced, the donor rabbits were sensitized to ovalbumin by a series of two intradermal injections of 5 mg ovalbumin emulsified in adjuvant, given two weeks apart. Two weeks after the second injection, an acute monarticular arthritis was initiated by the injection of 5 mg ovalbumin dissolved in 1 ml saline into the right knee joints. By this time the left, donor knees had regenerated their synovia, and were each injected with 1 ml saline as controls.

One day after the onset of arthritis, $10^7$ autologous cells, transduced with either the IRAP gene, or lac Z and neo genes, were injected into each arthritic knee, and each contralateral, non-arthritic knee. In other control experiments, knees were injected with untransduced, autologous cells. Groups of rabbits were killed 3 and 7 days later, corresponding to the middle and end of the acute phase of this arthropathy. Knees were lavaged with 1 ml of saline, prior to the removal of synovial tissue and articular cartilage for analysis.

Figure 15:
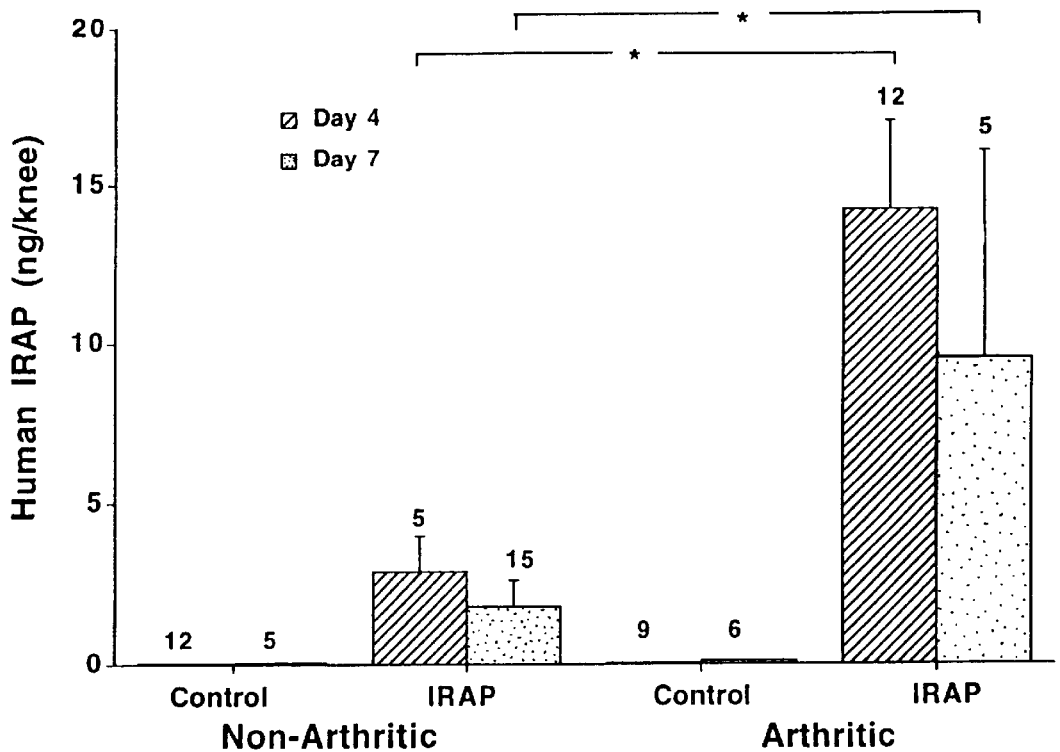
FIG. 15 shows expression of human IRAP in normal and arthritic knees of rabbits. Antigen-induced arthritis was initiated by injecting 5 mg ovalbumin into one knee joint (arthritic knee) of pre-sensitized rabbits on day 1. The contralateral knee (non-arthritic knee) received carrier solution only. On day 2, autologous synoviocytes ($10^7$/knee in 1 ml saline) were transferred to selected knee joints by intraarticular injection. Certain non-arthritic knees and arthritic knees received cells transduced with the human IRAP gene. Other non-arthritic and arthritic knees received untransduced cells or cells transduced with lac Z and $neo^r$ genes (controls). As the results obtained with these two types of control cells were indistinguishable, they have been pooled in the figures. Detailed methods for synoviocyte culture, transduction and intraarticular implantation are disclosed throughout this specification On day 4, knees were lavaged with 1 ml saline. On day 7, rabbits were killed and the knees again lavaged. The concentrations of human IRAP in the lavage fluids were determined by ELISA using a commercial kit (R&D Systems, Minneapolis, Minn.). Values given are means ±S.E. Numbers of knees are shown above each column. Asterisks denote values which differ at p<0.05 (t-test).

Intraarticular expression of the MFG-IRAP transgene was evaluated by ELISA measurements of human IRAP in the lavage fluids. IRAP concentrations in the control, non-arthritic knees is shown in FIG. 15. IRAP concentrations in the arthritic knees were always several-fold higher than in normal knees at both time points (FIG. 15). In both non-arthritic and arthritic knees transduced with MFG-IRAP, there was a slight decrease in IRAP expression with time. No human IRAP could be detected in sera obtained from normal or arthritic rabbits.

Figure 16:
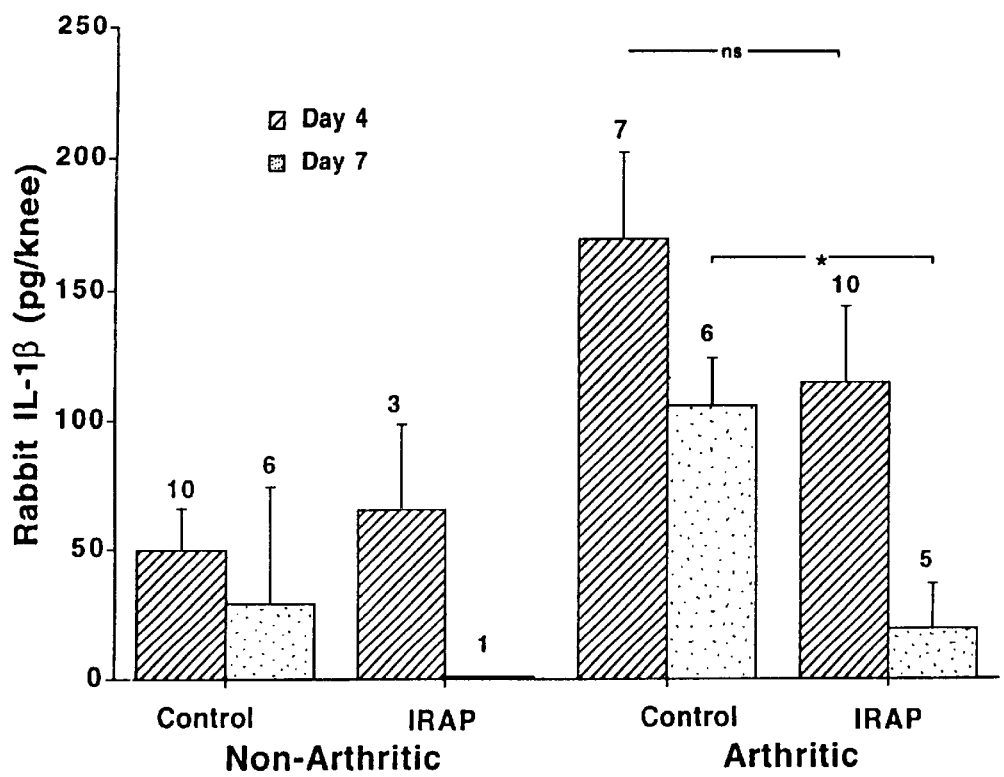
FIG. 16 shows concentrations of rabbit IL-1β in the normal and arthritic knee joints of rabbits. Experimental conditions were identical to those described in FIG. 15. However, lavage fluids were assayed for rabbit IL-1α and rabbit IL-1β by RIA using a commercial kit (Cytokine Sciences, Boston, Mass.). Low levels of IL-1β are present in non-arthritic knees as a reflection of the slight inflammatory effects provoked by intraarticular injection. No IL-1α was detectable in any of the samples. Values given are means ±S.E. Numbers of knees are shown above each column. Asterisks denote values which differ at p<0.05 (t-test).

During the course of these experiments, the intraarticular concentration of rabbit IL-1 in arthritic knees was in the range of 100–200 pg/knee (FIG. 16). No IL-1α could be detected by RIA of the lavage fluids. Thus the concentration of IRAP within these knees exceeded the concentration of IL-1 by factors of approximately 10–50. Concentrations of IL-1 were lower in day 7 arthritic knees receiving the IRAP gene (FIG. 16), suggesting that IRAP had inhibited an autocrine amplification loop.

Two major pathologies predominate in the rheumatoid joint: loss of articular cartilage and inflammation. The former occurs through a combination of reduced synthesis and enhanced degradation of the cartilaginous matrix, whereas inflammation is manifest as a synovitis accompanied by influx of leukocytes into the joint space.

Figure 17A:
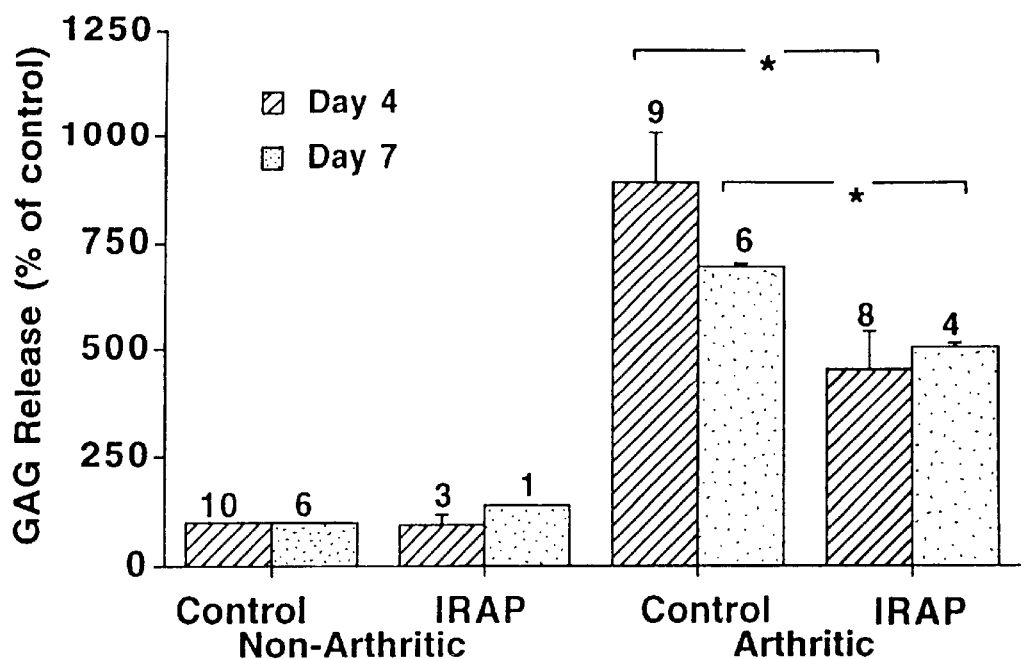
FIG. 17A–B shows the effect of IRAP gene transfer on cartilage matrix metabolism. Experimental conditions were as described for FIG. 15, except that rabbits were killed both at days 4 and 7. GAG concentrations in the lavage fluids (FIG. 17a) were measured spectrophotometrically by the dimethymethylene blue assay (Farndale, et al., 1986, Biochim. Biophy. Acta 883: 173–177). Fragments of articular cartilage were shaved from the femoral condyles of the knees and GAG synthesis (FIG. 17b) was measured as the uptake of $^{35}SO_4^{2-}$ into macromolecular material as described (Taskiran, et al., 1994, Biophys. Res. Commun. 200:142–148). Results are shown in each case as percent of control. Values given are means ±S.E. Numbers of knees are shown above each column.
Figure 17B:
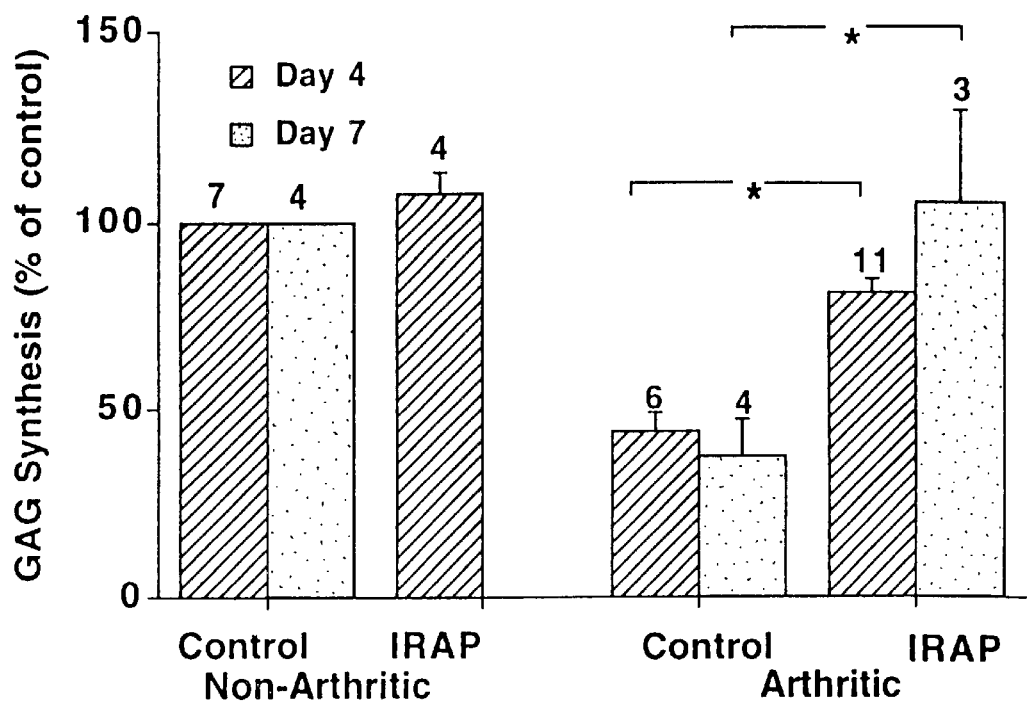
Figure 18:
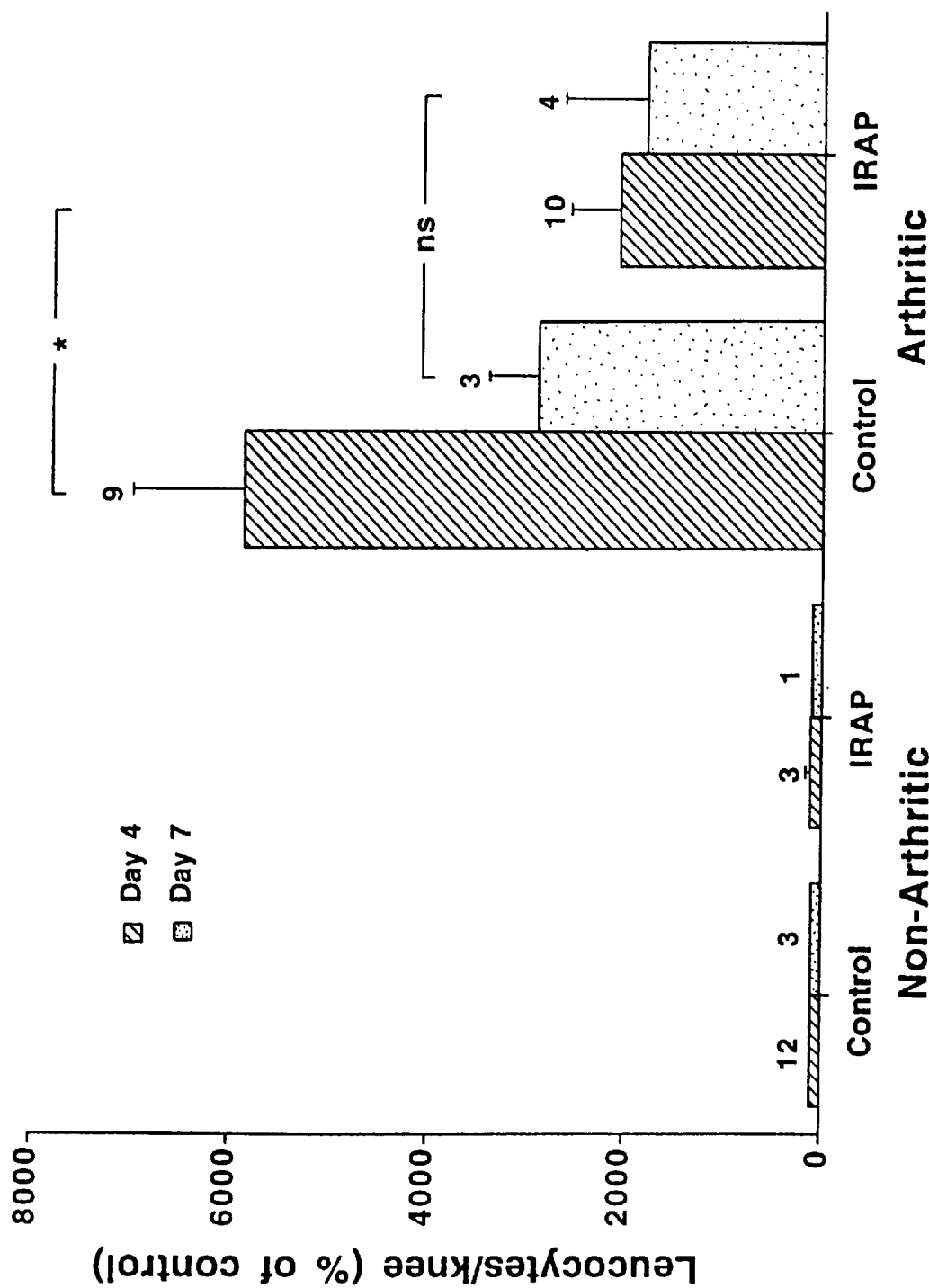
FIG. 18 shows effects of IRAP gene transfer on leucocytosis. Experiment conditions were identical to those described in FIG. 15. Numbers of leukocytes in the lavage fluids were determined with a hemocytometer. Values shown are means ±S.E. Numbers of knees are shown above each column. Asterisks denote values which differ at p<0.05 (t-test).

The onset of antigen-induced arthritis in this Example was accompanied by cartilage destruction, as reflected in the increased glycosaminoglycan (GAG) content of the lavage fluids (FIG. 17a), and reduced synthesis of cartilage proteoglycans, as reflected by lower uptake of $^{35}SO_4^{2-}$ (FIG. 17b). Knees expressing the MFG-IRAP transgene, but not control knees, were substantially protected from these changes. GAG release (FIG. 17a) was inhibited 55% on day 4 and 32% on day 7. Suppression of GAG synthesis (FIG. 17b) was inhibited by 68% on day 4 and 100% on day 7. The MFG-IRAP transgene also strongly reduced the influx of leukocytes into the joint space (FIG. 18), an effect that was stronger at day 4 (65% inhibition) than at day 7 (38% inhibition); indeed, the difference at day 7 failed to reach statistical significance.

The MFG-IRAP construct is utilized to exemplify the presently claimed invention. In addition to this construct, the ex vivo based teachings of this specification have been utilized to transfer to synovial cells and express in vivo DNA sequences encoding human IL-1α, human TNF-α soluble receptor, vIL-10, Lac Z and $neo^r$.

EXAMPLE XIV

The methods disclosed throughout this specification were utilized to express MFG-human IL-1 soluble receptor type I and type II constructs (with $neo^r$) within in vitro cultured synoviocytes. These transfected synoviocytes produce 1–2 ng/$10^6$ cells of IL-1 soluble receptor types I and II, following neo-selection. The additional methods disclosed throughout this specification may be utilized to procure in vivo expression data regarding these MFG-human IL-1 soluble receptor type I and type II constructs.

EXAMPLE XV

Rabbits were injected intraarticularly in one knee joint with a specific viral or non-viral vector disclosed in Table II. Contralateral knees were injected with a control, usually with the identical viral or non-viral vector with a different passenger gene. At intervals from 2 days to 2 weeks following intraarticular injection, rabbits were sacrificed and the knee joints harvested and stained with X-Gal to assay for LacZ expression. The results are depicted in Table II. The recombinant adenovirus vector comprising a CMV-LacZ fusion and the recombinant HSV vector comprising a CMV-LacZ fusion generated the highest expression level subsequent to intraarticular injection. The recombinant retroviral vector, MFG-LacZ, was not expressed in vivo, lending credence to the concept that retroviral vectors require actively dividing cells during the infection process and the concomitant low mitotic activity of synoviocytes in the joint lining.

However, an intra-articular injection of MFG-IRAP to synovial cells of an inflamed joint space supported retroviral transduction. Injection of MFG-IRAP into an inflamed rabbit knee lead to the intrarticular accumulation of 414.7 pg/knee at 24 hours post injection. The contralateral knee contained only 46.05 pg of human IRAP, close to background level.

TABLE II

| VECTOR DURATION | PROMOTER | In Vitro LAC Z cells (%) | In Vivo LEVEL | (Days) |
|---|---|---|---|---|
| | | EXPRESSION | | |
| Retrovirus (MFG) | LTR | 20–30 | 0 | 0 |
| HSV | CMV | 1 (toxic) | +++ | 5–7 |

TABLE II-continued

| VECTOR DURATION | PROMOTER | In Vitro LAC Z cells (%) | In Vivo LEVEL | EXPRESSION (Days) |
|---|---|---|---|---|
| Adenovirus | CMV | 100 | +++ | ≧14 |
| Liposome (DC-chol) | CMV | 20–30 | + | 1–2 |
| None (naked DNA) | CMV | 0 | ± | 1–2 |

Level of in vivo expression was evaluated subjectively on a scale of 0–+++, based upon the degree of staining with X-Gal.
LTR = viral long terminal repeat
CMV = cytomegalovirus

EXAMPLE XVI

Isolation and culture of articular chondrocytes

Three month old New Zealand white rabbits weighing approximately three kilograms were euthanized by IV injection of pentobarbital (100 mg/kg), and articular chondrocytes were isolated using the method of Green (1971, Clinical Orthopaedics and Related Research 75: 268). Briefly, cartilage shavings were minced and placed into the inner compartment of a two compartment digestion chamber containing 0.2% clostridial collagenase, grade CLS 1 and 0.2% trypsin, grade TRL. The minced cartilage was digested at 37° C. with gentle stirring for 2 hours. The chondrocyte suspension was collected from the outer compartment of the digestion chamber and centrifuged at 1500×g for 10 minutes. The cell pellet was resuspended in Ham's F-12 medium supplemented with 10% fetal bovine serum and 1% penicillin/1% streptomycin. This medium was changed every 5 days. Confluent cells were split 1 to 3 at passage 1.

Transduction of chondrocytes

Passage 1 chondrocytes were transduced when 75% confluent using the retroviral vector BAG-lacZ/neo$^r$, which carries both the lacZ and neo$^r$ genes (Price, et at, 1987, Proc. NaTe. Acad. Sci. 84:156–160), as exemplified throughout this specification. As discussed in previous examples, the lacZ gene encodes β-galactosidase which permits cells expressing this transgene to be stained blue by degrading the chromogenic substrate X-gal (5-bromo-4-chloro-3-indolyl-β-D-galactopyranoside). Additionally, the neo$^r$ gene encodes neomycin phosphotransferase which renders transduced cells resistant to the toxic effects of G418 (a synthetic neomycin analog) and can thus be used as a selectable marker. The transduction procedure was as follows. Media were decanted from T-25 culture flasks containing adherent chondrocytes at 75% confluence, after which $10^6$ retroviral vector particles and 8 µg polybrene suspended in 1 ml of medium were layered onto the cells. These cells were then incubated for 2 hours at 37dC in an atmosphere of 5% $CO_2$ and 95% air with gentle swirling of the suspension every 20 minutes. After this infection period, 3 mls of fresh medium was added to each flask, and the cultures were returned to the incubator. At confluence, the cells were subcultured at a 1 to 3 split ratio.

G418 selection and X-gal staining

To select for BAG-lacZ/neo$^r$ transduced chondrocytes which were expressing the neo$^r$ gene, freshly split cells were placed into medium containing 1 mg/ml G418;cells not expressing the transgene were thus eliminated. The G418 selected chondrocytes were allowed to grow to confluence. Some of these cultures were then stained with X-gal to check for the presence of β-galactosidase, the product of transgene lacZ expression. Duplicate flasks of confluent transduced cells were fixed in 0.5% glutaraldehyde for 30 minutes. Following fixation, the cells were washed twice in phosphate buffered saline containing 1 mM $MgCl_2$. X-gal staining was then performed using 0.1% X-gal solution at 37° C. overnight.

Preparation of collagen gels containing articular chondrocytes

Cultures of articular chondrocytes to be used for allotransplantation were either transduced with the retrovirus BAG-lacZ/neo$^r$ and selected with G418 as outlined above or left untreated for use as controls. Confluent monolayers of chondrocytes were harvested by exposure to 0.25% trypsin for 15 minutes. These cells were washed once in Gey's balanced salt solution and counted using a hemocytometer. Nine parts of cold (4° C.) acidic solution of type I bovine collagen (commercially available) was mixed with one part cold (4° C.) 10×phosphate buffered saline. The pH of the solution was titrated to 7.4 using 0.1N NaOH and 0.1N HCl. The chondrocytes were added to the collagen solution at a concentration of $2\times10^6$ cells/ml of solution. The cell suspension was aliquoted into sterile microfuge tubes (0.5 ml/tube) and incubated for 30 minutes at 37° C. to allow the collagen to gel.

Allograft of chondrocyte/collagen gels into full-thickness articular cartilage defects Three month old New Zealand white rabbits weighing approximately 3 kg were sedated using ketamine 25 mg/kg IM and acepromazine 1 mg/kg IM and then anesthetized using halothane at 1 L/min. Preoperative antibiotic prophylaxis with cephalothin 500 mg SQ was administered. Both knees were shaved, prepped with Betadine, and draped in sterile fashion. In our experiments, the right knees received the control gels (untransduced allogeneic articular chondrocytes) and the left knees received the test gels (BAG-lacZ/neo$^r$ transduced allogeneic articular chondrocytes). A medial parapatellar incision was used to access the joint space, and the medial femoral condyle was exposed after lateral dislocation of the patella. A nitrogen gas driven drill with a 1.5 mm burr was used to create a large 6 mm×3 mm×3 mm full-thickness medial femoral articular cartilage defect. The chondrocyte/collagen gel was evacuated from the microfuge tube into a sterile Petri dish and cut to an appropriate size with a scalpel. Fibrin glue was used to fix the chondrocyte/collagen gel into the full-thickness articular cartilage defect. Fibrin glue starts as two separate soluble components: fibrinogen and thrombin; when mixed, the thrombin cleaves fibrinogen resulting in a sticky fibrin clot. A drop of fibrinogen solution was placed into the cartilage defect thus coating the cut surfaces of the cartilage and subchondral bone; excess solution was blotted with sterile filter paper. The chondrocyte/collagen gel was coated with thrombin solution in a similar fashion. Treated in this manner, the gel, when placed into the defect, was immediately adherent. Direct irrigation of the gel in situ, as well as flexion and extension of the knee after relocation of the patella, did not dislodge the gel from the defect. The incision was then closed in two layers (synovium/joint capsule and skin) with 4.0 polyglycolic acid suture. Postoperatively, rabbits were given butorphenol 0.25 mg IM bid x 3 days and then bid prn for analgesia.

Harvest of the chondrocyte/collagen gels

Rabbits were sacrificed with a lethal dose of pentobarbital (100 mg/kg IV) at either 1, 2, or 4 weeks post-transplantation. The surgical site was exposed using the same approach as in the original surgery. In all of the rabbits tested, the collagen gels were found intact and firmly fixed within the cartilage defect. The collagen gel was sharply excised from the large full-thickness articular cartilage defect and placed into sterile Gey's balanced salt solution. The chondrocyte/collagen gels were subsequently analyzed by X-gal staining after either culture or frozen section.

Culture of the excised chondrocyte/collagen gels

The chondrocyte/collagen gel was minced with a scalpel into approximately 1 mm pieces in a sterile Petri dish. These pieces were transferred to another sterile Petri dish and mechanically affixed to the dish by "scratching" the tissue into the plate. Medium was then added to the dishes. So attached, the cells within the gel were allowed to migrate out of the gel, adhere to the dish, and grow to confluence, at which time they were X-gal stained as outlined previously.

Histologic preparation of the excised chondrocyte/collagen gels

The chondrocyte/collagen gels for histological analysis were placed in OCT compound, snap frozen, and cryosectioned. Transverse sections measuring 5 um in thickness were taken at 50 um intervals from the midsection of the gel; 6 sections were prepared from each sample. Each section was stained with X-gal to assess lacZ expression as outlined previously; some sections were counterstained with 0.1% nuclear fast red to assess the overall cellularity of the chondrocyte/collagen gel.

Results

Following infection with the BAG-lacZ/neo$^r$ retroviral vector, a population of cells were selected which were resistant to the toxic effects of G418. Further, approximately 60% to 80% of these cells were also stained blue by X-gal. Thus, this example shows that chondrocytes are susceptible to in vitro transduction by the retroviral vector BAG-lacZ/neo$^r$, and that they were able to express genes driven by viral promoters.

Viability and length of transgene expression of transduced chondrocytes in vivo were tested by removing the chondrocyte/collagen gels at one, two, and four weeks following transplantation and analyzed by X-gal staining after either culture or frozen section. These data are summarized in Table III.

Chondrocytes were recovered from the gels, grown to confluence, and stained with X-gal. All cultures grown from type I collagen gels containing BAG-lacZ/neo$^r$ transduced allograft articular chondrocytes had lacZ expressing cells as demonstrated by positive X-gal staining after both one (n=4) and two weeks (n=2) in vivo. However, many of the cultured cells did not stain blue. Of the chondrocytes staining blue, most were grouped in a clonal fashion. Occasional blue cells were seen individually. Qualitatively, cultures of the transduced chondrocyte/collagen gels recovered after one week in vivo contained more positively staining cells as compared to those of the gels recovered after two weeks in vivo. Neither of the cultures of chondrocyte/collagen gels harvested after four weeks (n=2) in vivo contained blue staining cells. None of the cultures grown from gels containing untransduced allograft articular chondrocytes grew cells which stained positively after either one (n=4), two (n=2), or four (n=2) weeks in vivo. Thus, allografted articular chondrocytes transduced with the lacZ gene retain the ability to express this reporter gene in culture after one and two weeks in vivo.

Frozen sections of the chondrocyte/collagen gels were stained with X-gal to assess lacZ transgene expression in situ and to assess semi-quantitatively the proportion of cells expressing the transgene. Because visualization of the cells not expressing the lacZ gene was difficult, certain frozen sections were counterstained with nuclear fast red, which stains nuclei red. X-gal staining clearly demonstrates numerous blue staining cells after one (n=4), two (n=2), and four (n=2) weeks in vivo. Counterstaining with nuclear fast red shows that the collagen gel was highly cellular after each time period in vivo, however, the majority of cells were not X-gal positive. The positively staining cells tended to occur in groups, thus making a meaningful quantitative (i.e. cell counting) analysis of in vivo expression impossible. None of the collagen gels containing untransduced chondrocytes contained blue staining cells after one (n=4), two (n=2), or four (n=2) weeks in vivo. Therefore, allotransplanted articular chondrocytes transduced by the BAG-lacZ/neo$^r$ retroviral vector continued to express the lacZ transgene in situ for at least four weeks.

Therefore, the present example shows that rabbit articular chondrocytes are susceptible to the retrovirally-mediated introduction of exogenous genes and that gene expression from viral promoters persists for at least four weeks in vivo following allotransplantation of the chondrocytes into cartilaginous defects. These findings demonstrate the feasibility of using ex vivo gene transfer to chondrocytes to repair large full-thickness articular cartilage defects.

These data demonstrate that the gene therapy methods disclosed and claimed in the present invention can be used to modulate the disease process in an animal model of arthritis. In turn, these Examples enable the claimed gene therapy based treatment of connective tissue pathologies and systemic indices of inflammation within the afflicted joint (s). It will be appreciated by those skilled in the art that this invention provides a method of introducing into a connective tissue cell of a mammalian host in vitro, or in the alternative in vivo, at least one gene which codes for proteins with therapeutic properties. This method includes employing genes having DNA that is capable of maintenance and expression.

It will be appreciated by those skilled in the art that this invention provides a method of introducing at least one gene encoding a product into at least one cell of the connective tissue of a mammalian host for treating an arthritic condition of the mammalian host.

It will be understood by those skilled in the art that this invention provides a method to repair and regenerate the connective tissue of a mammalian host.

It will be further understood that the present invention discloses ex vivo and in vivo techniques for delivery of a DNA sequence of interest to the connective tissue cells of the mammalian host. The ex vivo technique involves prior removal and culture of target autologous connective tissue cells, in vitro infection of the DNA sequence, DNA vector or other delivery vehicle of interest into the connective tissue cells, followed by transplantation to the modified connective tissue cells to the target joint of the mammalian host, so as to effect in vivo expression of the gene product of interest. The in vivo technique bypasses the requirement for in vitro culture of target connective tissues cells; instead relying on direct transplantation of the DNA sequence, DNA vector or other delivery vehicle to the target in vivo connective tissue cells, thus effecting expression of the gene product of interest.

It will also be understood that the present invention discloses ex vivo techniques for delivery of a DNA sequence of interest to in vitro cultured chondrocytes to regions of an articular cartilage defect, thus effecting expression of the gene product of interest.

It will be further understood that this invention provides a method to produce an animal model for the study of connective tissue pathology by utilizing either genetically modified synovial cells or chondrocytes cells to the appropriate region of the joint.

It will be appreciated by those persons skilled in the art that this invention provides a method of using and a method of preparing a gene encoding an extracellular interleukin-1 binding domain of an interleukin-1 receptor that is capable of binding to and neutralizing substantially all isoforms of interleukin-1, and thus substantially protect cartilage of a mammalian host from pathological degradation. In addition, it will be understood by those persons skilled in the art that the method of using the gene of this invention will reduce inflammation, protect soft tissues of the joint and suppress the loss of bone that occurs in patients suffering with arthritis.

It will be appreciated by those persons skilled in the art that the viral vectors employed in the hereinbefore described invention may be employed to transfect synovial cells in vivo or in culture, such as by direct intra-articular injection or transplantation of autologous synovial cells from the patient transduced with the retroviral vector carrying the truncated interleukin-1 receptor gene.

It will also be understood that a class of DNA sequences, as described throughout this specification, including but not limited to IRAP, may use the claimed methods to effect reduction of inflammation, protect soft tissues of the joint and suppress the loss of bone that occurs in patients suffering with arthritis.

Whereas particular embodiments of this invention have been described above for purposes of illustration, it will be evident to those persons skilled in the art that numerous variations of the details of the present invention may be made without departing from the invention as defined in the appended claims.

TABLE III

X-GAL STAINING OF ALLOGENEIC ARTICULAR CHONDROCYTES

| METHOD | RABBIT NUMBER | TIME IN VIVO (WEEKS) | LEFT KNEE TRANSDUCED+ CHONDROCYTES§ | RIGHT KNEE UNTRANSDUCED CHONDROCYTES§ |
|---|---|---|---|---|
| CULTURE | 1 | 1 | +++ | − |
|  | 2 | 1 | +++ | − |
|  | 3 | 1 | +++ | − |
|  | 4 | 1 | +++ | − |
|  | 5 | 2 | ++ | − |
|  | 6 | 2 | ++ | − |
|  | 7 | 4 | − | − |
|  | 8 | 4 | − | − |
| FROZEN SECTION | 9 | 1 | +++ | − |
|  | 10 | 1 | +++ | − |
|  | 11 | 1 | +++ | − |
|  | 12 | 1 | +++ | − |
|  | 13 | 2 | ++ | − |
|  | 14 | 2 | ++ | − |
|  | 15 | 4 | + | − |
|  | 16 | 4 | + | − |

+ CHONDROCYTES WERE TRANSDUCED USING THE RETOVIRAL VECTOR BAG-LACZ/NEOR
§RELATIVE GRADING SCALE +++ = MANY BLUE STAINING CELLS −> + = FEW BLUES STAINING CELLS − = NO BLUE STAINING CELLS

What is claimed is:

1. A method of producing a polypeptide within a mammalian chondrocyte, the method comprising generating a modified chondrocyte in vitro, said modified chondrocyte comprising a heterologous polynucleotide encoding said polypeptide, operably linked to a promoter, whereby said polypeptide is produced within said modified chondrocyte, and wherein introduction of the modified chondrocyte into a joint of a mammal and production of said polypeptide inhibits cartilage degradation or promotes cartilage growth.

2. The method of claim 1, wherein said mammal is a human.

3. The method of claim 1, wherein said joint is associated with a full-thickness articular cartilage defect.

4. The method of claim 1, wherein said joint is a knee joint.

5. The method of claim 1, wherein said heterologous polynucleotide is introduced into said chondrocyte using a viral vector.

6. The method of claim 5, wherein said viral vector is a retroviral vector.

7. The method of claim 6, wherein said retroviral vector is MFG.

8. The method of claim 5, wherein said viral vector is an adenoviral vector.

9. The method of claim 1, wherein said heterologous polynucleotide is introduced into said chondrocyte using a non-viral vector.

10. The method of claim 9, wherein said non-viral vector is introduced into said chondrocyte using a method selected from the group consisting of liposome-mediated transfection, calcium phosphate-mediated transfection, electroporation, and DEAE-dextran mediated transfection.

11. The method of claim 1, wherein said polypeptide is TGF-β1.

12. The method of claim 1, wherein said polypeptide is IRAP.

13. The method of claim 1, wherein said chondrocyte is autologous.

14. The method of claim 1, wherein said chondrocyte is introduced into a cartilage articulation within said joint using a gel solution.

15. The method of claim 14, wherein said gel is introduced into said cartilage articulation using a fixative comprising fibrinogen and thrombin.

16. The method of claim 14, wherein said gel solution comprises collagen.

17. The method of claim 1, further comprising modifing a synovial cell, said modified synovial cell comprising a heterologous polynucleotide encoding a polypeptide of interest, operably linked to a promoter; whereby said polypeptide of interest is produced within said modified synovial cell within said joint.

18. The method of claim 17, wherein said modified synovial cell is introduced into said joint by intra-articular injection.

19. The method of claim 1, wherein said polypeptide that promotes cartilage growth is selected from the group consisting of TGF-$\beta_1$, TGF-$\beta_2$, TGF-$\beta_3$, TGF-$\alpha$, IGF-1, FGF, and BMP.

20. The method of claim 1, wherein said polypeptide that causes cartilage degradation is selected from the group consisting of IL-1$\alpha$, IL-1$\beta$, TNF-$\alpha$, TNF-$\beta$, collagenase, stromelysin, and gelatinase.

21. A method of producing an non-human mammal model of arthritis, the method comprising generating a modified chondrocyte in vitro, said modified chondrocyte comprising a heterologous polynucleotide encoding a polypeptide, operably linked to a promoter, whereby said polypeptide is produced by said modified chondrocyte, and wherein introduction of the modified chondrocyte into a joint of a mammal and production of said polypeptide causes cartilage degradation.

22. The method of claim 1, wherein said polypeptide that inhibits cartilage degradation is selected from the group consisting of IRAP, soluble IL-1 receptor, soluble TNF-$\alpha$ receptor, TIMP-1, TIMP-2, TIMP-3, IL-4, IL10, vIL-10, and IL-13.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1770 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vii) IMMEDIATE SOURCE:
      (A) LIBRARY: Human T-cell cDNA Library
      (B) CLONE: Human Interleukin-1 Receptor (ix) FEATURE:
      (A) NAME/KEY: CDS
      (B) LOCATION: 55..1764

(xi) SEQUENCE DESCRIPTION: SEQ ID NO:1:

```
CCTCCTGAGA AGCTGGACCC CTTGGTAAAA GACAAGGCCT TCTCCAAGAA GAAT ATG          57
                                                            Met
                                                             1

AAA GTG TTA CTC AGA CTT ATT TGT TTC ATA GCT CTA CTG ATT TCT TCT         105
Lys Val Leu Leu Arg Leu Ile Cys Phe Ile Ala Leu Leu Ile Ser Ser
  5                  10                  15
```

```
CTG GAG GCT GAT AAA TGC AAG GAA CGT GAA GAA AAA ATA ATT TTA GTG      153
Leu Glu Ala Asp Lys Cys Lys Glu Arg Glu Glu Lys Ile Ile Leu Val
         20              25                  30

TCA TCT GCA AAT GAA ATT GAT GTT CGT CCC TGT CCT CTT AAC CCA AAT      201
Ser Ser Ala Asn Glu Ile Asp Val Arg Pro Cys Pro Leu Asn Pro Asn
     35              40                  45

GAA CAC AAA GGC ACT ATA ACT TGG TAT AAA GAT GAC AGC AAG ACA CCT      249
Glu His Lys Gly Thr Ile Thr Trp Tyr Lys Asp Asp Ser Lys Thr Pro
 50              55                  60                      65

GTA TCT ACA GAA CAA GCC TCC AGG ATT CAT CAA CAC AAA GAG AAA CTT      297
Val Ser Thr Glu Gln Ala Ser Arg Ile His Gln His Lys Glu Lys Leu
             70                  75                  80

TGG TTT GTT CCT GCT AAG GTG GAG GAT TCA GGA CAT TAC TAT TGC GTG      345
Trp Phe Val Pro Ala Lys Val Glu Asp Ser Gly His Tyr Tyr Cys Val
                 85                  90                  95

GTA AGA AAT TCA TCT TAC TGC CTC AGA ATT AAA ATA AGT GCA AAA TTT      393
Val Arg Asn Ser Ser Tyr Cys Leu Arg Ile Lys Ile Ser Ala Lys Phe
                     100                 105                 110

GTG GAG AAT GAG CCT AAC TTA TGT TAT AAT GCA CAA GCC ATA TTT AAG      441
Val Glu Asn Glu Pro Asn Leu Cys Tyr Asn Ala Gln Ala Ile Phe Lys
                         115                 120                 125

CAG AAA CTA CCC GTT GCA GGA GAC GGA GGA CTT GTG TGC CCT TAT ATG      489
Gln Lys Leu Pro Val Ala Gly Asp Gly Gly Leu Val Cys Pro Tyr Met
130                 135                 140                 145

GAG TTT TTT AAA AAT GAA AAT AAT GAG TTA CCT AAA TTA CAG TGG TAT      537
Glu Phe Phe Lys Asn Glu Asn Asn Glu Leu Pro Lys Leu Gln Trp Tyr
                     150                 155                 160

AAG GAT TGC AAA CCT CTA CTT CTT GAC AAT ATA CAC TTT AGT GGA GTC      585
Lys Asp Cys Lys Pro Leu Leu Leu Asp Asn Ile His Phe Ser Gly Val
                         165                 170                 175

AAA GAT AGG CTC ATC GTG ATG AAT GTG GCT GAA AAG CAT AGA GGG AAC      633
Lys Asp Arg Leu Ile Val Met Asn Val Ala Glu Lys His Arg Gly Asn
                 180                 185                 190

TAT ACT TGT CAT GCA TCC TAC ACA TAC TTG GGC AAG CAA TAT CCT ATT      681
Tyr Thr Cys His Ala Ser Tyr Thr Tyr Leu Gly Lys Gln Tyr Pro Ile
     195                 200                 205

ACC CGG GTA ATA GAA TTT ATT ACT CTA GAG GAA AAC AAA CCC ACA AGG      729
Thr Arg Val Ile Glu Phe Ile Thr Leu Glu Glu Asn Lys Pro Thr Arg
210                 215                 220                 225

CCT GTG ATT GTG AGC CCA GCT AAT GAG ACA ATG GAA GTA GAC TTG GGA      777
Pro Val Ile Val Ser Pro Ala Asn Glu Thr Met Glu Val Asp Leu Gly
                     230                 235                 240

TCC CAG ATA CAA TTG ATC TGT AAT GTC ACC GGC CAG TTG AGT GAC ATT      825
Ser Gln Ile Gln Leu Ile Cys Asn Val Thr Gly Gln Leu Ser Asp Ile
                         245                 250                 255

GCT TAC TGG AAG TGG AAT GGG TCA GTA ATT GAT GAA GAT GAC CCA GTG      873
Ala Tyr Trp Lys Trp Asn Gly Ser Val Ile Asp Glu Asp Asp Pro Val
                 260                 265                 270

CTA GGG GAA GAC TAT TAC AGT GTG GAA AAT CCT GCA AAC AAA AGA AGG      921
Leu Gly Glu Asp Tyr Tyr Ser Val Glu Asn Pro Ala Asn Lys Arg Arg
     275                 280                 285

AGT ACC CTC ATC ACA GTG CTT AAT ATA TCG GAA ATT GAA AGT AGA TTT      969
Ser Thr Leu Ile Thr Val Leu Asn Ile Ser Glu Ile Glu Ser Arg Phe
290                 295                 300                 305

TAT AAA CAT CCA TTT ACC TGT TTT GCC AAG AAT ACA CAT GGT ATA GAT      1017
Tyr Lys His Pro Phe Thr Cys Phe Ala Lys Asn Thr His Gly Ile Asp
                     310                 315                 320

GCA GCA TAT ATC CAG TTA ATA TAT CCA GTC ACT AAT TTC CAG AAG CAC      1065
Ala Ala Tyr Ile Gln Leu Ile Tyr Pro Val Thr Asn Phe Gln Lys His
```

```
ATG ATT GGT ATA TGT GTC ACG TTG ACA GTC ATA ATT GTG TGT TCT GTT    1113
Met Ile Gly Ile Cys Val Thr Leu Thr Val Ile Ile Val Cys Ser Val
        340             345             350

TTC ATC TAT AAA ATC TTC AAG ATT GAC ATT GTG CTT TGG TAC AGG GAT    1161
Phe Ile Tyr Lys Ile Phe Lys Ile Asp Ile Val Leu Trp Tyr Arg Asp
    355             360             365

TCC TGC TAT GAT TTT CTC CCA ATA AAA GCT TCA GAT GGA AAG ACC TAT    1209
Ser Cys Tyr Asp Phe Leu Pro Ile Lys Ala Ser Asp Gly Lys Thr Tyr
370             375             380             385

GAC GCA TAT ATA CTG TAT CCA AAG ACT GTT GGG GAA GGG TCT ACC TCT    1257
Asp Ala Tyr Ile Leu Tyr Pro Lys Thr Val Gly Glu Gly Ser Thr Ser
                390             395             400

GAC TGT GAT ATT TTT GTG TTT AAA GTC TTG CCT GAG GTC TTG GAA AAA    1305
Asp Cys Asp Ile Phe Val Phe Lys Val Leu Pro Glu Val Leu Glu Lys
            405             410             415

CAG TGT GGA TAT AAG CTG TTC ATT TAT GGA AGG GAT GAC TAC GTT GGG    1353
Gln Cys Gly Tyr Lys Leu Phe Ile Tyr Gly Arg Asp Asp Tyr Val Gly
        420             425             430

GAA GAC ATT GTT GAG GTC ATT AAT GAA AAC GTA AAG AAA AGC AGA AGA    1401
Glu Asp Ile Val Glu Val Ile Asn Glu Asn Val Lys Lys Ser Arg Arg
    435             440             445

CTG ATT ATC ATT TTA GTC AGA GAA ACA TCA GGC TTC AGC TGG CTG GGT    1449
Leu Ile Ile Ile Leu Val Arg Glu Thr Ser Gly Phe Ser Trp Leu Gly
450             455             460             465

GGT TCA TCT GAA GAG CAA ATA GCC ATG TAT AAT GCT CTT GTT CAG GAT    1497
Gly Ser Ser Glu Glu Gln Ile Ala Met Tyr Asn Ala Leu Val Gln Asp
                470             475             480

GGA ATT AAA GTT GTC CTG CTT GAG CTG GAG AAA ATC CAA GAC TAT GAG    1545
Gly Ile Lys Val Val Leu Leu Glu Leu Glu Lys Ile Gln Asp Tyr Glu
            485             490             495

AAA ATG CCA GAA TCG ATT AAA TTC ATT AAG CAG AAA CAT GGG GCT ATC    1593
Lys Met Pro Glu Ser Ile Lys Phe Ile Lys Gln Lys His Gly Ala Ile
        500             505             510

CGC TGG TCA GGG GAC TTT ACA CAG GGA CCA CAG TCT GCA AAG ACA AGG    1641
Arg Trp Ser Gly Asp Phe Thr Gln Gly Pro Gln Ser Ala Lys Thr Arg
    515             520             525

TTC TGG AAG AAT GTC AGG TAC CAC ATG CCA GTC CAG CGA CGG TCA CCT    1689
Phe Trp Lys Asn Val Arg Tyr His Met Pro Val Gln Arg Arg Ser Pro
530             535             540             545

TCA TCT AAA CAC CAG TTA CTG TCA CCA GCC ACT AAG GAG AAA CTG CAA    1737
Ser Ser Lys His Gln Leu Leu Ser Pro Ala Thr Lys Glu Lys Leu Gln
                550             555             560

AGA GAG GCT CAC GTG CCT CTC GGG TAGCATGGA                          1770
Arg Glu Ala His Val Pro Leu Gly
            565             570
```

(2) INFORMATION FOR SEQ ID NO:2:

(i) SEQUENCE CHARACTERISTICS:
        (A) LENGTH: 569 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Val Leu Leu Arg Leu Ile Cys Phe Ile Ala Leu Leu Ile Ser
 1               5                  10                  15

Ser Leu Glu Ala Asp Lys Cys Lys Glu Arg Glu Glu Lys Ile Ile Leu
                20                  25                  30
```

-continued

```
Val Ser Ser Ala Asn Glu Ile Asp Val Arg Pro Cys Pro Leu Asn Pro
         35                  40                  45

Asn Glu His Lys Gly Thr Ile Thr Trp Tyr Lys Asp Asp Ser Lys Thr
     50                  55                  60

Pro Val Ser Thr Glu Gln Ala Ser Arg Ile His Gln His Lys Glu Lys
 65                  70                  75                  80

Leu Trp Phe Val Pro Ala Lys Val Glu Asp Ser Gly His Tyr Tyr Cys
                 85                  90                  95

Val Val Arg Asn Ser Ser Tyr Cys Leu Arg Ile Lys Ile Ser Ala Lys
             100                 105                 110

Phe Val Glu Asn Glu Pro Asn Leu Cys Tyr Asn Ala Gln Ala Ile Phe
         115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445
```

```
Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
                500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
        530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

(2) INFORMATION FOR SEQ ID NO:3:

(i) SEQUENCE CHARACTERISTICS:
        (A) LENGTH: 1782 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vii) IMMEDIATE SOURCE:
        (A) LIBRARY: Mouse T-cell cDNA Library
        (B) CLONE: Mouse Interleukin-1 Receptor (ix) FEATURE:
        (A) NAME/KEY: CDS
        (B) LOCATION: 46..1776

(xi) SEQUENCE DESCRIPTION: SEQ ID NO:3:

```
GGATGTCATC AGAGTTCCCA GTGCCCCGAA CCGTGAACAA CACAA ATG GAG AAT         54
                                                  Met Glu Asn
                                                   1

ATG AAA GTG CTA CTG GGG CTC ATT TGT CTC ATG GTG CCT CTG CTG TCG      102
Met Lys Val Leu Leu Gly Leu Ile Cys Leu Met Val Pro Leu Leu Ser
     5                  10                  15

CTG GAG ATT GAC GTA TGT ACA GAA TAT CCA AAT CAG ATC GTT TTG TTT      150
Leu Glu Ile Asp Val Cys Thr Glu Tyr Pro Asn Gln Ile Val Leu Phe
 20                  25                  30                  35

TTA TCT GTA AAT GAA ATT GAT ATT CGC AAG TGT CCT CTT ACT CCA AAT      198
Leu Ser Val Asn Glu Ile Asp Ile Arg Lys Cys Pro Leu Thr Pro Asn
                 40                  45                  50

AAA ATG CAC GGC GAC ACC ATA ATT TGG TAC AAG AAT GAC AGC AAG ACC      246
Lys Met His Gly Asp Thr Ile Ile Trp Tyr Lys Asn Asp Ser Lys Thr
             55                  60                  65

CCC ATA TCA GCG GAC CGG GAC TCC AGG ATT CAT CAG CAG AAT GAA CAT      294
Pro Ile Ser Ala Asp Arg Asp Ser Arg Ile His Gln Gln Asn Glu His
         70                  75                  80

CTT TGG TTT GTA CCT GCC AAG GTG GAG GAC TCA GGA TAT TAC TAT TGT      342
Leu Trp Phe Val Pro Ala Lys Val Glu Asp Ser Gly Tyr Tyr Tyr Cys
     85                  90                  95

ATA GTA AGA AAC TCA ACT TAC TGC CTC AAA ACT AAA GTA ACC GTA ACT      390
Ile Val Arg Asn Ser Thr Tyr Cys Leu Lys Thr Lys Val Thr Val Thr
```

```
              100                    105                    110                    115
       GTG TTA GAG AAT GAC CCT GGC TTG TGT TAC AGC ACA CAG GCC ACC TTC              438
       Val Leu Glu Asn Asp Pro Gly Leu Cys Tyr Ser Thr Gln Ala Thr Phe
                           120                    125                    130

CCA CAG CGG CTC CAC ATT GCC GGG GAT GGA AGT CTT GTG TGC CCT TAT              486
       Pro Gln Arg Leu His Ile Ala Gly Asp Gly Ser Leu Val Cys Pro Tyr
                       135                    140                    145

GTG AGT TAT TTT AAA GAT GAA AAT AAT GAG TTA CCC GAG GTC CAG TGG              534
       Val Ser Tyr Phe Lys Asp Glu Asn Asn Glu Leu Pro Glu Val Gln Trp
                   150                    155                    160

TAT AAG AAC TGT AAA CCT CTG CTT CTT GAC AAC GTG AGC TTC TTC GGA              582
       Tyr Lys Asn Cys Lys Pro Leu Leu Leu Asp Asn Val Ser Phe Phe Gly
                   165                    170                    175

GTA AAA GAT AAA CTG TTG GTG AGG AAT GTG GCT GAA GAG CAC AGA GGG              630
       Val Lys Asp Lys Leu Leu Val Arg Asn Val Ala Glu Glu His Arg Gly
       180                    185                    190                    195

GAC TAT ATA TGC CGT ATG TCC TAT ACG TTC CGG GGG AAG CAA TAT CCG              678
       Asp Tyr Ile Cys Arg Met Ser Tyr Thr Phe Arg Gly Lys Gln Tyr Pro
                           200                    205                    210

GTC ACA CGA GTA ATA CAA TTT ATC ACA ATA GAT GAA AAC AAG AGG GAC              726
       Val Thr Arg Val Ile Gln Phe Ile Thr Ile Asp Glu Asn Lys Arg Asp
                       215                    220                    225

AGA CCT GTT ATC CTG AGC CCT CGG AAT GAG ACG ATC GAA GCT GAC CCA              774
       Arg Pro Val Ile Leu Ser Pro Arg Asn Glu Thr Ile Glu Ala Asp Pro
                   230                    235                    240

GGA TCA ATG ATA CAA CTG ATC TGC AAC GTC ACG GGC CAG TTC TCA GAC              822
       Gly Ser Met Ile Gln Leu Ile Cys Asn Val Thr Gly Gln Phe Ser Asp
       245                    250                    255

CTT GTC TAC TGG AAG TGG AAT GGA TCA GAA ATT GAA TGG AAT GAT CCA              870
       Leu Val Tyr Trp Lys Trp Asn Gly Ser Glu Ile Glu Trp Asn Asp Pro
       260                    265                    270                    275

TTT CTA GCT GAA GAC TAT CAA TTT GTG GAA CAT CCT TCA ACC AAA AGA              918
       Phe Leu Ala Glu Asp Tyr Gln Phe Val Glu His Pro Ser Thr Lys Arg
                           280                    285                    290

AAA TAC ACA CTC ATT ACA ACA CTT AAC ATT TCA GAA GTT AAA AGC CAG              966
       Lys Tyr Thr Leu Ile Thr Thr Leu Asn Ile Ser Glu Val Lys Ser Gln
                       295                    300                    305

TTT TAT CGC TAT CCG TTT ATC TGT GTT GTT AAG AAC ACA AAT ATT TTT             1014
       Phe Tyr Arg Tyr Pro Phe Ile Cys Val Val Lys Asn Thr Asn Ile Phe
                   310                    315                    320

GAG TCG GCG CAT GTG CAG TTA ATA TAC CCA GTC CCT GAC TTC AAG AAT             1062
       Glu Ser Ala His Val Gln Leu Ile Tyr Pro Val Pro Asp Phe Lys Asn
                   325                    330                    335

TAC CTC ATC GGG GGC TTT ATC ATC CTC ACG GCT ACA ATT GTA TGC TGT             1110
       Tyr Leu Ile Gly Gly Phe Ile Ile Leu Thr Ala Thr Ile Val Cys Cys
       340                    345                    350                    355

GTG TGC ATC TAT AAA GTC TTC AAG GTT GAC ATA GTG CTT TGG TAC AGG             1158
       Val Cys Ile Tyr Lys Val Phe Lys Val Asp Ile Val Leu Trp Tyr Arg
                           360                    365                    370

GAC TCC TGC TCT GGT TTT CTT CCT TCA AAA GCT TCA GAT GGA AAG ACA             1206
       Asp Ser Cys Ser Gly Phe Leu Pro Ser Lys Ala Ser Asp Gly Lys Thr
                       375                    380                    385

TAC GAT GCA TAT ATT CTT TAT CCC AAG ACC CTG GGA GAG GGG TCC TTC             1254
       Tyr Asp Ala Tyr Ile Leu Tyr Pro Lys Thr Leu Gly Glu Gly Ser Phe
                   390                    395                    400

TCA GAC TTA GAT ACT TTT GTT TTT AAA CTG TTG CCT GAG GTC TTG GAG             1302
       Ser Asp Leu Asp Thr Phe Val Phe Lys Leu Leu Pro Glu Val Leu Glu
                   405                    410                    415

GGA CAG TTT GGA TAC AAG CTG TTC ATT TAT GGA AGG GAT GAC TAT GTT             1350
```

```
Gly Gln Phe Gly Tyr Lys Leu Phe Ile Tyr Gly Arg Asp Asp Tyr Val
420                 425                 430                 435

GGA GAA GAT ACC ATC GAG GTT ACT AAT GAA AAT GTA AAG AAA AGC AGG   1398
Gly Glu Asp Thr Ile Glu Val Thr Asn Glu Asn Val Lys Lys Ser Arg
                440                 445                 450

AGG CTG ATT ATC ATT CTA GTG AGA GAT ATG GGA GGC TTC AGC TGG CTG   1446
Arg Leu Ile Ile Ile Leu Val Arg Asp Met Gly Gly Phe Ser Trp Leu
                455                 460                 465

GGC CAG TCA TCT GAA GAG CAA ATA GCC ATA TAC AAT GCT CTC ATC CAG   1494
Gly Gln Ser Ser Glu Glu Gln Ile Ala Ile Tyr Asn Ala Leu Ile Gln
                470                 475                 480

GAA GGA ATT AAA ATC GTC CTG CTT GAG TTG GAG AAA ATC CAA GAC TAT   1542
Glu Gly Ile Lys Ile Val Leu Leu Glu Leu Glu Lys Ile Gln Asp Tyr
                485                 490                 495

GAG AAA ATG CCA GAT TCT ATT CAG TTC ATT AAG CAG AAA CAC GGA GTC   1590
Glu Lys Met Pro Asp Ser Ile Gln Phe Ile Lys Gln Lys His Gly Val
500                 505                 510                 515

ATT TGC TGG TCA GGA GAC TTT CAA GAA AGA CCA CAG TCT GCA AAG ACC   1638
Ile Cys Trp Ser Gly Asp Phe Gln Glu Arg Pro Gln Ser Ala Lys Thr
                520                 525                 530

AGG TTC TGG AAA AAC TTA AGA TAC CAG ATG CCA GCC CAA CGG AGA TCA   1686
Arg Phe Trp Lys Asn Leu Arg Tyr Gln Met Pro Ala Gln Arg Arg Ser
                535                 540                 545

CCA TTG TCT AAA CAC CGC TTA CTA ACC CTG GAT CCT GTG CGG GAC ACT   1734
Pro Leu Ser Lys His Arg Leu Leu Thr Leu Asp Pro Val Arg Asp Thr
                550                 555                 560

AAG GAG AAA CTG CCG GCA GCA ACA CAC TTA CCA CTC GGC TAGCATGGC     1782
Lys Glu Lys Leu Pro Ala Ala Thr His Leu Pro Leu Gly
                565                 570                 575

(2) INFORMATION FOR SEQ ID NO:4:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Asn Met Lys Val Leu Leu Gly Leu Ile Cys Leu Met Val Pro
1               5                   10                  15

Leu Leu Ser Leu Glu Ile Asp Val Cys Thr Glu Tyr Pro Asn Gln Ile
                20                  25                  30

Val Leu Phe Leu Ser Val Asn Glu Ile Asp Ile Arg Lys Cys Pro Leu
                35                  40                  45

Thr Pro Asn Lys Met His Gly Asp Thr Ile Ile Trp Tyr Lys Asn Asp
        50                  55                  60

Ser Lys Thr Pro Ile Ser Ala Asp Arg Asp Ser Arg Ile His Gln Gln
65              70                  75                  80

Asn Glu His Leu Trp Phe Val Pro Ala Lys Val Glu Asp Ser Gly Tyr
                85                  90                  95

Tyr Tyr Cys Ile Val Arg Asn Ser Thr Tyr Cys Leu Lys Thr Lys Val
                100                 105                 110

Thr Val Thr Val Leu Glu Asn Asp Pro Gly Leu Cys Tyr Ser Thr Gln
                115                 120                 125

Ala Thr Phe Pro Gln Arg Leu His Ile Ala Gly Asp Gly Ser Leu Val
                130                 135                 140

Cys Pro Tyr Val Ser Tyr Phe Lys Asp Glu Asn Asn Glu Leu Pro Glu
```

-continued

```
145                 150                 155                 160
Val Gln Trp Tyr Lys Asn Cys Lys Pro Leu Leu Leu Asp Asn Val Ser
                165                 170                 175

Phe Phe Gly Val Lys Asp Lys Leu Leu Val Arg Asn Val Ala Glu Glu
            180                 185                 190

His Arg Gly Asp Tyr Ile Cys Arg Met Ser Tyr Thr Phe Arg Gly Lys
            195                 200                 205

Gln Tyr Pro Val Thr Arg Val Ile Gln Phe Ile Thr Ile Asp Glu Asn
            210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
                260                 265                 270

Asn Asp Pro Phe Leu Ala Glu Asp Tyr Gln Phe Val Glu His Pro Ser
            275                 280                 285

Thr Lys Arg Lys Tyr Thr Leu Ile Thr Thr Leu Asn Ile Ser Glu Val
            290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
            340                 345                 350

Val Cys Cys Val Cys Ile Tyr Lys Val Phe Lys Val Asp Ile Val Leu
            355                 360                 365

Trp Tyr Arg Asp Ser Cys Ser Gly Phe Leu Pro Ser Lys Ala Ser Asp
        370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
            420                 425                 430

Asp Tyr Val Gly Glu Asp Thr Ile Glu Val Thr Asn Glu Asn Val Lys
        435                 440                 445

Lys Ser Arg Arg Leu Ile Ile Ile Leu Val Arg Asp Met Gly Gly Phe
450                 455                 460

Ser Trp Leu Gly Gln Ser Ser Glu Glu Gln Ile Ala Ile Tyr Asn Ala
465                 470                 475                 480

Leu Ile Gln Glu Gly Ile Lys Ile Val Leu Leu Glu Leu Glu Lys Ile
            485                 490                 495

Gln Asp Tyr Glu Lys Met Pro Asp Ser Ile Gln Phe Ile Lys Gln Lys
            500                 505                 510

His Gly Val Ile Cys Trp Ser Gly Asp Phe Gln Glu Arg Pro Gln Ser
            515                 520                 525

Ala Lys Thr Arg Phe Trp Lys Asn Leu Arg Tyr Gln Met Pro Ala Gln
            530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
                565                 570                 575
```

```
(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: Primer Oligonuleotide to 5'Leader Sequence of
            IL-1 Receptor (xi) SEQUENCE DESCRIPTION: SEQ ID NO:5:

GCGGATCCCC TCCTGAGAAG CT                                              22

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: Primer Oligonucleotide Upstream of
            Transmembrane Portion of (xi) SEQUENCE DESCRIPTION: SEQ ID NO:6:

GCGGATCCCA TGTGCTACTG G                                               21
```